US011801216B2

(12) United States Patent
DeBaun

(10) Patent No.: US 11,801,216 B2
(45) Date of Patent: Oct. 31, 2023

(54) ENHANCED TOOTHPASTE AND KITS

(71) Applicant: BeautyPaste LLC, New York, NY (US)

(72) Inventor: Denise DeBaun, New York, NY (US)

(73) Assignee: BEAUTYPASTE Inc., New York, NY (US)

( * ) Notice: Subject to any disclaimer, the term of this patent is extended or adjusted under 35 U.S.C. 154(b) by 81 days.

(21) Appl. No.: 17/009,149

(22) Filed: Sep. 1, 2020

(65) Prior Publication Data

US 2021/0069096 A1 Mar. 11, 2021

Related U.S. Application Data

(60) Provisional application No. 62/896,685, filed on Sep. 6, 2019.

(51) Int. Cl.

| | |
|---|---|
| ***A61K 8/99*** | (2017.01) |
| ***A61K 8/9794*** | (2017.01) |
| ***A61K 8/9789*** | (2017.01) |
| ***A61K 8/67*** | (2006.01) |
| ***A61K 8/73*** | (2006.01) |
| ***A61Q 11/00*** | (2006.01) |
| ***A61Q 19/00*** | (2006.01) |

(52) U.S. Cl.

CPC ................ *A61K 8/99* (2013.01); *A61K 8/676* (2013.01); *A61K 8/678* (2013.01); *A61K 8/735* (2013.01); *A61K 8/9789* (2017.08); *A61K 8/9794* (2017.08); *A61Q 11/00* (2013.01); *A61Q 19/00* (2013.01)

(58) Field of Classification Search

CPC ...... A61Q 19/08; A61Q 19/00; A61Q 19/007; A61Q 11/00; A61K 8/99; A61K 8/355; A61K 8/676; A61K 8/9789; A61K 8/678; A61K 8/735; A61K 8/9794; A61K 2800/88; A61K 2800/92

See application file for complete search history.

(56) References Cited

U.S. PATENT DOCUMENTS

| | | | |
|---|---|---|---|
| 3,980,767 | A | 9/1976 | Chown et al. |
| 3,992,519 | A | 11/1976 | Hofmann et al. |
| 3,996,863 | A | 12/1976 | Osborn |
| 4,024,239 | A | 5/1977 | Pader |
| 4,328,205 | A | 5/1982 | Taylor |
| 4,358,437 | A | 11/1982 | Duke |
| 4,839,156 | A | 6/1989 | Ng et al. |
| 5,114,716 | A | 5/1992 | N'Guyen et al. |
| 6,746,681 | B1 | 6/2004 | Carroll |
| 6,946,010 | B2 | 9/2005 | Huang |
| 6,998,112 | B2 | 2/2006 | Zuckerman |
| 7,196,072 | B2 | 3/2007 | Pasco et al. |
| 8,221,724 | B2 | 7/2012 | Hughes et al. |
| 8,940,278 | B2 | 1/2015 | Canham |
| 9,889,089 | B2 | 2/2018 | Golden |
| 10,272,022 | B2 | 4/2019 | Carratello et al. |
| 2004/0185014 | A1* | 9/2004 | Zuckerman .......... A61K 36/185 424/58 |
| 2007/0122363 | A1 | 5/2007 | Giniger et al. |
| 2007/0264271 | A1 | 11/2007 | ElSohly et al. |
| 2017/0281538 | A1 | 10/2017 | Golden |

FOREIGN PATENT DOCUMENTS

| | | | |
|---|---|---|---|
| CN | 101321503 | | * 12/2008 |
| DE | 102014221670 | A1 | 4/2016 |
| WO | 0033802 | A1 | 6/2000 |
| WO | 2011116220 | A2 | 9/2011 |

OTHER PUBLICATIONS

International Search Report and Written Opinion for Application No. PCT/US2020/048929, dated Nov. 13, 2020, 21 pages.

Mintel: "Premium Toothpaste (Triple Pack)",XP055747033, retrieved from www.gnpd.com <http://www.gnpd.com> Database accession No. 1815224, dated Jun. 14, 2012.

Mintel; "Original Fluoride Toothpaste",XP055746418, retrieved from www.gnpd.com <http://www.gnpd.com> Database accession No. 5938955, dated Aug. 29, 2018.

Mintel; "Toothpaste with Eucalyptus and Clove Essential Oils", XP055746404,retrieved from www.gnpd.com <http://www.gnpd.com> Database accession No. 6264667, dated Jan. 17, 2019.

Rizwan Ullah et al: Iranian Journal of Basic Medical Sciences: Potential fluoride toxicity from oral medicaments: A review, Iranian journal of basic medical sciences, pp. 841-848, XP055746464, Iran, DOI: 10.22038/ijbms,2017.9104, Retrieved from the Internet: <URL:https://www.ncbi.nlm.nih.gov/pmc/articles/PMC5651468/pdf/>IJBMS-20-841.pdf, dated Aug. 1, 2017.

Morita et al., "Chlorophyll derived from Chlorella inhibits dioxin absorption from the gastrointestinal tract and accelerates dioxin excretion in rats," (Mar. 2001) 109(3):289-94 (https://www.ncbi.nlm.nih.gov/pubmed/11333191).

Morten Løbner et al., Enhancement of Human Adaptive Immune Responses by Administration of a High-Molecular-Weight Polysaccharide Extract from the Cyanobacterium Arthrospira platensis, 11 J. Med. Food No. 2 313-22 (2008).

Multifunctional Cosmetics (2001) edited by Randy Schueller and Perry Romanowski.

Nagle et al., "Epigallocatechin-3-gallate (EGCG): Chemical and biomedical perspectives," Phytochemistry (Sep. 2006) 67(17): 1849-55 (http://www.ncbi.nlm.nih.gov/pmc/articles/PMC2903211/).

Nathan, et al., The neuropharmacology of L-theanine(N-ethyl-L-glutamine): a possible neuroprotective and cognitive enhancing agent, J Herb Pharmacother 6(2):21-30 (2006); (https://www.ncbi.nlm.nih.gov/pubmed/17182482 <https://protect-us.mimecast.com/s/BdQGC68z0yhrXyxvFpTAO8?domain=ncbi.nlm.nih.gov>).

(Continued)

*Primary Examiner* — Lezah Roberts

(74) *Attorney, Agent, or Firm* — Lerner David LLP

(57) ABSTRACT

Toothpaste formulations supporting the health, well-being, and/or appearance of a user's skin is described herein, as are coordinated uses of such formulations. Methods of using these formulations to support the beauty, health, well-being, and/or appearance of a user's skin are described. Kits are also identified.

13 Claims, No Drawings

(56) References Cited

OTHER PUBLICATIONS

Nestor et al., “Safety and Efficacy of Oral Polypodium leucotomos Extract in Healthy Adult Subjects,” J Clin Aesthet Dermatol (2015) 8(2):19-23 (https://www.ncbi.nlm.nih.gov/pmc/articles/PMC4345929/).
Nguyen, M.T. and F. Gotz, Lipoproteins of Gram-Positive Bacteria: Key Players in the Immune Response and Virulence. Microbiol Mol Biol Rev, 2016. 80(3): p. 891-903.
Nielsen, C.H., et al., Enhancement of natural killer cell activity in healthy subjects by Immulina(R), a Spirulina extract enriched for Braun-type lipoproteins. Planta Med, 2010. 76(16): p. 1802-8.
Nobre, et al., “L-theanine, a natural constituent in tea, and its effect on mental state,” Asia Pac J Clin Nutr 17 Suppl 1:167-8 (2008); (https://www.ncbi.nlm.nih.gov/pubmed/18296328 <https://protect-us.mimecast.com/s/qjQvC2k19rFp78AzInb4ij?domain=ncbi.nlm.nih.gov>).
Odabasoglu et al. “?-Lipoic acid has anti-inflammatory and anti-oxidative properties: an experimental study in rats with carrageenan-induced acute and cotton pellet-induced chronic inflammations,” Br J Nutr. (Jan. 2011) 105(1):31-43.
Oe, et al., “Oral hyaluronan relieves wrinkles: a double-blinded, placebo-controlled study over a 12-week period,” Clin Cosmet Investig Dermatol <https://www.ncbi.nlm.nih.gov/pmc/articles/PMC5522662/> (2017) 10: 267-273.
Panossian & Wikman, “Evidence-based efficacy of adaptogens in fatigue, and molecular mechanisms related to their stress-protective activity,” Curr Clin Pharmacol. (2009) 4(3):198-219 (https://www.ncbi.nlm.nih.gov/pubmed/19500070).
Panossian & Wikman, “Evidence-based efficacy of adaptogens in fatigue, and molecular mechanisms related to their stress-protective activity,” Curr Clin Pharmacol. (Sep. 2009) 4(3):198-219 (http://www.ncbi.nlm.nih.gov/pubmed/19500070).
Panossian & Wikman, “Pharmacology of Schisandra chinensis Bail.: an overview of Russian research and uses in medicine,” J Ethnopharmacol. (2008) 118(2):183-212 (https://www.ncbi.nlm.nih.gov/pubmed/18515024).
Pauline McLoone et al., Honey: A Therapeutic Agent for Disorders of the Skin, 5 CAJGH No. 1 (2016) ISSN 2166-7403 (online).
Pilkington et al., “Randomized controlled trial of oral omega-3 PUFA in solar-simulated radiation-induced suppression of human cutaneous immune responses,” Am J Clin Nutr vol. 97, Issue 3 (Mar. 2013) 646-652 (https://academic.oup.com/ajcn/article/97/3/646/4571525).
Pugh et al, “Characterization of Aloeride, a New High-Molecular-Weight Polysaccharide from Aloe vera with Potent Immunostimulatory Activity,” J. Agric. Food Chem. (2001) 49 pp. 1030-1034.
Pugh et al., Isolation of Three High Molecular Weight Polysaccharide Preparations with Potent Immunostimulatory Activity from Spirulina platensis, Aphanizomenon flos-aquae and Chlorella pyrenoidosa, 67 Planta Med 737-42 (2001).
Pugh, N.D., et al., Oral administration of a Spirulina extract enriched for Braun-type lipoproteins protects mice against influenza A (H1N1) virus infection. Phytomedicine, 2015. 22(2): p. 271-6.
Pumori Saokar Telang, Vitamin C in Dermatology,: Indian Dermatology Online Journal 4, No. 2 (Apr.-Jun. 2013): 143-146.
Robbins JA, et al. “Women’s Health Initiative clinical trials: interaction of calcium and Vitamin D with hormone therapy.” Menopause. Feb. 2014. (https://www.ncbi.nlm.nih.gov/pubmed/23799356).
S.K. Katiyar, “Skin Photoprotection by Green Tea: Antioxidant and Immunomodulatory Effects,” Current Drug Targets: Immune, Endocrine and Metabolic Disorders 3, No. 3 (Sep. 2003): 234-42 (https://www.ncbi.nlm.nih.gov/pubmed/12871030).
Sato, Toshihide et al. “Clinical effects of dietary hyaluronic acid on dry, rough skin.” 12 Aesthetic Dermatology 109-120 (2002).
Schagen et al., Discovering the link between nutrition and skin aging, 4 Dermatoendocrinol. No. 3, 298-307 (2012).
Sergeant et al., “Gamma-linolenic acid, Dihommo-gamma linolenic, Eicosanoids and Inflammatory Processes,” 785 Eur J Pharmacol. 77-86 (Aug. 15, 2016) (Published online Apr. 12, 2016 https://www.ncbi.nlm.nih.gov/pmc/articles/PMC4975646/ <https://protect-us.mimecast.com/s/0kXBCBBRnpu7v8JvFzDR4s?domain=ncbi.nlm.nih.gov>).
Setti, et al., Hydroxycinnamic acids as natural antioxidants, 83 La Chimica e l’Industria RICH MAC Magazine 1-5 (2001).
Singh et al., Chemomodulatory action of Aloe vera on the profiles of enzymes associated with carcinogen metabolism and antioxidant status regulation in mice, Phytomedicine (Jun. 2000) 7(3):209-19.
Son & Lewis, Free Radical Scavenging and Antioxidative Activity of Caffeic Acid Amide and Ester Analogues: Structure-Activity Relationship, 50 J. Agric. Food Chem. 468-472 (2002).
Sreelatha & Padma, “Antioxidant activity and total phenolic content of Moringa oleifera leaves in two stages of maturity,” Plant Foods Hum Nutr. (2009) 64(4):303-11 (http://www.ncbi.nlm.nih.gov/pubmed/19904611).
Steenvoorden, et al., The use of endogenous antioxidants to improve photoprotection, 41 J. Photochemistry & Photobiology B: Biology 1-10 (1997).
Stevinson & Ernst, Valerian for insomnia: a systematic review of randomized clinical trials, ScienceDirect, Sleep Medicine, vol. 1, Issue 2, Apr. 1, 2000, pp. 91-99.
Stewart, et al., “Antioxidant nutrients protect against UVB-induced oxidative damage to DNA of mouse keratinocytes in culture,” 106 J Invest Dermatol. vol. 5, 1086-89 (May 1996); (https://www.ncbi.nlm.nih.gov/pubmed/8618044?dopt=Citation).
Tassell et al., Hawthorn (*Crataegus* spp.) in the treatment of cardiovascular disease, Pharmacogn Rev. Jan.-Jun. 2010; 4(7): 32-41.
Victoria Lambert, “Chlorella: the superfood that helps fight disease.” The Telegraph (2009) (https://www.telegraph.co.uk/lifestyle/wellbeing/6028408/Chlorella-the-superfood-that-helps-fight-disease.html.).
Vinson et al., Effect of Aloe Vera preparations on the human bioavailability of vitamins C and E, Phytomedicine. <https://protect-us.mimecast.com/s/GTNbCDkJ0rF5XNIBuWWyM2a?domain=ncbi.nlm.nih.gov>Nov. 2005;12(10):760-5.
Yang, Sarah, “Study finds new evidence that Vitamin C helps reduce oxidative stress in passive smokers.” UC Berkeley. Press Release (https://www.berkeley.edu/news/media/releases/2003/08/05_vitamin.shtml) Aug. 5, 2003.
Zague et al., Collagen hydrolysate intake increases skin collagen expression and suppresses matrix metalloproteinase 2 activity, J Med Food. Jun. 2011; 14(6):618-24 (https://www.ncbi.nlm.nih.gov/pubmed/21480801). <https://protect-us.mimecast.com/s/rxehCzpxn5hMK4NOT4gWwf?domain=ncbi.nlm.nih.gov>.
“Fish and Omega-3 Fatty Acids.” American Heart Association. May 2014. http://www.heart.org/HEARTORG/GettingHealthy/NutritionCenter/HealthyDietGoals/Fish-and-Omega-3-Fatty-Acids_UCM_303248_Article.jsp.
“Health Benefits of Lingonberries (Cowberries),” (https://www.healwithfood.org/health-benefits/lingonberries-cowberries-medicinal-juice.php).
“Lingonberries halt effects of high-fat diet.” News and Press Releases. Lund University. Jan. 2014. (https://www.lunduniversity.lu.se/article/lingonberries-halt-effects-of-high-fat-diet).
“Lingonberry boosts hydration with anti-aging benefits.” Personal Care Magazine (Apr. 2013) (https://www.personalcaremagazine.com/story/11184/lingonberry-boosts-hydration-with-anti-ageing-benefits).
“Vitamin D and Health,” Harvard School of Public Health (https://www.hsph.harvard.edu/nutritionsource/vitamin-d/<https://protect-us.mimecast.com/s/H4suCVO0NrcxMOQ4szZXTK?domain=hsph.harvard.edu>).
Alexandra Alves Rodrigues and Boban Thomas, “The Role of Lutein in the prevention of atherosclerosis,” Journal of the American College of Cardiology, vol. 40, issue No. 4 (Aug. 2002) 835 (http://www.onlinejacc.org/content/40/4/835.1 <https://protect-us.mimecast.com/s/n8BRCqxM25F89X6LTZVJCw?domain=onlinejacc.org>).
Alvarez-Suarez et al., The Composition and Biological Activity of Honey: A Focus on Manuka Honey, 3 Foods 420-32 (2014).
Alvin C. Chan, Partners in defense, vitamin E and vitamin C, 71 Canadian J. Physiology & Pharmacology No. 9 725-71 (1993).

(56) References Cited

OTHER PUBLICATIONS

Andreasen et al., Antioxidant Effects of Phenolic Rye (*Secale cereale* L.) Extracts, Monomeric Hydroxycinnamates, and Ferulic Acid Dehydromires on Human Low-Density Lipoproteins, 49 J. Agric. Food Chem. 4090-4096 (2001).
Balachandran et al., Enhancement of Natural Killer Cell Activity and Phagocytosis in Healthy Subjects by Immulina, a Spirulina Extract Enriched for Braun Type Lipoproteins, 75 Planta Medica J. Med. Plant and Natural Product Research p. 93, 450 (2009).
Balachandran et al., Toll-like receptor 2-dependent activation of monocytes by Spirulina polysaccharide and its immune enhancing action in mice, 6 Int'l Immunopharmacology 1808-14 (2006).
Beoy et al., "Effects of tocotrienol supplementation on hair growth in human volunteers," (Dec. 2010) 21(2):91-9 (https://www.ncbi_nlm.nih.gov/pubmed/24575202).
Bertrand Babinet, Ph.D., "Adaptogen Herbs: The Key to Longevity and Optimal Health," (2011) (http://www.huffingtonpost.com/dr-bertrand-babinet-phd-lac/natural-herbs_b_1167592.html).
Binic et al., "Skin Ageing: Natural Weapons and Strategies," Evid Based Complement Alternat Med. 2013; Published online Jan. 29, 2013 (https://www.ncbi.nlm.nih.gov/pmc/articles/PMC3569896/).
Bove, N.D. Mary. "Bladderwrack: An Overview of the Research and Indications." Gaia Herbs. https://docplayer.net/50198613-Bladderwrack-mary-bove-nd-an-overview-of-the-research-and-indications-fucus-vesiculosus-sponsored-by-90ltt.html.
Brown et al., "HerbalGram: Rhodiola rosea: A Phytomedicinal Overview," HerbalGram (2002): 40-52 American Botanical Council (http://cms.herbalgram.org/herbalgram/issue56/article2333.html?ts=1565890871&signature=31430f132ee4ccec49325674967011ee).
Bystritsky et al., "A pilot study of Rhodiola rosea (Rhodax) for generalized anxiety disorder (GAD)," J Altern Complement Med. (2008) 14(2):175-80 (https://www.ncbi.nlm.nih.gov/pubmed/18307390).
Cara McDonald, "The skin is a very important (and our largest) organ: what does it do?" theconversation.com, Mar. 18, 2018 (http://theconversation.com/the-skin-is-a-very-important-and-our-largest-organ-what-does-it-do-91515).
Chacko et al.,"Beneficial effects of green tea: A literature review," Chin Med. 2010; 5:13 (published online Apr. 6, 2010) (https://www.ncbi.nlm.nih.gov/pmc/articles/PMC2855614/ <https://protect-us.mimecast.com/s/UtiNCIYMpLF2LXDYIGs9uu?domain=ncbi.nlm.nih.gov>).
Eng, et al., "Molecular understanding of Epigallocatechin gallate (EGCG) in cardiovascular and metabolic diseases," 210 J Ethnopharmacol. 296-310 (Jan. 10, 2018) Epub Aug. 2017 (https://www.ncbi.nlm.nih.gov/pubmed/28864169).
Ernst Graf, Antioxidant Potential of Ferulic Acid, 13 Free Radical Biology & Medicine 435-448 (1992).
Ethem Unal., et al. "Mechanisms of Action that Contribute to Efficacy of Aesculus hippocastanum (Aescin, Horse Chestnut) in Hemorrhoidal Disease: Pharmacokinetics and Therapeutic Profile". EC Pharmacology and Toxicology 6.10 (2018): 902-904.
Fatemeh Nejatzadeh-Barandozi, Antibacterial activities and antioxidant capacity of Aloe vera, Org Med Chem Lett. 2013; 3: 5. Published online Jul. 19, 2013.
G. Sibi,. "Inhibition of lipase and inflammatory mediators by Chlorella lipid extracts for antiacne treatment," J Adv Pharm Technol Res. (Jan.-Mar. 2015) 6(1): 7-12 (https://www.ncbi.nlm.nih.gov/pubmed/25709963).
Grzanna et al., Immolina, a High-Molecular-Weight Polysaccharide Fraction of Spirulina, Enhances Chemokine Expression in Human Monocytic THP-1 Cells, 12 J. Alternative & Complementary Med. No. 5 429-35 (2006).
Gunnars, Kris, "10 Proven Benefits of Green Tea," Authority Nutrition. (https://www.healthline.com/nutrition/top-10-evidence-based-health-benefits-of-green-tea#section2) (Jan. 17, 2018).
Heyman et al. "Evaluation of Beneficial Metabolic Effects of Berries in High-Fat Fed Mice," J Nutrition and Metabolism (2014) (https://www.hindawi.com/journals/jnme/2014/403041/).
Isolauri et al., "Probiotics in the management of atopic eczema," Clin Exp Allergy (Nov. 2000) 30(11):1604-10 (http://www.ncbi.nlm.nih.gov/pubmed/11069570?dopt=Abstract).
Karkos et al., "Spirulina in Clinical Practice: Evidence-Based Human Applications," Review Article, Evidence-Based Complementary and Alternative Medicine vol. 2011, Article ID 531053, 4 pages (2011).
Kathleen Zelman, "The Benefits of Vitamin C," WebMD (Jul. 2014).
Kawada, et al., "Ingested hyaluronan moisturizes dry skin," Nutrition Journal 13:70 (2014) (https://www.ncbi.nlm.nih.gov/pubmed/25014997).
Ken Jones, Quenching Free Radicals With Aloe Vera, Inside Cosmeceuticals (Mar. 2008) pp. 20-23.
Kulkarni et al., "Evaluation of the antioxidant activity of wheatgrass (*Triticum aestivum* L.) as a function of growth under different conditions," 20 Phytother Res. vol. 3 (Mar. 2006) 218-27 (http://www.ncbi.nlm.nih.gov/pubmed/16521113).
Lin et al., Ferulic Acid Stabilizes a Solution of Vitamins C and E and Doubles its Photoprotection of Skin, 125 J. Investigative Dermatology 826-832 (2005).
Liu et al., "Anti-Aging Implications of Astragalus Membranaceus (Huangqi): A Well-Known Chinese Tonic," Aging and Disease vol. 8, No. 6 (Dec. 2017) 868-886.
Lobner, M., et al., Enhancement of human adaptive immune responses by administration of a high-molecular-weight polysaccharide extract from the cyanobacterium Arthrospira platensis. J Med Food, 2008. 11(2): p. 313-22.
M. Udompataikul, An oral nutraceutical containing antioxidants, minerals and glycosaminoglycans improves skin roughness and fine wrinkles, 31 Int'l J. Cosmetic Sci. 427-35 (2009).
Matasic, D.S., C. Brenner, and B. London, Emerging Potential Benefits of Modulating NAD(+) Metabolism in Cardiovascular Disease. Am J Physiol Heart Circ Physiol, 2017.
Moller et al., "Effectiveness of chondroitin sulphate in patients with concomitant knee osteoarthritis and psoriasis," 18 Osteoarthritis and Cartilage (Jun. 2010) Suppl 1:S32-40 (https://www.ncbi.nlm.nih.gov/pubmed/20399899).
Chan et al., "Partners in defense, vitamin E and vitamin C," Can J Physiol Pharmacol (Sep. 1993) 71(9):725-31 (https://www.ncbi.nlm.nih.gov/pubmed/8313238).
Chiu et al., "Efficacy of protein rich pearl powder on antioxidant status in a randomized placebo-controlled trial, " 26 J Food & Drug Analysis Issue 1 (Jan. 2018) 309-317 (https://www.sciencedirect.com/science/article/pii/S1021949817301011.).
Cho et al., Dietary Aloe Vera Supplementation Improves Facial Wrinkles and Elasticity and It Increases the Type I Procollagen Gene Expression in Human Skin in vivo, 21 Ann Dermatol. No. 1 6-11 (2009).
Clinical Research Laboratories, Inc. Final Report, A Double Blind Placebo Controlled Pilot Study to Assess the Safety and Efficacy of an Oral Supplement Designed to Diminish the Signs of Aging, Aloe Health Marketing Concepts, Inc. Study No. CRL34706, Feb. 2007.
Daniells, Stephen, "Lutein may protect eyes against long-term computer use: Study," Nutra Ingredients, Mar. 2009 (https://www.nutraingredients.com/Article/2009/03/02/Lutein-may-protect-eyes-against-long-term-computer-use-Study#).
David Cameron, "New Study Validates Longevity Pathway," Harvard Medical School News (Mar. 2013) (https://hms.harvard.edu/news/new-study-validates-longevity-pathway).
Delsin SD, Mercurio DG, Fossa MM, Maia Campos PMBG (2015) Clinical Efficacy of Dermocosmetic Formulations Containing Spirulina Extract on Young and Mature Skin: Effects on the Skin Hydrolipidic Barrier and Structural Properties. Clin Pharmacol Biopharm 4:144. doi: 10.4172/2167-065X.1000144.
Devasagayam et al., "Free radicals and antioxidants in human health: current status and future prospects," J Assoc Physicians India (Oct. 2004) 52:794-804 (https://www.ncbi.nlm.nih.gov/pubmed/15909857).
Di Nardo et al., "Efficacy and tolerability of ?-galactosidase in treating gas-related symptoms in children: a randomized, double-blind, placebo controlled trial," BMC Gastroenterol. (2013) 13:142.

(56) References Cited

OTHER PUBLICATIONS

Diepvens, et al., "Obesity and thermogenesis related to the consumption of caffeine, ephedrine, capsaicin, and green tea," 292 Am J. Physiol Regul Integr Comp Physiol. R77-85 (Jan. 2007); Epub Jul. 13, 2006 (https://www.ncbi.nlm.nih.gov/pubmed/16840650 <https://protect-us.mimecast.com/s/qRpCCPN5YITKQ3qPuzchew?domain=ncbi.nlm.nih.gov>).

Egashira, et al., Involvement of GABA(A) receptors in the neuroprotective effect of theanine on focal cerebral ischemia in mice, J Pharmacol Sci 105(2):211-4 (Oct. 2007); Epub Oct. 6, 2007. (https://www.ncbi.nlm.nih.gov/pubmed/17928735).

* cited by examiner

ENHANCED TOOTHPASTE AND KITS

CROSS-REFERENCE TO RELATED APPLICATIONS

This application claims the benefit of the filing date of U.S. Provisional Patent Application No. 62/896,685, filed Sep. 6, 2019, the disclosure of which is hereby incorporated herein by reference.

The invention relates to a toothpaste providing a convenient way to enhance the health, well-being, and/or the appearance of the user's skin, and to kits, including those that include such toothpastes and methods of their use.

BACKGROUND OF THE INVENTION

Along with proper hygiene and diet, skin care is generally accomplished in two fairly traditional ways. One or more active agents are delivered either topically or ingested, often as a liquid, tablet or capsule. There are known advantages and disadvantages to both. Topical applications are direct. One can readily apply a remedy to a specific "patch" of skin. Different types of treatments can be applied to different patches of skin. This allows for some level of control. On the other hand, it is difficult to treat a user's entire surface area, a relatively large area of skin, or an area difficult for a user to reach. In addition, topical applications can be messy and oily, risking stains to apparel, furniture, and other items. Ingestion of one or more active agents is quicker and can address a particular issue systemically. But, many people don't like taking pills. Some people have physiological or psychological problems swallowing. Others find remembering to take daily regimes, such as the daily administration of skin enhancing supplements, cumbersome or challenging. Also, adding the daily administration of a skin enhancing supplement is another thing one must do in schedules already too crowded by normal life. And, there is the matter of the additional expense. Tools and devices for in-home or professional use are also used to address signs of aging. Both also incur additional expenditures and time.

Skin health, beauty, nutrition, and appearance are not short-term issues. Skin is the body's largest organ and a complex one. It requires care. Skin plays many roles in the maintenance of life and health, but also has many potential problems, with more than 3,000 possible skin disorders. The skin holds everything in and plays a crucial role in providing an airtight, watertight and flexible barrier between the outside world and the highly regulated systems within the body. It also helps with temperature regulation, immune defense, vitamin production, and sensation.

The skin is unique in many ways, demanding much attention, and concern, in both states of disease and health. There is a huge focus on skin health. Individuals strive to have glowing, clearer, healthier, younger and fresher skin. This focus can cause secondary problems with self-esteem and mental health.

The extraordinary array of functions performed by healthy skin is still coming to light. The basic day-to-day functions include:

- Working as a barrier to protect against water loss, physical and chemical injury, and bugs
- Helping us fight bug bites, allergens, toxins and carcinogens via the parts of our immune system that exist in our skin
- Regulating our temperature by dilating and constricting blood vessels near the skin surface, controlling the transfer of heat out of the body. Temperature is also regulated by evaporative cooling due to sweat production and by the insulating effect of erect hairs on the skin surface. Heat loss is also affected by the insulating layer of subcutaneous fat
- Protecting us from UV radiation by melanin production
- Giving us the sense of touch—providing interaction with physical surroundings, allowing all fine and gross motor activities, and allowing pleasurable and sexual stimulation
- Producing Vitamin D, which helps prevent many diseases including osteoporosis, cancer, heart disease, obesity and neurological diseases
- Healing wounds
- Beauty and physical attraction—the quality and condition of the skin greatly contributes to the perception of health, wellness, youth and beauty and to overall self esteem The fact that the skin is the most visible organ makes us aware of the ageing process every minute. Binic et al., "*Skin Ageing: Natural Weapons and Strategies*," Evid Based Complement Alternat Med. 2013; Published online 2013 Jan. 29 (https://www.ncbi.nlm.nih.gov/pmc/articles/PMC3569896/).

Therefore, skin has many important roles and thus should be treated with care and respect. All too often people only start focusing on the skin once there is an abnormality, or at least a perceived problem.

Common skin concerns include dryness, sensitivity, oiliness, congestion, wrinkles, sun damage and signs of ageing. Although these states are all within the spectrum of normal functional skin, they may be considered problematic if severe or undesirable.

A key to skin care is consistency and routine, and it can take time to appreciate the results arising from skin care. A basic regime of daily protection from excessive UV radiation, protection from excessive irritation and drying (by, inter alia, avoiding drying soaps, or irritating chemicals) and aiding of the skin's barrier properties (using a moisturizing protective layer) will result in noticeable improvement in almost all skin. Switching and changing products and routines is usually counterproductive and will prevent you from seeing expected improvement in time. It's worth looking after your skin, as you'll wear it every day for the rest of your life. (See Cara McDonald, "*The skin is a very important* (*and our largest*)*organ: what does it do*?" theconversation.com, Mar. 18, 2018_http://theconversation.com/the-skin-is-a-very-important-and-our-largest-organ-what-does-it-do-91515)).

Thus, daily, or near daily, skin care offers big advantages. However, the idea that one must take an extra step or steps, on a near daily basis, whether by topical application, or ingestion or device, for the rest of life can be off-putting and deter individuals from beneficial skin care. The present invention addresses these concerns.

Toothpastes have been used to deliver substances to treat the oral cavity. And, at least one product was advertised as a toothpaste delivering vitamins and minerals. See U.S. Pat. Nos. 3,992,519; 9,889,089; 10,272,022; and Vitamin Paste—vitaminpaste.com, 159-21 Cross Bay Boulevard, Howard Beach, New York 11414. Toothpastes are known that can be swallowed. Not uncommonly, a dentist may offer a patient a gift of a fluoride toothpaste, a toothbrush and a dispenser of floss to, among other reasons, enhance the likelihood a patient will engage in proper oral cavity hygiene. Relatedly, it is also possible to purchase or to receive a travel kit including at least a travel-sized toothbrush and a travel-sized tube of toothpaste. One product is advertised under the name "Luster Premium Whites AM/PM. They can come packaged with a sonic toothbrush. Both are fluoridated and not meant to be swallowed. Both are so-called whitening toothpastes with the PM paste said to have "2×" more whitening power, presumably when compared to the AM paste. Both are mint flavored but contain different formulations. A similar product is Twice AM and PM whitening toothpastes. Twice offers an AM awakening and invigorating toothpaste and a PM calming and soothing toothpaste, both formulated with Vitamins A, C, E, and Aloe. AM is flavored with wintergreen and peppermint and PM is flavored with Peppermint Vanilla and Lavender. Another product that may no longer be commercially available was advertised as providing two tubes of toothpaste that are differently formulated is Go SMILE AM/PM luxury toothpaste. The toothpastes were allegedly both fluoridated and not meant to be swallowed. These were both so-called whitening toothpastes with different flavors based on aromatherapy—an AM "energy" toothpaste for the morning flavored with a blend of lemon, lime, orange and peppermint and a PM "tranquility" toothpaste flavored with chamomile, lavender, valerian root and vanilla and is said to be calming. They also contain hydrated silica for tooth polishing. Oral supplements such as the Morning and Night Supplements from Lumity (lumitylife.com) allegedly harnesses the power of a person's circadian rhythm. The supplements provide: vitamins A, C, D, and E, iodine, magnesium, selenium, zinc, flaxseed oil, acetyl-L-carnitine, alanine, coenzyme Q10, lysine, L-glutamine, L-arginine, L-cysteine, and turmeric root extract. According to the manufacturer, clinical studies showed users experienced improvements in skin health after 12 weeks of use including improvements in overall wellness, hydration, firmness, skin smoothness, and radiance.

It is widely accepted that oral care products are viewed as a daily necessity in a majority of consumer markets around the world. Oral care routines have become, for the most part, the first thing we do when we wake up, and the last thing we do before we go to sleep. The functional aspect of an oral care product is widely accepted with a plethora of oral health related claims. In general, consumers accept the fact that oral care products have clear dental health benefits.

The present invention offers a significant advance for the health, well-being and/or appearance of a user's skin. This is achieved by multiple factors exemplified by providing skin care active agents which do not require additional steps beyond those a user very likely already does. Moreover, the present advances recognize that one or more of certain active agents may be preferentially delivered during certain intervals or times of the day. This is achieved by adding one or more active agents for skin health and beauty or other health-related benefit in a toothpaste.

BRIEF SUMMARY OF THE INVENTION

Oral health extends way beyond the cosmetic status of our mouth and even beyond the health of our mouth, teeth, and gums. The mouth is a gateway to the rest of your body and the condition of your teeth and gums has a significant impact on their overall health and skin health. It can impact the status and healthy glow of your skin regardless of how great your topical skincare routine is. Toothpastes that can support skin care and provide skin beautifying, anti-aging benefits such as addressing signs of aging; skin irregularities; skin elasticity; collagen generation; hydration; skin nutrition; appearance of fine lines and wrinkles; skin discoloration; skin whitening; liver or age spots; skin softness; skin suppleness; skin firmness; skin sagging; skin drooping; dull skin tone; skin radiance; lines; wrinkles; crows feet; loss of volume; plumpness; luminosity; vitality; brightening; laugh lines; puffy skin around the eyes; discolored skin around the eyes; droopy eyes; scaly skin; rough skin; chapped skin; patchy skin; open pores in skin; cracked skin; dry skin; peeling skin; sunburned skin; sunspots; decollete wrinkles; crepey skin; acne; psoriasis; rosacea; and/or rash are heretofore unknown. The foundation of the invention is just such a toothpaste(s) containing active agent(s) which may be swallowed and/or absorbed from within a user's oral cavity. The active agent(s) support the health, well-being, and/or appearance of the user's skin and offer improvements to one or more of the skin conditions noted above. Preferably, the active agents, in as much of the toothpaste formulation as possible, are natural and supportive of the user's overall health and well-being as well.

The concept of using a toothpaste to help deliver "beauty" and/or "skin care" is unprecedented and offers many advantages. It avoids the inconvenience and limited applicable range of topical remedies. It addresses many of the concerns people have, both physiological and psychological to normal oral dosing. Almost everyone brushes their teeth at least once or twice a day. This activity is important for healthy teeth and gums, and is incorporated into virtually everyone's daily routine from an early age. Simply put, people have been brushing and will continue to brush their teeth every day. Thus, using toothpaste to enhance health and beauty will not be an impingement upon an individual's time or mental energy. Having been taught from early childhood of the need for brushing, individuals do not have to "remember" to brush their teeth. As such, a toothpaste and brushing are perfect vehicles for promoting skin health and well-being. Notably, toothpaste can be expelled and/or swallowed easily and can be readily incorporated without thought into one's daily routine. It should be noted, however, that "beauty" or "beautifying" in this context does not merely mean masking, such as through the use of color cosmetics. It means actually providing some benefit, including facilitating biochemical processes important to skin health or providing nutrition or hydration. It also means helping to improve the appearance, freshness, vitality, condition and quality of beautiful skin.

However, developing a toothpaste to sustain skin health and beauty is a nontrivial exercise, requiring skill, know-how and art, to say the least. The toothpaste is often going to be swallowed. The toothpaste should account for people's variable brushing habits. Some people brush once or twice a day, some after every meal, some to get a "clean, fresh mouth" refreshed sensation. This requires negotiating all of the formulation challenges of active ingredients and oral care bases with a flavor that delivers functionality and confidence. Because many of the toothpastes of the invention will be swallowed and/or absorbed in the oral cavity (often they can be expelled or swallowed), certain ingredients often found in toothpaste, most notably fluoride, are preferably excluded from some of the formulations and kits of this invention. The invention requires care in ingredient selection, including active agents, taking into account the amount of active ingredients wanted by a single use or multiple uses over a defined time period, such as the 24 hours of a day.

Unlike the ingredients packed into a tablet or capsule, toothpastes include fluid ingredients, which provide a more reactive and unstable environment. Likewise, the chemical environment of a human mouth must be considered. The active ingredients used should often be selected not only for their ability to sustain and support skin health and beauty but also such that they will not be destabilized, which can cause discoloration, adverse changes in flavor or other organoleptic properties and/or can reduce the effectiveness of these actives. For example, it has been found that resveratrol, pycnogenol, and nicotinamide riboside are very difficult to formulate in this format.

There are also physical issues to be considered that are not problems for oral tablets or topicals. If one is merely swallowing a capsule, they need not worry about how the active ingredients will impact the organoleptic sensation in the oral cavity when brushing. Certain active ingredients may have an undesirable flavor or odor that can be difficult to mask. They can also be gritty, chalky or otherwise unpleasant in terms of mouth sensation when applied during the act of brushing. And, that is before one even considers that the active ingredients must meet all of the requirements just discussed, and others, and they must also work together to impact the health, well-being and appearance of skin. In addition, there is a user expectation with a beauty product for an overall pleasing and aesthetic experience.

Despite these formulation challenges, the advantages and attributes of the present invention are many. Foremost, are the advantages already described, and describe throughout, in terms of supporting the health, well-being and/or appearances of the user's skin. Second is the ability to assist in addressing various skin health and beauty issues, using a healthcare, or personal hygiene, procedure already in the daily routine of most individuals. This eliminates the need for, or at least reduces, the additional steps necessary for a patient to take care of one of the bodies most important, and too often ignored, organs. The advantages in terms of simplifying one's daily routine cannot be ignored. Third, supporting the health, well-being and/or appearance of the user's skin without necessarily needing to apply topical formulations at inconvenient times is not trivial. You are getting ready to get dressed to go to work following a shower—an optimum time to put on certain skin health products. And then you have to wait, and wait, until the messy, sticky cream or ointment is sufficiently absorbed before applying makeup and, for body products, to not stick to your clothing. Or, you are ready to go to bed and you have to wait, and wait, to insure the products do not stain your pillowcases and sheets. Finally, and in general, more and more individuals realize that time is their most valuable, and non-renewable resource.

The use of toothpaste formulations in accordance with the invention has other advantages as well. It can be formulated to be swallowed and/or absorbed in the oral cavity, without using water. This can leave a fresh flavor and help freshen one's breath. And it offers a further time savings and convenience to the user. It allows the user to freshen their mouth, their breath and support the health of both their mouth and their skin at any time and virtually anywhere. And, there is a favorable environmental impact. There are Public Service Announcements asking people to turn their water off while they are brushing. One memorable PSA shows a child standing in front of running water while brushing while the level of water in an adjacent fish tank gets lower and lower. The advantage in terms of water savings in any given instance may seem small. However, could it save a half a gallon, per person, per day? That is over 180 gallons a year, per person. If just one in 350 people of the about 350 million people in the US were to brush without using water, the savings could be half a million gallons of water a year. As countries around the world have become more and more concerned with sustainability, seemingly small steps like brushing in the morning without water, can have profound consequences when considered over a longer period and larger population. Thus, another aspect of the invention is a method of brushing a user's teeth comprising brushing without using water and/or spitting or expelling the toothpaste.

Another aspect of sustainability is the elimination of unnecessary packaging. By use of the formulations of the invention, one can, is some embodiments, reduce or eliminate the need for other skin care products. That means less packaging that finds its way into the waste stream. Finally, there are advantages for travel and for people on the go. Instead of taking multiple products to care for their dental health, skin health, beauty and wellbeing, an individual could just take their toothpaste. This saves room and weight in luggage and simplifies packing. It also simplifies a shopping list, helps to facilitate daily sustainable practices, and to unclutter the user's life.

The invention also addresses the increasing demand for double-duty, multi-tasking, multiple-use, or multi-purpose products. Multi-tasking products are a rising trend that proves less can really be more. More and more people are multi-tasking in their everyday lives, and they are seeking low-key solutions and products with an ability to do several things at once or provide multiple benefits. More and more, consumers are seeking multi-tasking beauty products to save time, money, reduce clutter and waste and help reduce the stress of travel, even if just back and forth to work. In lieu of 10-step skin care regimens, individuals are seeking "skip care"; a minimalist, low key approach. Less steps, more results. And, as we discussed, they are more sustainable, environmentally friendly and address concerns around health and safety in professional salons.

In the book, Multifunctional Cosmetics (2001) edited by Randy Schueller and Perry Romanowski, he describes multifunctional cosmetics that can be achieved in three different ways:

1. The use of an ingredient with more than one functionality, e.g. humectant and emollient, emollient and emulsifier
2. The increased functionality of a secondary performance, e.g. two-in-one shampoo, body wash with high moisturization
3. The addition of a second functionality which would not be expected from the product: e.g. the beauty balm (BB) cream that combines makeup with skincare benefits When developing multifunctional cosmetics, especially the ones from the third category, in addition to the formulation parameters of compatibility, stability, manufacturability, fillability, safety, microbiology, patent infringement, among others, the inventor or chemist must give special attention to the performance of the cosmetic product, making sure to substantiate the claims for all the functionalities that his product is addressing.

In at least some embodiments, the invention addresses the increasing expectations of consumers seeking combinations of benefits across categories and provides beauty, skin care, oral care, and wellness benefits in one formulation.

Thus there are unexpected challenges and advantages that flow from the idea of using a toothpaste and methods of brushing one's teeth as a way to supplement and sustain the health, well-being, and/or appearance of a user's skin.

In some particular embodiments of this foundational development, there are provided toothpaste formulations which can address one or more of the health, well-being, and/or appearance of various skin conditions or address symptoms of the skin which include, without limitation: skin aging; signs of aging; skin irregularities; skin elasticity; collagen generation; hydration; skin nutrition; appearance of fine lines and wrinkles; skin discoloration; skin whitening; liver or age spots; skin softness; skin suppleness; skin firmness; skin sagging; skin drooping; dull skin tone; skin radiance; lines; wrinkles; crows feet; loss of volume; plumpness; luminosity; vitality; laugh lines; puffy skin around the eyes; discolored skin around the eyes; droopy eyes; scaly skin; rough skin; chapped skin; patchy skin; open pores in skin; cracked skin; dry skin; peeling skin; sunburned skin; sunspots; decollete wrinkles; crepey skin; acne; psoriasis; rosacea; and/or rash. In addition to these specific skin conditions, the toothpastes of the invention can be formulated to work best with and/or address, one or more of the six basic skin types: Normal, Dry, Oily, Combination, Sensitive and Acned or Acne Prone. A single toothpaste formulation may be useful for someone with any of these basic skin types. But the formulations could also be tailored to address the particular needs of particular users. For example, only, a particular active agent could be effective for addressing skin elasticity, but it also can cause some level of skin oiliness. For uses with normal, sensitive, and dry skin this may not be a problem. But it might be less desirable in uses with combination, acne prone or oily skin necessitating selection of a different active agent to address elasticity.

Basic/AM is formulated to enhance overall skin health, hydration and radiance and promote elasticity and firmness. PM promotes rejuvenation and repair, such as wrinkles and skin damage, as well as promoting sleep.

In some other embodiments of this aspect of the invention, toothpaste formulations can provide, again without limitation, in addition to other aspects of skin health noted above, benefits such as invigoration, calming, restfulness, supporting the skin detoxification, helping to address enflamed skin or supporting skin of those suffering from immunosuppressive conditions or disorders.

In still other embodiments of this aspect of the invention, toothpastes of the invention can be produced directed to the unique health, wellness, and/or skin appearance requirements of very specific subpopulations that may be underserved. Nonlimiting examples include menopausal men and women. The change in one's body chemistry can certainly affect the skin. Toothpaste formulations directed to people going through menopause or thereafter can be provided. Men's skin differs from women's skin. Toothpaste formulations of the present invention can be formulated to address these differences. Vegans, or people on specific diets, may benefit from a specific toothpaste formulation—to comply with their dietary practices and to provide, and supplement, their unique nutritional requirements. Men and women may undergo radiation therapy or chemotherapy or be on specific types of medication for prolonged periods of time. These too may provide unique challenges to their skin and formulations can be provided to help mitigate those conditions. Other such conditions are post partum depression or digestive health issues and probiotic balance leading to skin conditions such as acne and rosacea. Toothpaste formulations useful to support the health, well-being, and/or appearance of the skin of people in these subpopulations is therefore an embodiment of this as part of the invention.

When it comes to your beauty routine, sleep is considered a fountain of youth. Your body repairs itself and recovers while you sleep, and that leads to beauty benefits such as fewer wrinkles, glow, bright eyes, less puffiness around eyes, and a healthier appearance over all including less red, swollen eyes, dark circles, sagging eyelids, and paler skin, and sagging around lips. Sleep is even believed to help with the performance of topical products. If you're getting fewer than 6 hours, or a non-restful sleep, it's likely affecting your appearance i.e. "you look tired". In fact, there is already a known connection between the use of specific sleep agents and oral care. See U.S. Pat. No. 6,998,112. In another aspect, the invention includes toothpaste formulations containing active agent(s) supporting the health, well-being or appearance of a user's skin that are adapted to be used at a specific time of day or proximate some daily event. In one embodiment of this aspect, the toothpaste is specifically designed to both provide support for some specific aspect of skin health and to be used proximate to sleeping. In some of these embodiments, the toothpaste contains additional active agents which can help promote calming and restfulness. This type of toothpaste may also include active agents that work best overnight. A toothpaste to be used proximate a coffee break is another example of a toothpaste in accordance with the invention which is adapted to be used at a specific time of day or proximate a daily event.

Another aspect of the invention involves the coordinated use of at least one toothpaste formulation in accordance with the present invention. "Coordinated," "complementary," "cooperative," and other words to the same effect are used herein synonymously to explain a system or regimen of toothpaste intended to be used in a predetermined fashion to provide additional benefits beyond those realized by using a single toothpaste formulation. Toothpaste as a beautifying skincare regimen is unprecedented. For example, two different toothpastes in accordance with the present invention, both addressing skin elasticity, can be used, one at night and one in the morning. Another non-limiting example of coordinated use of a toothpaste in accordance with the present invention is a morning toothpaste designed to address skin elasticity and an evening toothpaste designed to provide skin repair and/or skin softness. A third nonlimiting example of coordinated use of a toothpaste in accordance with the present invention is a toothpaste to be used in the morning to support and promote skin elasticity and a toothpaste to be used in the evening which contains fluoride helping to prevent tooth decay—which should not be swallowed.

Another example of a coordinated use of a toothpaste in accordance with the present invention is the use of a toothpaste in the morning designed to support skin elasticity and an evening toothpaste not designed specifically to address skin health but instead to promote calming and restfulness. A still further example of the coordinated use of toothpaste in accordance with the present invention is the use of a toothpaste along with a topically applied product. For example, an AM toothpaste designed to promote skin elasticity could be used along with a cream, ointment, milk, solution, serum, gel, or salve which is intended to be topically applied to address that same and/or some other skin health issue. Alternatively, or in addition, an orally ingested supplement—one that is not formulated in the toothpaste—can be used in a coordinated fashion with a toothpaste formulated in accordance with the present invention. Other types of coordinated uses of the toothpaste formulations of the invention include coordinating a toothpaste with a flavor, brush, a color, its packaging, label, and the like. Both the formulations, their coordinated uses, and kits providing the components for their coordinated use are all contemplated as part of the invention.

Another aspect the invention includes a method of brushing including the steps of brushing with a first toothpaste and brushing with a second toothpaste, optimally each at least once a day. In some embodiments, the methods of this aspect also include the step of expelling the toothpaste after brushing. But in other aspects, one swallows at least one of the first and the second toothpastes following brushing. The first toothpaste and the second toothpastes may be different formulations and at least one of the first and second toothpastes can include at least one active agent which supports the health, well-being or appearance of a user's skin. In one embodiment of this aspect, the method includes swallowing both the first and the second toothpastes following brushing. In another, at least one of the first and second toothpastes, and possibly all of the toothpastes, include fluoride and is not to be swallowed. Nonetheless, all of the toothpastes may be formulated differently. In still another embodiment, at least one of the first and second toothpastes includes a formulation supporting the health, well-being or appearance of a user's skin to be used and expelled and/or swallowed proximate to a specified time of day such as prior to sleeping. In still another embodiment of this aspect, the first and the second toothpaste formulations are formulated to address different aspects of the health, well-being or appearance of a user's skin or other health-related benefit. In still another embodiment of this aspect, the first and the second toothpaste formulations are formulated differently, but both address the same aspects of the health, well-being or appearance of a user's skin or other health-related benefit. And, as noted above, in another embodiment of this aspect, the two differently formulated toothpastes both include fluoride, neither one intended to be swallowed and neither in this embodiment contains active agents intended to support the health, well-being, and/or appearance of skin.

In another aspect of the present invention, the method of daily brushing with toothpastes of the invention, and in particular, with two or more coordinated toothpastes which each support beautification by supporting the health, well-being and/or appearance of a user's skin is repeated daily. The repeated regimen ideally continues indefinitely. But at a minimum, this form or treatment should continue at least until sufficient results are observed. This can sometimes be observed in as little as 2 weeks of daily use. But other appropriate time periods are at least about 4 weeks, at least about 6 weeks, at least about 8 weeks, at least about 3 months, at least about 6 months and at least about 1 year. One additional aspect of the present invention also relates to methods of using a toothbrush as a way of metering or dosing toothpaste in accordance with the present invention. Either the size of the head, or a design or pattern on the head, can be used to help a user know the correct amount of a toothpaste in accordance with the present invention that should be applied and consumed/absorbed. Various improvements such as coordinating the color of the bristles to the color of the toothpaste to remind the user of the correct "dose" are also described and contemplated.

Various kits are also described to facilitate the coordinated use of toothpastes in accordance with the present invention and/or to improve the overall experience of the user and these kits may include, without limitation: multiple tubes of different toothpaste formulations; mouth washes, rinses, foams, tablets; brushes; applicators; flosses; washes; holders; covers; teeth whitening apparatus; and the like.

Some representative toothpaste formulations in accordance with the present invention which can support the health, well-being and/or appearance of a user's skin, either comprise, or consist essentially of, one or more of the following active agents which are delivered to the user in the following amounts:

Spirulina/IMMULINA 1 mg-1,000 mg;
Aloe 1 mg-1,000 mg;
CoQ10 1 mg-1,000 mg;
Bilberry 1 mg-1,000 mg;
Glucosamine 1 mg-1,000 mg;
Vitamin E 1 mg-1,000 mg;
Vitamin C 1 mg-1,000 mg; and/or
HA 1 mg-1,000 mg.

IMMULINA® is a Spirulina extract enriched for Braun-type lipoproteins and is and has been discovered to be particularly useful in the formulations and methods of the invention. Spirulina is a biomass of cyanobacteria or blue-green algae and can be used in place of IMMULINA unless otherwise indicated. Other active agents identified herein can be added or substituted for at least some of the active agents identified above. One such ingredient, without limitation is SOLIDENTI which is a mixture of (*Centella asiatica* extract (CAS No. 84696-21-9)—5%; *Polygonum cuspidatum* Root extract—2%; *Scutellaria baicalensis* Root extract (CAS No. 9427-99-9)—2%; *Camellia sinensis* Leaf extract (CAS No. 84650-60-2)—1%; *Glycyrrhiza glabre* (Licorice) Root extract (84775-66-6)—1%; *Chamomilla recutita* (Matricaria) Flower extract (CAS No. 84082-60-0)—0.5%; *Rosmarinus Officinalis* (Rosemary) Leaf extract (CAS No. 84604-14-8)—0.5%; and *Salvia Officinalis* (Sage) extract (CAS No. 8022-56-8)—0.5% with the balance being propanediol and water). "SOLIDENTI" will be used herein to cover such a mixture of extracts in these amounts with the understanding that the specific genus and species and the individual amounts can be varied. Here, SOLIDENTI may be used in same amount range as noted immediately above. In another embodiment, these toothpaste formulations can comprise, or consist essentially of, one or more of the following active agents which are delivered to the user in the following amounts:

Spirulina/IMMULINA 10 mg-1,000 mg;
Aloe 10 mg-1,000 mg;
CoQ10 10 mg-1,000 mg;
Bilberry 10 mg-1,000 mg;
Glucosamine 10 mg-1,000 mg;
Vitamin E 10 mg-1,000 mg;
Vitamin C 10 mg-1,000 mg; and/or
HA 10 mg-1,000 mg.

Other active agents identified herein can be added or substituted for at least some of the active agents identified above. One such active agent which may be used is SOLIDENTI used in same amount range as noted immediately above. In still another embodiment, these toothpaste formulations can comprise, or consist essentially of, one or more of the following active agents which are delivered to the user in the following amounts:

Spirulina/IMMULINA 10 mg-500 mg;
Aloe 10 mg-500 mg;
CoQ10 10 mg-500 mg;
Bilberry 10 mg-500 mg;
Glucosamine 10 mg-500 mg;
Vitamin E 10 mg-500 mg;
Vitamin C 10 mg-500 mg; and/or
HA 10 mg-500 mg;
Rosemary 0.1 mg to 250 mg;
Chamomile 0.1 mg to 250 mg;
Tea 0.1 mg to 250 mg;
Sage 0.1 mg to 250 mg;
Centella 0.1 mg to 250 mg;
Licorice 0.1 mg to 250 mg;
Japanese Knotweed 0.1 mg to 250 mg; and/or
Skullcap 0.1 mg to 250 mg;

Other active agents identified herein can be added or substituted for at least some of the active agents identified above.

In a further embodiment of any of the foregoing, the toothpaste formulation includes at least three of: Spirulina/IMMULINA; Aloe; CoQ10; Bilberry; Glucosamine; Vitamin E; Vitamin C; and/or HA, each provided in an amount of about 1 mg to about 1,000 mg, about 10 to about 1,000 mg and/or about 10 mg to about 500 mg per brushing. Other active agents identified herein can be added or substituted for at least some of these active agents. In yet a further embodiment of any of the forgoing, the toothpaste formulations include at least four of: Spirulina/IMMULINA; Aloe; CoQ10; Bilberry; Glucosamine; Vitamin E; Vitamin C; and/or HA, each provided in an amount of about 1 mg to about 1,000 mg, about 10 to about 1,000 mg and/or about 10 mg to about 500 mg per brushing. Other active agents identified herein can be added or substituted for at least some of these active agents. In yet a further embodiment of any of the forgoing, the toothpaste formulations include at least five of: Spirulina/IMMULINA; Aloe; CoQ10; Bilberry; Glucosamine; Vitamin E; Vitamin C; and/or HA, each provided in an amount of about 1 mg to about 1,000 mg, about 10 to about 1,000 mg and/or about 10 mg to about 500 mg per brushing. Other active agents identified herein can be added or substituted for at least some of these active agents. In yet a further embodiment of any of the forgoing, the toothpaste formulations include at least six of: Spirulina/IMMULINA; Aloe; CoQ10; Bilberry; Glucosamine; Vitamin E; Vitamin C; and/or HA, each provided in an amount of about 1 mg to about 1,000 mg, about 10 to about 1,000 mg and/or about 10 mg to about 500 mg per brushing. Other active agents identified herein can be added or substituted for at least some of these active agents. In another further embodiment of any of the foregoing, the toothpaste formulation includes at least seven of: Spirulina/IMMULINA; Aloe; CoQ10; Bilberry; Glucosamine; Vitamin E; Vitamin C; and/or HA, each provided in an amount of about 1 mg to about 1,000 mg, about 10 to about 1,000 mg and/or about 10 mg to about 500 mg per brushing. Other active agents identified herein can be added or substituted for at least some of these active agents. And in a final embodiment of this aspect of any of the foregoing, the toothpaste formulation of the invention includes at least the eight ingredients: Spirulina/IMMULINA; Aloe; CoQ10; Bilberry; Glucosamine; Vitamin E; Vitamin C; and/or HA, each provided in an amount of about 1 mg to about 1,000 mg, about 10 to about 1,000 mg and/or about 10 mg to about 500 mg per brushing. Other active agents identified herein can be added or substituted for at least some of these active agents.

Some representative toothpaste formulations in accordance with the present invention which can support the health, well-being and/or appearance of a user's skin, either comprise, or consist essentially of, one or more of the following active agents which are delivered to the user in the following amounts: Spirulina/IMMULINA; Aloe; CoQ10; Bilberry; Glucosamine; Vitamin E; Vitamin C; and/or HA, each provided in an amount of about 10 to about 1,000 mg per dose. These toothpaste formulations also include at least one of: abrasives, carriers, flavorings, colorings, stabilizers, preservatives, viscosity enhancers, pH adjusters, sparkles, gelling agents, effervescent agents, thickeners, humectants, desensitizing agents, sensitivity agents, whitening agents, mucosal adhesives, bad breath agents, gingivitis agents, astringents, and oxidizing agents. Other active agents identified herein can be included or substituted for at least some of these active agents to provide a toothpaste formulation that can address one or more of: skin aging, signs of aging, skin irregularities, skin elasticity, skin vitality, collagen generation, hydration, the appearance of fine lines and wrinkles, skin whitening, liver spots, skin softness, sagging, drooping skin, dull skin tone, lines, wrinkles, crows feet, loss of volume, plumpness, loss of elasticity and firmness, laugh lines, puffy eyes, droopy eyes, scaly, rough skin, patchy skin, open pores, dry, cracked skin, discolored patches of skin, loss of pigment, skin radiance, luminosity, skin nutrition, brightening; peeling skin, age spots, sunburn, sunspots, décolleté wrinkles, crepey skin, acne, psoriasis, rosacea, and/or rash.

Other representative toothpaste formulations in accordance with the present invention which can support the health, well-being and/or appearance of a user's skin, either comprise, or consist essentially of, one or more of the following active agents which are delivered to the user in the following amounts: Spirulina/IMMULINA; Aloe; CoQ10; Bilberry; Glucosamine; Vitamin E; Vitamin C; and/or HA, provided in an amount of about 10 to about 1,000 mg per dose, and further comprising a carrier, a flavor, and a thickener together with at least one additional active agent which can address skin aging.

Other representative toothpaste formulations in accordance with the present invention which can support the health, well-being and/or appearance of a user's skin, either comprise, or consist essentially of, one or more of the following active agents which are delivered to the user in the following amounts: Spirulina/IMMULINA; Aloe; CoQ10; Bilberry; Glucosamine; Vitamin E; Vitamin C; and/or HA, provided in an amount of about 10 to about 1,000 mg per dose, and further comprising a carrier, a flavor, and a thickener together with at least one additional active agent which can address signs of aging.

Other representative toothpaste formulations in accordance with the present invention which can support the health, well-being and/or appearance of a user's skin, either comprise, or consist essentially of, one or more of the following active agents which are delivered to the user in the following amounts: Spirulina/IMMULINA; Aloe; CoQ10; Bilberry; Glucosamine; Vitamin E; Vitamin C; and/or HA, provided in an amount of about 10 to about 1,000 mg per dose, and further comprising a carrier, a flavor, and a thickener together with at least one additional active agent which can address wrinkles.

Other representative toothpaste formulations in accordance with the present invention which can support the health, well-being and/or appearance of a user's skin, either comprise, or consist essentially of, one or more of the following active agents which are delivered to the user in the following amounts: Spirulina/IMMULINA; Aloe; CoQ10; Bilberry; Glucosamine; Vitamin E; Vitamin C; and/or HA, provided in an amount of about 10 to about 1,000 mg per dose, and further comprising a carrier, a flavor, and a thickener together with at least one additional active agent which can address elasticity and firmness.

Other representative toothpaste formulations in accordance with the present invention which can support the health, well-being and/or appearance of a user's skin, either comprise, or consist essentially of, one or more of the following active agents which are delivered to the user in the following amounts: Spirulina/IMMULINA; Aloe; CoQ10; Bilberry; Glucosamine; Vitamin E; Vitamin C; and/or HA, provided in an amount of about 10 to about 1,000 mg per dose, and further comprising a carrier, a flavor, and a thickener together with at least one additional active agent which can address luminosity.

Other representative toothpaste formulations in accordance with the present invention which can support the health, well-being and/or appearance of a user's skin, either comprise, or consist essentially of, one or more of the following active agents which are delivered to the user in the following amounts: Spirulina/IMMULINA; Aloe; CoQ10; Bilberry; Glucosamine; Vitamin E; Vitamin C; and/or HA, provided in an amount of about 10 to about 1,000 mg per dose, and further comprising a carrier, a flavor, and a thickener together with at least one additional active agent which can address sun damage.

Other representative toothpaste formulations in accordance with the present invention which can support the health, well-being and/or appearance of a user's skin, either comprise, or consist essentially of, one or more of the following active agents which are delivered to the user in the following amounts: Spirulina/IMMULINA; Aloe; CoQ10; Bilberry; Glucosamine; Vitamin E; Vitamin C; and/or HA, provided in an amount of about 10 to about 1,000 mg per dose, and further comprising a carrier, a flavor, and a thickener together with at least one additional active agent which can address skin texture and softness.

Other representative toothpaste formulations in accordance with the present invention which can support the health, well-being and/or appearance of a user's skin, either comprise, or consist essentially of, one or more of the following active agents which are delivered to the user in the following amounts: Spirulina/IMMULINA; Aloe; CoQ10; Bilberry; Glucosamine; Vitamin E; Vitamin C; and/or HA, provided in an amount of about 10 to about 1,000 mg per dose, and further comprising a carrier, a flavor, and a thickener together with at least one additional active agent which can address skin moisture and hydration.

Other representative toothpaste formulations in accordance with the present invention which can support the health, well-being and/or appearance of a user's skin, either comprise, or consist essentially of, one or more of the following active agents which are delivered to the user in the following amounts: Spirulina/IMMULINA; Aloe; CoQ10; Bilberry; Glucosamine; Vitamin E; Vitamin C; and/or HA, provided in an amount of about 10 to about 1,000 mg per dose, and further comprising a carrier, a flavor, and a thickener together with at least one additional active agent which can address skin repair.

In another embodiment, the method described herein includes using a morning formulation and a second formulation administered before sleeping, and formulations and kits for performing that method. The method and kit can include first and second toothpaste formulations, both of which include: a toothpaste base comprising 20-50 wt % of a humectant; 1-20% wt % of an abrasive selected from a carbonate, bicarbonate, phosphate, silica or silicate or an alumina; 0.5-20 wt % of binder; 1-20 wt % of a remineralizer and optionally a preservative, a sweetener, colorant, a surfactant and/or a flavor. Both the first and the second toothpastes also include at least one active agent which is: up to about 6 wt % of Glucosamine (preferably up to about 3 wt %); up to about 20 wt % of SOLIDENTI (preferably up to about 10%); up to about 6 wt % CoQ10 (preferably up to about 3 wt %); up to about 6 wt % Vitamin C (preferably up to about 3 wt %); up to about 6 wt % of hyaluronic acid (HA) (preferably up to about 3 wt %); up to about 8 wt % of Spirulina/IMMULINA (preferably up to about 4 wt %); up to about wt % of Aloe (preferably up to about 4 wt %); up to about 4 wt % of Bilberry (preferably up to about 2 wt %); and up to about 4 wt % of Vitamin E (preferably up to about 2 wt %), and mixtures thereof.

In these formulations, methods and kits, the first and second formulations can be designed and used to support any aspect of the health, well-being and/or appearance of a user's skin, but in particular, supporting issues such as: signs of skin aging; the appearance of fine lines and wrinkles; skin repair; skin hydration; skin softness; and skin elasticity. And the second toothpaste formulation often additionally includes at least one active agent supporting restfulness which is: melatonin, skullcap; rosemary; chamomile; poria; albizza flower; jujube; polygonum; valerian; lavender; hops; St John's wort; blue vervain; green tea extract, passionflower; wild lettuce; hawthorn, lemon balm and, goji, and mixtures thereof in an amount up to about 3 wt %; with the balance being water. In some particular embodiments, these methods, formulations and kits the toothpaste base includes both at least one binder selected from the group consisting of a gum, a cellulose, a clay, and a silicon dioxide, and mixtures thereof and a remineralizing agent and the active agents include SOLIDENTI (or one or more of its constituent parts) or Spirulina/IMMULINA, or both.

DETAILED DESCRIPTION

The invention refers to a "toothpaste." It will be understood that this term is used in its most generic sense and the term may include, as appropriate from context, any form including, without limitation: pastes, gels, mixed pastes and gels, creams, foams, tablets, capsules, powders, liquid rinses or washes, and the like, or any other delivery system associated with oral cavity care. Toothpaste formulations of the invention can be applied with or without a brush. Some formulations can be swished around the oral cavity, applied with a finger, and/or massaged around the oral cavity. And the toothpaste formulations of the invention can be used with water or without.

The use of the term "comprising" in a claim is meant to be open-ended such that the claim includes the recited elements as well as anything else. The phrase "consisting essentially of" is meant to include those elements and any other elements which are not inconsistent with the basic and novel characteristics of the invention.

Terms such as "about" and "substantially" are to have the meaning generally ascribed to them in this industry, but when applied to an amount of any particular ingredient should not be interpreted as less than ±10% of the recited value.

As used herein, "swallowable," "capable of being swallowed," and the like refer to a toothpaste which was designed and intended to be swallowed or otherwise ingested to deliver at least one active agent for absorption within the body, for example, through the gastrointestinal system. Of course, any toothpaste can be swallowed and, occasionally, may be swallowed in whole or in part. But certain types of toothpaste, particularly those with, for example, fluoride, should not be ingested. While one may accidentally and on occasion swallow such fluoride toothpaste formulations, such toothpastes in whole or in part, are not "swallowable" as that term is to be applied to the inventive toothpastes and are not intended to be swallowed. In some embodiments, the toothpaste formulations can be at least partially swallowed which means swallowing at least more than would incidentally be swallowed when one normally brushes their teeth. In another embodiment, the majority of the administered toothpaste formulations are swallowed and, in another embodiment, substantially all of the toothpaste formulations are swallowed. And in the methods and kits of the invention, at least one toothpaste may be designed and intended to be swallowed and at least one expelled or all of the toothpaste formulations may be designed and intended to be swallowed.

"Active agent" or "active ingredient," whether singular or plural, refers to an ingredient(s) included in the toothpaste to address, support, or sustain some aspect of the health, well-being, and/or appearance of the skin and/or is added for a specific purpose other than dental hygiene and to exert some influence on the user when used, and particularly when swallowed and/or absorbed in or from the oral cavity. There are many aspects of "beauty." Some of these include cosmetics which cover and/or color skin and may "hide" aspects of skin which are aesthetically undesirable. Active agents in accordance with the present invention are not directed to such aesthetic processes. For example, some toothpastes of the invention are designed for use in the evening and may contain ingredients that, when swallowed, are useful in promoting calm or restfulness. Such ingredients are considered "active agents." Other ingredients, such as fluoride, teeth whitening ingredients are not considered active agents in this context. It does not generally include, for example, excipients, carriers, cleansers, or aromas. Active agents in accordance with the present invention are preferably natural products and/or derived from natural products. These can be, without limitation, plant extracts, animal extracts, and derivatives thereof. And these active agents work through their ingestion and/or absorption.

Active agents may be present in their natural form or derivatized such as a salt, ester, ether, chelate, complex or the like. Active agents may be a natural or synthetic compound or extract capable of supporting some aspect of skin health, well-being, and/or appearance. Preferably, however, they are natural or nature identical. These can be used alone or in combination in any proportion. It will also be appreciated that a number of the active agents identified herein may be identical using generic names to a family of plants used as the source of active ingredients. For example, polygonum is a common term used for a genus of over 100 members of a family of flowering plants including buckwheat and species of knotweed (family polygonaceae). A recitation of such a generic name includes each of the family members individually and in combination and to various extracts or parts of each. Similarly, some of the above-recited active agents refer to, for example, the "flower." But stems, leaves, nuts, fruits, and roots of each such plant or family members and extracts from particular parts of a plant or the entire plant are contemplated.

Terms such as "support," "supporting," "sustain," "sustaining," "address" or "addressing" or similar phrases used herein in connection with active agents and the invention's formulations means that the active agent(s) and/or toothpaste formulations of the invention may contribute to the "health, well-being, and/or appearances of skin," or provide some other articulated health-related benefit, and when used in connection with a toothpaste of the invention. That an active agent, and therefore the formulation of the invention, can support or sustain the health, well-being, and/or appearance of skin or other health-related benefit can be established in several ways, including but not limited to clinical studies and popular/scientific literature. Popular literature and traditional medicine have long established the utility of certain natural products and extracts containing active agents. These may have been disclosed for treating skin, for providing skin nutrients or for addressing, stimulating, or enhancing some biochemical process which is implicated in skin health, well-being, and/or appearance. Some representative literature includes, without limitation: Schagen et al., *Discovering the link between nutrition and skin aging,* 4 Dermatoendocrinol. No. 3, 298-307 (2012); Setti, et al., *Hydroxycinnamic acids as natural antioxidants,* 83 La Chimica e l'Industria RICH MAC Magazine 1-5 (2001); Ernst Graf, *Antioxidant Potential of Ferulic Acid,* 13 Free Radical Biology & Medicine 435-448 (1992); Andreasen et al., *Antioxidant Effects of Phenolic Rye (Secale cereale L.) Extracts, Monomeric Hydroxycinnamates, and Ferulic Acid Dehydromires on Human Low-Density Lipoproteins,* 49 J. Agric. Food Chem. 4090-4096 (2001); Lin et al., *Ferulic Acid Stabilizes a Solution of Vitamins C and E and Doubles its Photoprotection of Skin,* 125 J. Investigative Dermatology 826-832 (2005); Son & Lewis, *Free Radical Scavenging and Antioxidative Activity of Caffeic Acid Amide and Ester Analogues: Structure-Activity Relationship,* 50 J. Agric. Food Chem. 468-472 (2002); Steenvoorden, et al., *The use of endogenous antioxidants to improve photoprotection,* 41 J. Photochemistry & Photobiology B: Biology 1-10 (1997); Alvin C. Chan, *Partners in defense, vitamin E and vitamin C,* 71 Canadian J. Physiology & Pharmacology No. 9 725-71 (1993); Alvarez-Suarez et al., *The Composition and Biological Activity of Honey: A Focus on Manuka Honey,* 3 Foods 420-32 (2014); Pauline McLoone et al., *Honey: A Therapeutic Agent for Disorders of the Skin,* 5 CAJGH No. 1 (2016) ISSN 2166-7403 (online); M. Udompataikul, *An oral nutraceutical containing antioxidants, minerals and glycosaminoglycans improves skin roughness and fine wrinkles,* 31 Int'l J. Cosmetic Sci. 427-35 (2009); Cho et al., *Dietary Aloe Vera Supplementation Improves Facial Wrinkles and Elasticity and It Increases the Type I Procollagen Gene Expression in Human Skin in vivo,* 21 Ann Dermatol. No. 1 6-11 (2009); and U.S. Pat. No. 5,114,716. Another example is *spirulina*, which is a high molecular weight polysaccharide fraction. See Grzanna et al., *Immolina, a High-Molecular-Weight Polysaccharide Fraction of Spirulina, Enhances Chemokine Expression in Human Monocytic THP-1 Cells,* 12 J. Alternative & Complementary Med. No. 5 429-35 (2006); Pugh et al., *Isolation of Three High Molecular Weight Polysaccharide Preparations with Potent Immunostimulatory Activity from Spirulina platensis, Aphanizomenon flos-aquae and Chlorella pyrenoidosa,* 67 Planta Med 737-42 (2001); Balachandran et al., *Toll-like receptor 2-dependent activation of monocytes by Spirulina* polysaccharide and its immune enhancing action in mice, 6 Int'l Immunopharmacology 1808-14 (2006); Morten Løbner et al., *Enhancement of Human Adaptive Immune Responses by Administration of a High-Molecular-Weight Polysaccharide Extract from the Cyanobacterium Arthrospira platensis,* 11 J. Med. Food No. 2 313-22 (2008); Balachandran et al., *Enhancement of Natural Killer Cell Activity and Phagocytosis in Healthy Subjects by Immulina, a Spirulina* Extract Enriched for Braun Type Lipoproteins, 75 Planta Medica J. Med. Plant and Natural Product Research P-93, 450 (2009); and U.S. Patent Appln. Pub. No. 2007/0264271 A1, published Nov. 15, 2007; Matasic, D. S., C. Brenner, and B. London, Emerging Potential Benefits of Modulating NAD (+) Metabolism in Cardiovascular Disease. Am J Physiol Heart Circ Physiol, 2017; Nguyen, M. T. and F. Gotz, Lipoproteins of Gram-Positive Bacteria: Key Players in the Immune Response and Virulence. Microbiol Mol Biol Rev, 2016. 80(3): p. 891-903; Lobner, M., et al., Enhancement of human adaptive immune responses by administration of a high-molecular-weight polysaccharide extract from the cyanobacterium Arthrospira platensis. J Med Food, 2008. 11 (2): p. 313-22; Nielsen, C. H., et al., Enhancement of natural killer cell activity in healthy subjects by IMMULINA®), a *Spirulina* extract enriched for Braun-type lipoproteins.

Planta Med. 2010. 76 (16): p. 1802-8; Pugh, N. D., et al., Oral administration of a *Spirulina* extract enriched for Braun-type lipoproteins protects mice against influenza A (H1N1) virus infection. Phytomedicine, 2015. 22 (2): p. 271-6; Herbal Medicine: Biomolecular and Clinical Aspects, 2nd Edition (Benzie IFF, Wachtel-Galors, eds.) Boca Raton (Fla.): CRC Press/Taylor & Francis; 2011; ABC Clinical Guide to Herbs (Mark Blumenthal ed.) published in 2003 by the American Botanical Council (PO Box 144354, Austin, Texas 78714-4345) (www.herbalgram.org) (ISBN 1-58890-157-2). Binic et al., "Skin Ageing: Natural Weapons and Strategies," Evid Based Complement Alternat Med. 2013; Published online 2013 Jan. 29 (https://www.ncbi.nlm.nih.gov/pmc/articles/PMC3569896/), is particularly useful as it organized various active agents by certain strategies to fight skin aging including free radical scavengers, anti-photoaging properties, matrix protective action, skin lightening properties, and tightening and firming action. All of the foregoing are hereby incorporated by reference.

Active agents that are clinically proven or considered to support skin health, well-being, and/or appearance, include, without limitation:

Aloe Vera

Aloe vera has been known since antiquity as an effective burn and wound healer and a soothing moisturizer, properties that have been verified by modern scientific investigation. Recent research has revealed aloe deserves a place in pollution-fighting skin care products because it has an effective barrier to pollutants, reduces oxidative stress created by pollution-generated free radicals, activates the body's detoxification system, and restores immune suppression caused by ultraviolet B (UVB) rays.

Aloe vera neutralizes oxidative stress in three ways. First, it contains a variety of antioxidants including vitamins, phenolic compounds and peroxidases that directly quench free radicals on the skin and in the body. A recent study found it exhibited a radical scavenging activity of 72 percent compared with only 65 percent for alpha-tocopherol. http://www.ncbi.nlm.nih.gov/pmc/articles/PMC3729540/ Org Med Chem Lett. 2013; 3: 5. Published online 2013 Jul. 19. doi: 10.1186/191-2858-3-5 PMCID: PMC3729540 PMID: 23870710 Antibacterial activities and antioxidant capacity of *Aloe vera* Fatemeh Nejatzadeh-Barandozi[1]

Secondly, aloe vera may also activate the body's endogenous antioxidant and enzyme systems and activate Phase II metabolism, which is responsible for inactivating, detoxifying and eliminating pollutants, including free radicals. http://www.ncbi.nlm.nih.gov/pubmed/11185732 Chemomodulatory action of Aloe vera on the profiles of enzymes associated with carcinogen metabolism and antioxidant status regulation in mice. Singh R P[1], Dhanalakshmi S, Rao A R. *Phytomedicine.* 2000 June; 7(3):209-19.

Thirdly, aloe has the ability to increase absorption of vitamins E and C. *Phytomedicine.* 2005 November; 12(10): 760-5. Effect of Aloe Vera preparations on the human bioavailability of vitamins C and E. Vinson, Ja, Al Kharrat H, Andreoli L. Department of Chemistry Scranton, PA https://www.nebi.nlm.nibov/pubmed/16323295

A study conducted by the National Center for Natural Products Research (NCNPR) at the University of Mississippi concluded that pharmaceutical development of Aloeride as an immunostimulant, either alone or in combination with other aloe components, may have significant potential for wound healing and immunotherapy. *Characterization of Aloeride, A New High-Molecular-Weight Polysaccharide from Aloe vera with Potent Immunostimulatory activity.* Nirmal Pugh, Samir, A. Ross, Mahmoud A. ElSohly and David S. Pasco, Department of Pharmacognosy, NCNPR and Dept of Pharmaceutics, Research Institute of Pharmaceutical Sciences, School of Pharmacy, University of Mississippi. J. Agric. Food Chem. (2001) 49 pp. 1030-34.

Additionally, a double-blind placebo controlled pilot study was conducted to assess the safety and efficacy of an oral supplement designed to diminish the signs of aging. The study evaluated the efficacy of an oral supplement on skin topography, skin firmness, elasticity and hydration and to diminish muscle and joint pain over a 12-week period and demonstrated a statistically significant increase in elasticity and distensibility relative to baseline. *Aloe Health Marketing Concepts, Inc. Study Number: CRL*34706, February 2007.

Aloe may be used in a wide range of doses in toothpaste formulations in accordance with the invention ranging from about 1 to about 1,000 mg, such as from about 10 to about 500 mg, 10-250 mg, and even more preferably about 50 to about 100 mg.

Vitamin D

Harvard's School of Public Health reports that an estimated 1 billion people worldwide are deficient in Vitamin D. This report also cites several studies that link Vitamin D levels with bone strength, muscle retention, heart health, and the immune system. Studies have also shown that Vitamin D can boost elasticity and collagen production in the skin while also reducing the appearance of lines, dark spots and acne. Clinical trials surmised Vitamin D supplements can be particularly beneficial to older women. See "Vitamin D and Health," Harvard School of Public Health (https://www.hsph.harvard.edu/nutritionsource/vitamin-d/); Robbins J A, et al. "*Women's Health Initiative clinical trials: interaction of calcium and Vitamin D with hormone therapy.*" Menopause (February 2014) 21(2):116-23 (https://www.ncbi.nlm.nih.gov/pubmed/23799356).

Vitamin C

Vitamin C has long been considered a workhorse ingredient backed up by clinical trials. As an antioxidant, Vitamin C helps prevent cell damage that inevitably occurs from sun, stress and time. Vitamin C can be in any number of classic forms including esters, salts, and L-ascorbic acid. A clinical study concluded that Vitamin C can protect the skin while visibly repairing sings of photo-damage and aging. See Yang, Sarah, "*Study finds new evidence that Vitamin C helps reduce oxidative stress in passive smokers.*" UC Berkeley. Press Release (https://www.berkeley.edu/news/media/releases/2003/08/05_vitamin.shtml) Aug. 5, 2003. It increases collagen production, which creates firm, beautiful, and thicker skin over time, helps to keep skin hydrated, and diminishes fine line and wrinkles. See Pumori Saokar Telang, "*Vitamin C in Dermatology,*" Indian Dermatology Online Journal 4, no 2 (April-June 2013): 143-146 (http://www.idoj.in/article.asp?issn=2229-5178;year=2013;volume=4;issue=2;spage=143;epage=146;aula st=Telang). A study published in Seminars in Preventative Alternative Medicine found that higher levels of Vitamin C lead to better health overall ranging from cardiovascular to eye health to immunity, thus promoting longevity and vitality for years to come. "A recent meta-analysis showed Vitamin C was beneficial to individuals whose immune system was weakened due to stress—a condition which is very common in our society," researchers from this study note. And, "because Vitamin C is one of the nutrients sensitive to stress, [it is] the first nutrient to be depleted in alcoholics, smokers, and obese individuals." Vitamin C is also important in helping the body with collagen production, which keeps your skin looking young and rejuvenated. This immune boosting antioxidant has also been proven to reduce oxidative stress by researchers at the University of California Berkeley. Clinically proven to boost your metabolism, Vitamin C is a powerful antioxidant that will take your energy levels to new heights. See Yang, Sarah, "*Study finds new evidence that Vitamin C helps reduce oxidative stress in passive smokers*" UC Berkeley. Press Release (https://www.berkeley.edu/news/media/releases/2003/08/05_vitamin.shtml) Aug. 5, 2003; Kathleen Zelman, "The Benefits of Vitamin C," WebMD (July 2014) (https://www.webmd.com/diet/features/the-benefits-of-vitamin-c#1).

Hyaluronic Acid

50% of the hyaluronic acid present in the body is found in the skin. It helps keep moisture and collagen locked into the skin to maintain a healthy appearance. In a randomized, double-blind, placebo-controlled clinical study it was found that ingested hyaluronic acid increased skin moisture and improved treatment outcomes for patients with dry skin. Kawada, et al., "*Ingested hyaluronan moisturizes dry skin*," Nutrition Journal 13:70 (2014) (https://www.ncbi.nlm.nih.gov/pubmed/25014997). Hyaluronic acid does a superior job of holding in moisture, allowing your skin to look and feel silky smooth. A double blind clinical study published in Aesthetic Dermatology in 2002 found that hyaluronic acid was able to increase skin moisture content and increase skin smoothness while ameliorating wrinkles. See Sato, Toshihide et al. "*Clinical effects of dietary hyaluronic acid on dry, rough skin.*" 12 Aesthetic Dermatology 109-120 (2002). A double blind placebo study, published July 2017 demonstrated that HA relieves wrinkles over a 12 week period. Oe, et al., "*Oral hyaluronan relieves wrinkles: a double-blinded, placebo-controlled study over a 12-week period*," Clin Cosmet Investig Dermatol. (2017) 10:267-273 (https://www.ncbi.nlm.nih.gov/pmc/articles/PMC5522662/).

Vitamin E

Vitamin E (any known topical or dietary form of tocopherol) has been shown to improve skin hydration and the combination of Vitamin E and Vitamin C as protective antioxidants were found to help protect the skin from damage. See Stewart, et al., "*Antioxidant nutrients protect against UVB-induced oxidative damage to DNA of mouse keratinocytes in culture,*" 106 J Invest Dermatol. Vol. 5, 1086-89 (May 1996); (https://www.ncbi.nlm.nih.gov/pubmed/8618044?dopt=Citation); Chan et al., "*Partners in defense, vitamin E and vitamin C*," Can J Physiol Pharmacol (1993 September) 71(9):725-31 (https://www.ncbi.nlm.nih.gov/pubmed/8313238). As an antioxidant, Vitamin E neutralizes free radicals that damage collagen and dry the skin. According to the University Maryland Medical Center, a healthy dose of Vitamin E can prevent premature aging and damage. A small double-blind study found the use of mixed antioxidants (including beta-carotene of Vitamin A and Vitamin E found in Arctic Repair) for 12 weeks improved skin roughness and scaling. Research suggests that Vitamin E improves capillary growth, which increases follicle circulation and moisture for fuller hair that is free split ends. See "Vitamin E." University of Maryland Medical Center. January 2012. Beoy et al., "*Effects of tocotrienol supplementation on hair growth in human volunteers*," (December 2010) 21(2):91-9 (https://www.ncbi.nlm.nih.gov/pubmed/24575202). Sunflower seed oil contains Vitamin E and fatty acids that promote shiny hair and glowing skin.

Black Currant Seed and Oil

Black currant seed oil is an excellent source of GLA (gamma linolenic acid) and ALA (alpha linolenic acid). According to University of Maryland Medical Center, GLA stimulates healthy skin and hair growth. Sergeant et al., "*Gamma-linolenic acid, Dihommo-gamma linolenic, Eicosanoids and Inflammatory Processes,*" 785 Eur J Pharmacol. 77-86 (Aug. 15, 2016) (Published online 2016 Apr. 12 https://www.ncbi.nlm.nih.gov/pmc/articles/PMC4975646/).

Lingonberry

Personal Care Magazine reports on research suggesting regular intake of lingonberry seed oil improves skin hydration and induces skin changes. See "Lingonberry boosts hydration with anti-aging benefits." Personal Care Magazine (April 2013) (https://www.personalcaremagazine.com/story/11184/lingonberry-boosts-hydration-with-anti-ageing-benefits); Heyman et al. "*Evaluation of Beneficial Metabolic Effects of Berries in High-Fat Fed Mice*," J Nutrition and Metabolism (2014) (https://www.hindawi.com/journals/jnme/2014/403041/). "Lingonberries halt effects of high-fat diet," News and Press Releases, Lund University (January 2014) (https://www.lunduniversity.lu.se/article/lingonberries-halt-effects-of-high-fat-diet); "*Health Benefits of Lingonberries* (*Cowberries*)," (https://www.healwithfood.org/health-benefits/lingonberries-cowberries-medicinal-juice.php).

Polypodium

Polypodium Leucotomos grows in Central America and has been studied for its skin benefits. Extracts of the tropical fern Polypodium Leucotomos have been found to help prevent harmful effects on the skin associated with sunlight exposure, as well as the potential to help with hyperpigmentation. A study was conducted to determine the safety of oral Polypodium Leucotomos extract administered twice daily to healthy adults for 60 days and assess its ability to provide protection against exposure to ultraviolet radiation. Design: This was a randomized, double-blind, placebo-controlled study. Setting: A single clinical research center. Participants: Healthy adult men and women between 18 and 65 years of age with Fitzpatrick skin types I to IV. Measurements: Safety assessments included a physical examination, vital signs, and clinical laboratory parameters including hematology, comprehensive metabolic panel, and prothrombin time-partial thromboplastin time were obtained at baseline and at the end of the study. Reports of adverse events were recorded. Efficacy assessments were changes in minimal erythema dose testing, ultraviolet-induced erythema intensity response, and sunburn history during the prior 60 days. Results: After two months of treatment, there were no changes in any safety assessments. The subjects in the placebo group showed a greater likelihood of experiencing episodes of sunburn (2 vs. 8 subjects; $p=0.04$) At Day 28, Polypodium Leucotomos extract-treated subjects showed greater likelihood of an increased minimal erythema dose (8 vs. 1 subject; $p=0.01$) and greater likelihood of decreased ultraviolet-induced erythema intensity (10 subjects vs. 3 subjects; $p<0.01$). Conclusion: Polypodium Leucotomos extract 240 mg taken twice daily for 60 days was a safe and effective means for reducing the damaging effects of ultraviolet radiation. Based on the excellent safety profile of Polypodium Leucotomos, additional studies using higher doses may be warranted. See Nestor et al., "*Safety and Efficacy of Oral Polypodium Leucotomos Extract in Healthy Adult Subjects*," J Clin Aesthet Dermatol (2015) 8(2):19-23 (https://www.ncbi.nlm.nih.gov/pmc/articles/PMC4345929/).

Alpha Lipoic Acid

Alpha lipoic acid (ALA) is a compound that protects the body from oxidative stress and keeps body cells functioning properly. Studies have shown ALA to be a vital antioxidant that protects the body's cells and aids in energy production. See Odabasoglu et al. "*α-Lipoic acid has anti-inflammatory*

*and anti-oxidative properties: an experimental study in rats with carrageenan-induced acute and cotton pellet-induced chronic inflammations*," Br J Nutr. (January 2011) 105(1): 31-43.

Green Tea Extract

Green tea contains powerful antioxidants called polyphenols that are key to optimal health. Green tea may also help keep a healthy weight due to tea catechins. See Gunnars, Kris, "10 *Proven Benefits of Green Tea*," Authority Nutrition. (https://www.healthline.com/nutrition/top-10-evidence-based-health-benefits-of-green-tea#section2) (Jan. 17, 2018). See also S. K. Katiyar, "*Skin Photoprotection by Green Tea: Antioxidant and Immunomodulatory Effects*," Current Drug Targets: Immune, Endocrine and Metabolic Disorders 3, no. 3 (September 2003): 234-42 (https://www.ncbi.nlm.nih.gov/pubmed/12871030); Chacko et al., "Beneficial effects of green tea: A literature review," Chin Med. 2010; 5:13 (published online 2010 Apr. 6) (https://www.ncbi.nlm.nih.gov/pmc/articles/PMC2855614/); Egashira, et al., *Involvement of GABA(A) receptors in the neuroprotective effect of theanine on focal cerebral ischemia in mice*, J Pharmacol Sci 105(2):211-4 (2007 October); Epub 2007 Oct. 6. (https://www.ncbi.nlm.nih.gov/pubmed/17928735); Nathan, et al., *The neuropharmacology of L-theanine(N-ethyl-L-glutamine): a possible neuroprotective and cognitive enhancing agent*, J Herb Pharmacother 6(2):21-30 (2006); (http://www.ncbi.nlm.nih.gov/pubmed/17182482); Nobre, et al., "L-theanine, a natural constituent in tea, and its effect on mental state," Asia Pac J Clin Nutr 17 Suppl 1:167-8 (2008); (https://www.ncbi.nlm.nih.gov/pubmed/18296328); Eng, et al., "*Molecular understanding of Epigallocatechin gallate (EGCG) in cardiovascular and metabolic diseases,*" 210 J Ethnopharmacol. 296-310 (Jan. 10, 2018) Epub 2017 August (https://www.ncbi.nlm.nih.gov/pubmed/28864169); Diepvens, et al., "*Obesity and thermogenesis related to the consumption of caffeine, ephedrine, capsaicin, and green tea,*" 292 Am J. Physiol Regul Integr Comp Physiol. R77-85 (January 2007); Epub 2006 Jul. 13 (https://www.nchi.nln.nih.gov/pubmed/16840650).

Matcha Green Tea

The Journal of Chromatography published a report showing 3 times more EGCG (these healthy antioxidants) in matcha than regular green tea. In addition, studies in animals showed antioxidant and polyphenols in green tea extracts may reduce some of the harmful effects following exposure to UV making matcha a trending skin and beauty essential. See Nagle et al., "*Epigallocatechin*-3-*gallate (EGCG): Chemical and biomedical perspectives*," Phytochemistry (September 2006) 67(17): 1849-55 (http://www.ncbi.nlm-.nih.gov/pmc/articles/PMC2903211/).

Turmeric

Turmeric is commonly used to ease arthritis symptoms, as its anti-inflammatory properties support healthy joint function. Studies have also been done on into its ability to protect the brain and skin from free radical damage, which can work to slow the aging process. Devasagayam et al., "*Free radicals and antioxidants in human health: current status and future prospects*," J Assoc Physicians India (October 2004) 52:794-804 (https://www.ncbi.nlm.nih.gov/pubmed/15909857) (https://www.researchgate.net/profile/Saroj_Ghaskadbi/publication/7831516_Free_Radicals_and_Antioxi dants_in_Human_Health_Current_Status_and_Future_Prospects/links/56ef792f08ae4b8b5e756f2e/Free-Radicals-and-Antioxidants-in-Human-Health-Current- Status-and-Future-Prospects.pdf).

Lutein

Lutein is a carotenoid vitamin that is crucial for optimal eye health, which can deteriorate as we age. Just like our skin, our eyes face immense damage overtime from sunlight. See Daniells, Stephen, "*Lutein may protect eyes against long-term computer use: Study*," Nutra Ingredients, March 2009 (https://www.nutraingredients.com/Article/2009/03/02/Lutein-may-protect-eyes-against-long-term-computer-use-Study#); Alexandra Alves-Rodrigues and Boban Thomas, "*The Role of Lutein in the prevention of atherosclerosis*," J Am College of Cardiology, vol. 40, issue no. 4 (August 2002) 835 (http://www.onlinejacc.org/content/40/4/835.1).

Collagen Peptide

Collagen is the protein found in our bodies that gives our skin its strength and elasticity. As we age, the collagen production in our bodies slows down, which can cause lines and wrinkles. Research suggests that collagen peptide may help prevent dwindling collagen levels so that your skin remains firm and vibrant. Zague et al., *Collagen hydrolysate intake increases skin collagen expression and suppresses matrix metalloproteinase* 2 *activity*," J Med Food (June 2011) 14(6):618-24 (http://www.ncbi.nlm.nih.gov/pubmed/21480801).

Chondroitin Sulfate

Chondroitin sulfate is a chemical that can be found in cartilage around the joint. Research suggests chondroitin sulfate may contain skin benefits that can support collagen levels and elasticity in the skin. See Moller et al., "*Effectiveness of chondroitin sulphate in patients with concomitant knee osteoarthritis and psoriasis,*" 18 Osteoarthritis and Cartilage (June 2010) Suppl 1:S32-40 (https://www.ncbi.nlm.nih.gov/pubmed/20399899).

Grape Seed Extract

According to the University of Maryland Medical Center, grape seed extract contains powerful antioxidants in resveratrol, within the skin of the grape, that help the body protect itself from free radicals that can damage DNA. Furthermore, grape seed extract contains Vitamin E, a crucial nutrient for healthy, younger-looking skin. See David Cameron, "*New Study Validates Longevity Pathway*," Harvard Medical School News (March 2013) (https://hms.harvard.edu/news/new-study-validates-longevity-pathway).

Omega/Fish Oil

Many studies suggest that the omega-3 fatty acids, EPA and DHA, found in the fatty layers of cold-water fish can keep your heart and body healthy. Our supplements are derived from the highest quality of sustainably sourced small fish, ensuring the purest and most nutrient-rich standards. Research connects the fatty acids in fish oil to healthy hair and skin function. According to research at the University of Manchester, the properties in fish oil have been proven to protect the skin from damaging sun rays by stimulating the production of healthy skin cells. And the benefit of fish oil extends beyond hair and skin. See Pilkington et al., "*Randomized controlled trial of oral omega*-3 *PUFA in solar-simulated radiation-induced suppression of human cutaneous immune responses*," Am J Clin Nutr Vol. 97, Issue 3 (March 2013) 646-652 (https://academic.oup-.com/ajcn/article/97/3/646/4571525); "*Fish and Omega*-3 *Fatty Acids*." American Heart Association. May 2014. http://www.heart.org/HEARTORG/GettingHealthy/NutritionCenter/HealthyDietGoals/Fish-and-Omega-3-Fatty-Acids_UCM_303218 Article.js Chlorella Experimental research has shown that several *chlorella* species inhibit lipase enzymes, free radical (ROS) and pro-inflammatory cytokines production, such as TNF-alpha, while also showing potent anti-acne activity in a test-tube setting. Furthermore, previous studies reported detoxification properties of *chlorella* which might have benefits for its complementary use in skin. See G. Sibi, "*Inhibition of lipase and inflammatory mediators by Chlorella lipid extracts for antiacne treatment*," J Adv Pharm Technol Res. (2015 January-March) 6(1): 7-12 (https://www.ncbi.nlm.nih.gov/pubmed/25709963); Morita et al., "Chlorophyll derived from *Chlorella* inhibits dioxin absorption from the gastrointestinal tract and accelerates dioxin excretion in rats," (March 2001) 109(3):289-94 (https://www.ncbi.nlm.nih.gov/pubmed/11333191). The UK paper The Telegraph reports that *chlorella* is an underutilized healthy superfood. *Chlorella* contains 9 essential amino acids, as well as vitamins, minerals, and is packed with protein. See Victoria Lambert, "*Chlorella: the superfood that helps fight disease*." The Telegraph (2009) (https://www.telegraph.co.uk/lifestyle/wellbeing/6028408/Chlorella-the-superfood-that-helps-fight-disease.html).

Wheat Grass

A study published by Phytotherapy Research evaluated and confirmed the rich antioxidant activity of wheat grass. These antioxidant properties are deduced by their capacity to absorb free radicals, a trait that is beneficial to skin and cellular function in the body. Wheat grass capacity was found to be higher than many other vegetables or extracts. See Kulkarni et al., "*Evaluation of the antioxidant activity of wheatgrass* (*Triticum aestivum L.*) *as a function of growth under different conditions,"* 20 Phytother Res. Vol. 3 (March 2006) 218-27 (http://www.ncbi.nlm.nih.gov/pubmed/16521113).

Adaptogens

The Huffington Post reported on how the natural adaptogenic herbs ginseng, eleuthero, rhodiola and ashwagandha are global system regulators, meaning they help prevent signs of aging. Grape seed, grape skin (resveratrol) and ginger support the immune system of cells. See Bertrand Babinet, Ph.D., "Adaptogen Herbs: The Key to Longevity and Optimal Health," (2011) (http://www.huffingtonpost.com/dr-bertrand-babinet-phd-lac/natural-herbs_b_1167592.html). The American Academy of Dermatology shows the negative effect of stress on the barrier function of the skin, resulting in dehydration of the skin and reducing cell renewal. To counteract these negative effects on skin, review shows the evidence-based efficacy of adaptogens to fight fatigue, with strong scientific evidence available for *Rhodiola* in improving attention, cognitive function and mental performance. See Panossian & Wikman, "*Evidence-based efficacy of adaptogens infatigue, and molecular mechanisms related to their stress-protective activity*," Curr Clin Pharmacol. (September 2009) 4(3):198-219 (http://www.ncbi.nlm.nih.gov/pubmed/19500070).

Moringa

Moringa has potent antioxidant activity that can protect the body against free radicals and prevent against oxidative damage. See Sreelatha & Padma, "*Antioxidant activity and total phenolic content of Moringa oleifera leaves in two stages of maturity*," Plant Foods Hum Nutr. (2009) 64(4): 303-11 (http://www.ncbi.nlm.nih.gov/pubmed/19904611).

Digestive Enzyme Blend

In a double-blind trial, a lipase blend (pancreatic enzymes that aid in the digestion of fats) was shown to significantly reduce gas, bloating and fullness after a high-fat meal. See Di Nardo et al., "*Efficacy and tolerability of α-galactosidase in treating gas-related symptoms in children: a randomized, double-blind, placebo controlled trial*," BMC Gastroenterol. (2013) 13:142.

Probiotic Blend

Helps support the health of your immune system. See Isolauri et al., "*Probiotics in the management of atopic eczema*," Clin Exp Allergy (November 2000) 30(11):1604-10 (http://www.ncbi.nlm.nih.gov/pubmed/11069570?dopt=Abstract).

*Rhodiola rosea* Root Extract

Rhodiola is a powerful herb to increase stamina and strength, no matter how demanding your lifestyle may be. It is an 'adaptogenic' herb, which means that it works to stabilize stress levels and promote homeostasis so that the body can easily adapt to physical and environmental strains. A 2002 article in HerbalGram reported that ingesting this herb can prevent fatigue and even increase productivity while keeping stress at bay. A small study at UCLA conducted in 2008 found that those who took the herb for 10 weeks found a significant improvement in their anxiety levels. See Brown et al., "*HerbalGram Rhodiola rosea: A Phytomedicinal Overview*," HerbalGram (2002): 40-52 American Botanical Council (http://cms.herbalgram.org/herbalgram/issue56/article2333.html?ts=1565890871&signature=31430f132e e4ccec49325674967011ee); Bystritsky et al., "*A pilot study of Rhodiola rosea* (*Rhodax*) *for generalized anxiety disorder* (*GAD*)," J Altern Complement Med. (2008) 14(2):175-80 (https://www.ncbi.nlm.nih.gov/pubmed/18307390).

Bladderwrack

Antioxidant effects, laxative effects, and the ability to improve skin elasticity have all been associated with bladderwrack in an Overview of Research sponsored by Gaia Herbs. The overview emphasized bladderwrack's medicinal applications in thyroid health and function and lipid metabolism specifically. See Bove, N. D. Mary. "Bladderwrack: An Overview of the Research and Indications." Gaia Herbs. https://docplayer.net/50198613-Bladderwrack-mary-bove-nd-an-overview-of-the-research-and-indications-fucus-vesiculosus-sponsored-by-90ltt.html.

Red Clover Extract

Red clover is rich in isoflavones, chemicals found in plants that have similar properties to estrogen. Studies have thus shown that red clover is beneficial for menopausal women. Red clover has also been used in traditional medicine to purify the blood and cleanse the body.

Milk Thistle

Research has looked into silymarin, a key extract of milk thistle, as a potent antioxidant. Antioxidants are compounds that block the action of activated oxygen molecules called free radicals, which can damage cells. Binic et al., "Skin Ageing: Natural Weapons and Strategies," Evid Based Complement Alternat Med. 2013; Published online 2013 Jan. 29 (https://www.ncbi.nlm.nih.gov/pmc/articles/PMC3569896/)

Ashwagandha

Ashwagandha, sometimes known as Indian ginseng, is one of the most commonly used adaptogen herbs in Ayurvedic healing. It helps balance and restore the body. Ashwagandha is a powerful calming agent that naturally lowers cortisol, reduces fatigue, balances thyroid hormones, and regulates immune function.

Astragalus

Traditional Chinese Medicine has used this adaptogenic herb for centuries. It's rich in antioxidants that protect the cells against oxidative damage. It also contains anti-inflammatory and antibacterial properties. Additionally, the root is traditionally used for strengthening immune function, protecting the liver, and protecting the body against the common cold. Liu et al, "Anti-Aging Implications of *Astragalus Membranaceus* (Huangqi): A Well-Known Chinese Tonic," Aging and Disease Vol. 8, No. 6 (December 2017) 868-886.

Schizandra Berry

Although a Traditional Chinese Medicinal plant, Shisandra rose in popularity in the 1960s when it became an official medicine used in the USSR. Good scientific evidence was documented in the schisandra berry to increase endurance and mental performance in patients with mild fatigue and weakness. Panossian & Wikman, "*Evidence-based efficacy of adaptogens in fatigue, and molecular mechanisms related to their stress-protective activity*," Curr Clin Pharmacol. (2009) 4(3):198-219 (https://www.ncbi.nlm.nih.gov/pubmed/19500070). Due to its status in Russia to date, a widespread review of clinical research reports multiple findings. The herb provides strong adrenal support to enhance physical performance, promotes endurance, and offers stress-protective relief. In the mind, it can help prevent mental fatigue and improve mental concentration. Panossian & Wikman, "*Pharmacology of Schisandra chinensis Bail: an overview of Russian research and uses in medicine*," J Ethnopharmacol. (2008) 118(2):183-212 (https://www.ncbi.nlm.nih.gov/pubmed/18515024).

Licorice Root

Cited in use all the way back to Ancient Egypt, licorice root has been around for centuries due to its holistic medicinal benefits. As an adaptogen, the root extract helps stimulate and balance the adrenal glands, increase energy, and boost endurance. Anti-inflammatory properties of licorice can also help soothe gut issues and restore balance. The ABC Clinical Guide to Herbs, Mark Blumenthal, American Botanical Council, Austin TX, 2003. Binic et al., "*Skin Ageing: Natural Weapons and Strategies*," Evid Based Complement Alternat Med. 2013; Published online 2013 Jan. 29 (https://www.ncbi.nlm.nih.gov/pmc/articles/PMC3569896/)

Eleuthero

Also called Siberian Ginseng, Eleuthero dates back thousands of years in Chinese Medicine to provide energy and vitality. Good scientific evidence documented its ability to increase endurance and mental performance. One study found supplementation supported high quality-of-life measures in healthy elderly people. Also, the herb may improve athletic performance, reduce fatigue, and support the normal function of the body's hormonal stress system. The ABC Clinical Guide to Herbs, Mark Blumenthal, American Botanical Council, Austin TX, 2003.

American Ginseng

Some studies show American Ginseng has the potential to boost mental performance. One study noted it helped improve short-term memory and reaction time one to six hours before cognitive tests. In addition, lab studies show American ginseng is effective in boosting the performance of cells that play a role in immunity. Furthermore, it's a potent antioxidant in the body, which indicates the potential to fight off infection and protect cells. The ABC Clinical Guide to Herbs, Mark Blumenthal, American Botanical Council, Austin TX, 2003.

Hawthorn Berry

Hawthorn Berry is an anti-oxidant, rich in bioflavonoids. Clinical research has demonstrated that constituent groups such as bioflavonoids and proanthocyanidins has shed light on some of the beneficial effects of *Crataegus*/Hawthorn on the cardiovascular system, bioflavonoids now being well established as possessing significant antioxidant activity.

Horse Chestnut

Horse Chestnut is used as an anti-inflammatory and anti-oxidant. Studies with aescin (HCSE), the active agent in Horse Chestnut, have provided an important amount of evidence for a clinically significant activity in hemorrhoidal disease. Antiedematous, anti-inflammatory, antioxidant, apoptotic and venotonic effects of aescin are important in the relief of symptoms. The excellent tolerability of the active agent in the drug indicates Horse Chestnut/HCSE is of definite benefit in these patients Pearl Powder Pearl is one of the well-known traditional Chinese medicines (TCM) prescribed for treating various skin and bone related disorders due to its abundant proteins and mineral contents. Efficacy of protein rich pearl powder on antioxidant status in a randomized placebo controlled trial is demonstrated by Chin et al. Chin et al., "*Efficacy of protein rich pearl powder on antioxidant status in a randomized placebo-controlled trial,*" 26 J Food & Drug Analysis Issue 1 (January 2018) 309-317 (https://www.sciencedirect.com/science/article/pii/S1021949817301011.)

Spirulina

Spirulina is a naturally occurring, blue green algae that contains vitamin E, selenium and tyrosine, which are all known for their powerful anti-aging effects. The antioxidants present in tyrosine eliminate free radicals and slow down the aging of skin cells. Spirulina is also a wonderful source of chlorophyll, which has cleansing properties, and it also helps your skin retain moisture, which is a major key to maintaining the appearance of smoother, hydrated skin. With its high content of calcium, iron, phosphorous and vitamins A, B-12 and E, Spirulina works over time to fight free radicals, purifying your system and thereby restoring your skin's vitality. Spirulina brings about faster cell turnover, which helps your skin heal faster. Increasing your skin's metabolism is a key to maintaining a consistent healthy glow, so you're naturally shedding those dry skin cells that make your skin appear sallow and dull.

*Spirulina* has the ability to modulate immune functions and exhibits anti-inflammatory properties by inhibiting the release of histamine by mast cells. Spirulina has demonstrated positive effects on inflammation, chronic fatigue, cholesterol, anti-cancer. C-phycocyanin (C-PC) is one of the major biliproteins of *Spirulina* with antioxidant and radical scavenging properties. C-PC, a selective cyclooxygenase-2 inhibitor, induces apoptosis in lipopolysaccharide-stimulated RAW 264.7 macrophages. It is also known to exhibit anti-inflammatory and anticancer properties. Karkos et al., "Spirulina in Clinical Practice: Evidence-Based Human Applications," Review Article, Evidence-Based Complementary and Alternative Medicine Vol. 2011, Article ID 531053, 4 pages (2011).

Spirulina is a unicellular blue-green alga rich in vitamins, minerals, pigments, proteins, polysaccharides, which indicates a high potential use in anti-aging cosmetic products as well as for skin protection. Clinical studies showed antioxidant potential, immediate benefits on the skin microrelief and hydration and skin compatibility of formulations containing *Spirulina* extract. Delsin S D, Mercurio D G, Fossa M M, Maia Campos PMBG, *Clinical Efficacy of Dermocosmetic Formulations Containing Spirulina Extract on Young and Mature Skin: Effects on the Skin Hydrolipidic Barrier and Structural Properties*, Clin Pharmacol Biopharm (2015) 4:144. doi:10.4172/2167-065X.1000144.

IMMULINA™ is a particular spirulina extract and the predominant active compounds are Braun-type lipoproteins that are useful for improving human immune function.

These lipoproteins are present at much greater levels than those found within commonly used immune enhancing botanicals such as echinacea and ginseng.

Scientific evidence suggests that IMMULINA™ helps to support a healthy immune system:

Clinical trials
- 11 healthy males were given 400 mg IMMULINA™ daily for 56 days
- 10 healthy individuals (7 male, 3 female) from North America given 400 mg IMMULINA™ for 7 days
- 12 healthy individuals (5 male, 7 female) from Denmark given 200 mg or 400 mg IMMULINA™ for 7 days Preclinical Trials
- Mouse model showed enhanced innate immune system
- Mice were given 10-12 mg/day IMMULINA™ as an oral dose Immunity
- TLR2 dependent process for Braun-type lipoprotein for enhanced innate immunity
- Age dependent temporary enhancement of adaptive immune response observed in individuals over 50
- May have a priming effect on adaptive immune responses related to effects on the innate immune system Active agents also include, in addition to those noted above, and again without limitation: Honey, particularly Manuka Honey, (honey when used is used generically, Manuka is a species of honey) Aloe, including whole Aloe juice, Aloe Barbadensis, Aloe extracts, and fractions, Spirulina/IMMULINA® extract, Alfalfa, Ascorbic Acid and derivatives, Tocopherols, Co-Enzyme Q10, Bilberry extract, D-Glycosamine, Eucalyptus Oil, Vitamin A, Acai, Acetyl-L-Carnitine, Activated Charcoal, Albizza Flower, Alanine, Amla, Arecca Nut Palm, Apple Pectin, Arbutin, Argenine, Ashwaganda, Astaxanthin, Astragalus Root, Avocado Oil, Vitamin B, B6, B12, Bacopa, Banana, Barley Grass, Basil, Bedda Nut, Beetroot, Beta Glucan, Biotin, Bilberry, Bishop's Weed, Black Currant, Black Cohosh, Blackberry, Blue Agave, Borage Oil, Broccoli, Bromelain, Burdock, Cabbage Palm Fern, Caffeine, Calcium, at least one Cannabinoid or derivative, including, without limitation, Cannabidiol (CBD), Cannabidolic Acid, Cannabigerolic Acid, Cannabigerol, Cannabigerolic Acid, Cannabichronic Acid, Cat's Claw, Chaste Tree, Chia, Tetrahydrocannabivarin, Cannabidivarin, Tetrahydrocannabinol, Delta 9 Hydroxy Tetrahydrocannabinol, and the like, L-Carnitine, Chamomile Flower, Carnitine, one or a mixture of Ceramides, Chlorella, Cinnamon, Carrot, Cassica, Chaga, Cherry, Chicory, Cinnamic Acid derivatives, Clay/Bentonite, Camellia, Citric Acid, Choline, Chlorella, Cocoa, Coconut Oil or fractions thereof, Coffee extracts, Coenzyme Q10, Collagen, Collard Greens, Coltsfoot, Copper, Cornsilk, Cranberry, Curcumin, Cycloastragenol, Dandelion extract, DHEA, Dill, Elagic Acid, Echinacea, lderberry, Elecampane, Evening Primrose Oil, Eleuthero, Ferulic Acid, Feverfew, Flaxseed and oil, Folate, Fluoride, Frankincense Oil, Garlic, Ginger, Ginkgo, Ginseng, Glucosamine, L-Glutamine, Glutathione, Goji extract, Goldenseal, Gotu Kola, Grapefruit, Grapefruit Pectin, Grapeseed extract, Green Tea Extract, Hawthorn, Hemp Seed, Hibiscus Flower, Holly Oak, Honeysuckle Flower extract, Hops, Horse Chestnut, Hydrangea Root, Immortelle, Iodine, Iron, Ixora, Jujube, Japanese Star Anise, Japana Roxa, Juniper Berry, Vitamin K, Kale, Kava, Keratin, *Lactobacillus rhamnosus* (GG or HN001), *Lactobacillus plantarum, Bifidobacterium infantus, Bacillus subtilis* (DE 111); *Lactobacillus acidophilus; Bacillus coagulans* (SNZ 1969); *Lactobacillus paracasei* (Lpc-37); *Bifidobacterium lactis* (HN 019), (Bi-07) or (Bi-04); and *Lactobacillus salivarius* (Ls-33); Lavender, Lemon, Lemon Peel, Lemon Balm, Licorice, Lion's Mane Mushroom, L-Arginine, L-Cysteine, L-Glutamine, L-Glutathione, L-Theanine, Lycopene, Lysine, Manganese, Maitake Mushroom, Magnesium, Mango, Mastic Gum, Marine Collagen, Melatonin, Milk Thistle, Molybdenum, Monk Fruit, Mulberry, Neem, Niacin, Niacinamide, Olive Fruit, Olive Leaf, Omega 3 Fatty Acids, Oolong, Oregano, Panthenol, Papaya, Panthenine, Pantothenic Acid, Parsley, Passionflower, Paullinia Cupana, Peach, Pear, Pearl Powder, Peelu, Peppermint, Persimmon, Psorolea, Polygonum (genus of plants in the buckwheat and knotweed family), Pomegranate, Poplar Bud, Prebiotic and Probiotic strains and blends, Propolis, Oiruam PLE, Pterocarpus Wood extract, Pycnogenol, Raspberry, Reishi Mushroom, Rhodiola, Rhubarb, Riboflavin, Rose Apple, Rose Hip, Rosemary, Saw Palmetto, Selenium, Skullcap, SOLIDENTI, Soy, Spearmint, Spinach, Strawberry, Styrax, Sausage Tree, shiake Mushroom, Shisandra Berry, Sichuan Pepper, Spinach, St. John's Wort, SOLIDENTI; (Rosemary, Chamomile, Tea, Sage, Centella, Licorice, Japanese Knotweed, Skullcap), Sunflower Shoot, Tapioca, Tea Tree Oil, Temulawak, Thiamin, Turmeric Root, Thyme, Uva Ursi, Valerian, Vanilla, Vitex, Wheatgrass, Wild Yam, Yerba Mate, and Zinc. Various derivatives of these active agents and specific fractions or extracts obtained from the foregoing are hereby contemplated. For example, various fractions of aloe can be used in addition to or instead if a "whole" juice or extract. (See e.g. U.S. Pat. No. 7,196,072.) And salts, ethers, esters, and other derivatives of recited ingredients are contemplated. L-ascorbic acid could be used, but so too could an ascorbate salt or ester, for example. These and other active agents, and amounts that can be used for dosing, are discussed in the ABC Clinical Guide to Herbs, edited by Mark Blumenthal and published in 2003 by the American Botanical Council (PO Box 144354, Austin, Texas 78714-4345) (www.herbalgram.org) (ISBN 1-58890-157-2), the text of which that identifies natural ingredients, their uses, the amounts used, and clinical studies involving them, are hereby incorporated by reference.

That said, the action of botanicals is known to range from mild to powerful (potent). A botanical with mild action may have subtle effects. Chamomile and peppermint, both mild botanicals, are usually taken as teas to aid digestion and are generally considered safe for self-administration. Some mild botanicals may have to be taken for weeks or months before their full effects are achieved. For example, valerian may be effective as a sleep aid after 14 days of use but it is rarely effective after just one dose. In contrast a powerful botanical produces a fast result. Kava, as one example, is reported to have an immediate and powerful action affecting anxiety and muscle relaxation. Accordingly, the amount of each active agent will vary with a number of factors, including the potency of the active agent, how many active agents will be used and their properties and objectives, the objective of formulation, the amount of toothpaste to be used in any one use/administration (e.g., dose), the number of times that a formulation will be used in a day, and the like. It can also depend upon the form of the active agent. For example, botanicals are sold in many forms: as fresh or dried products; liquid or solid extracts; tablets, capsules, powders; tea bags; and other forms. The amount included can vary depending upon the form of the active. However, in general, the amount of each active to be delivered should range from about 1 microgram to 10 grams per toothpaste application (e.g., per dose) and in another embodiment, from about 1 micrograms to about 1000 milligrams. In still another embodiment, the amount of each active agent will range from about 1 microgram to about to about 500 milligrams and in still another from about 10 milligrams to about 500 milligrams. In another embodiment, the total amount of all Active Agents meant to influence the skin of the user, combined per dose (single use or application of a toothpaste of the invention) ranges from about 0.1 μg to about 10 g, in a further embodiment from about 1 μg to about 1 g and in still a further embodiment, the total amount of such actives per dose should range from about 1 μg to about 500 mg and in yet another embodiment, from about 1 mg to about 500 mg Alternatively, the amount of total Active Agents supporting the health, well-being and/or appearance of a user's skin through the application to the oral cavity of a single dose of a toothpaste in accordance with the present invention, expressed in weight percent (wt %) can range from about 0.1 to about 20 wt %, and in another embodiment, from about 0.1 to about 10 wt % and in still a further embodiment, from about 0.1 to about 5 wt % based on the total weight of each dose of toothpaste which is intended to be applied.

The amounts of active ingredients as recited above, and in this disclosure in general, can be determined by direct measurement of the content in a dose of the intended amount of toothpaste or by considering the total volume of toothpaste and dividing it by the number of expected doses and calculating the amount of one or all of the active agent(s) that should be assumed to be in each dose, making the assumption that that each active agent is evenly distribute throughout the toothpaste formulation. This is true for an individual tube, or a manufacturing batch.

Finally, merely as representative of the size of individual doses of toothpaste formulations that can be used in certain situations, 0.125 gm of toothpaste can be used for children less than 3 years of age, pea sized (0.25 gm) for children aged 3 to 6 years, "half head" (0.5 gm) for age 6+ and a "full head" (1.0 gm) can be used for adults. Obviously this can vary widely. Thus a "dose," the amount of toothpaste in accordance with the invention used in each application, can vary generally between about 0.25 and about 2.5 grams.

Particle size of active agents can often play a role in the organoleptic properties of the toothpaste. Larger particles tend to be gritty and uncomfortable. However, if the amount of active agent delivered is relatively small, it may be possible to use larger particle sizes. As the amount of particles increases, however, the particle size of solid active agents that do not dissolve into the formulation generally needs to be reduced. In general, the average particle size of the particular active agents useful in accordance with the present invention, as measured by a laser light scattering technique and measured by mass, is less than about 100 micrograms. Active ingredients may also be in the form of a liquid or suspended in a liquid although this may create additional formulation issues.

In addition to the active agents, other ingredients that may be used in the formulations of the invention include those conventionally used in toothpaste such as toothpaste bases, abrasives, carriers, flavorings, colorings, stabilizers, preservatives, viscosity enhancers, pH adjusters, sparkles, gelling agents, effervescent agents, thickeners, humectants, desensitizing agents, sensitivity agents, whitening agents, mucosal adhesives, bad breath agents, gingivitis agents, astringents, oxidizing agents, and the like. These may be used in the manner and quantity generally known in the art.

Any toothpaste formulation or base known in the art may be used. Ideally, the toothpaste base will facilitate maintaining the health of the teeth, gums, and other structures within the oral cavity. It will also provide for an acceptable carrier for the active ingredients of the invention. The formulation or base must be susceptible of being swallowed without harm to its user and is ideally inert with regard to the active agents to be delivered. It will allow for and facilitate a homogeneous distribution of the active agents as well.

Known formulation ingredients include: for example, abrasives which may used in conventional amounts such as 20-80%, or more, of the formulations. Abrasives include, without limitation, particles of aluminum hydroxide ($Al(OH)_3$), alumina trihydrate and/or dehydrate; calcium pyrophosphate; magnesium trisilicate; insoluble sodium metophosphate, bicarbonates such as sodium bicarbonate, calcium carbonate ($CaCO_3$), dibasic calcium phosphate, calcium hydrogen phosphates, silicas including dental silica thickener, zeolites, liponite, laponite, hydroxyapatite ($Cas(PO_4)_3OH$), fluoroapatite, and mica. Other ingredients that may be used include, for example: magnesium aluminum silicates (such as VEEGUM) and clays including bentonite clay (such as VANATURAL), both from Vanderbilt Minerals, LLC, 33 Winfield Street, PO Box 5150, Norwalk, CT 06856-5150; vanderbiltminerals.com. These and other ingredients, instead of or in addition to, their abrasive function, may act as thickening agents and/or viscosity enhancers or binders. In addition to bentonite, other clays, gums such as xanthan gum, celluloses such as carboxymethyl cellulose and hydroxyethyl cellulose, in conventional amounts (such as about 0.5 to about 10%) may also be used.

Whitening agents may be used including, without limitation: alumina, phosphates such as sodium hexametaphosphate, charcoal, and polyvinylpyrrolidone (PVP).

Surfactants may also be used in such formulations in a conventional amount. These can include sodium lauryl sulfate, sodium auroyl sarcosinate, carryloyl, caproyl, cocoamidopropyl betain, methyl glucamide and glycolipids.

Antibacterial agents such as Triclosan, zinc chloride, zinc citrate may be used also in conventional amounts and often less than 5% wt/wt (0.1 to 5%) and indeed less than 1% wt/wt. Where xylitol is used as a sweetener, if more than 2% is used, it can also act as an antimicrobial agent. Preservatives such as phenoxyethanol may also be used in conventional amounts, usually less than 2% wt/wt (0.1 to 2%) and indeed often less than 1%.

Humectants may be used in conventional amounts. These include, for example, 10-50% of sorbitol (also a sweetener) or glycerin.

Sweeteners in accordance with the invention can be natural or artificial, but are not sugars in the conventional sense. So glucose, sucrose and fructose are generally not included, or if included only included in relatively small amounts. One category of useful "natural" sweeteners are sugar alcohols including, for example, xylitol, arabitol, ribitol, mannitol, isomalt, lactitol, maltitol, sorbitol, erythritol, and monk fruit. Not only can these provide sweetness, they also can often adjust and enhance viscosity. "Artificial" sweeteners may be used in place of some or all of the other sweeteners. These include saccharine, aspartame, *Stevia*, sucralose and derivatives (SPLENDA). Honey may also be used. The total amount of these sweeteners may vary widely with the number and type used, their relative sweetness, the flavor to be used in the formulations, and the degree of taste masking that may be required. The amount of sweeteners may vary from about 0.25% (usually when using artificial sweeteners) up to as much as about 50% wt/wt. But generally, the total amount of sweeteners, particularly when using natural sweeteners such as sugar alcohols ranges from between about 5 to about 40% wt/wt. Desensitizing agents such as potassium nitrate may also be used in amounts of about 5% or more.

The most common toothpaste flavors are spearmint, peppermint, wintergreen, cinnamon, bourbon, rye, anise, clove, caraway, coriander, eucalyptus, nutmeg, menthol and thyme. There is a growing trend in fun flavors, like vanilla, strawberry, bubblegum and luxury flavors like jasmine. Additionally, addressing functional oral care flavors means addressing consumer's demands to feel good and to instill confidence and well-being. Flavors include all commercially available flavors as well as custom formulations. These include, all FDA flavors (https://www.fda.gov/food/food-ingredients-packaging/overview-food-ingredients-additives-colors) without limitation, all flavors listed on Fema Flavor Database, e.g., FD&C Yellow No. 6 and Shttps://www.femaflavor.org/flavor-library/search?fulltext=&synonyms=1, and Superscent Database, http://bioinf-applied.charite.de/superscent/https://www.ncbi.nlm.nih.gov/pmc/articles/PMC2686498/.

Colors include all commercially available colors approved by the FDA, as well as custom colors. (https://www.fda.gov/industry/color-additive-inventories/summary-color-additives-use-united-states-foods-drugs-cosmetics-and-medical-devices) These can include, for example, about 0.25 to about 1% of coloring agents such as titanium dioxide, zinc oxide and known food colorings and dyes.

Other ingredients which may be used in their conventional amounts include 1,2 propylene glycol, polyethylene glycol, strontium chloride, potassium nitrate, arginine, calcium sodium phosphosilicate, diethylene glycol, stannousions, stannous fluoride, papsin, dimethicone sodium fluoride, sodium monofluorophosphate, potassium nitrate, strontium chloride, potassium citrate, pyrophosphates, hydrogen peroxide, or materials that can generate a peroxide in situ.

Manifestly, there are many toothpaste formulations that can serve as a delivery vehicle for the active agents and toothpaste formulations in accordance with the invention. Some exemplary formulations can include those components shown in Table 1:

TABLE 1

| Ingredient | Composition (weight %) | Exemplary Materials | Purpose |
|---|---|---|---|
| Humectant | 20-50% | Sorbitol, glycerin | Maintains moisture content |
| Water | 5-50% | Deionized water | Suspension agent |
| Abrasive | 1-20% | Calcium carbonate /dibasic calcium phosphate dihydrate/ hydrated alumina/ hydrated silica/sodium bicarbonate or mixtures of abrasives | Removal of plaque/stain/ polish tooth surface |
| Sweetener | 0.25-10% | Sodium Saccharine, Xylitol, Erythritol | Adds sweetness |
| Surfactant | 1-2% | Sodium lauryl sulfate/ sodium lauroyl sarcosinate | Creates foam and aids debris removal |
| Binders (includes Thickeners and Rheology modifying agents) | 0.5-20% | Gums such as Xanthan gum, celluloses such as carboxy methylcellulose and hydroxy ethylcellulose, Clays (such as Smectite clays including VEEGUM), silicon dioxide and related silicates (such as Zeodent (Zeodent 167)) | Creates a uniform composition of desired consistency and viscosity |
| Remineralizing agent | 1-20% | Nano-hydroxyapatite (calcium hydroxyphosphate) (nanoHAP) | Restorative of enamel and treatment for tooth sensitivity |
| Colorants | 0.25-1% | Titanium dioxide, zinc oxide, food coloring | Makes the toothpaste a certain color |
| Preservatives | 0.5-1% | Phenoxyethanol, sodium benzoate, parabins | Prevent microbial growth |
| Flavor | 0.5-1% | Peppermint, spearmint, wintergreen, menthol | flavor |

Toothpastes, as currently known, have been around for more than a century. The Colgate Palmolive Company suggests that it made its first toothpaste in a collapsible tube in 1896 called Colgate Ribbon Dental Cream. And in 1934, in the U.S., toothpaste standards were developed by the American Dental Association's counsel on dental therapeutics. During the middle of the 20th century, fluoride was introduced.

There are many variations on the form of toothpaste but, in general as noted earlier, they often contain one or more of binders, abrasives, sudsers, humectants, flavors, sweeteners, fluorides, tooth whiteners, preservatives, water, surfactants, desensitizers, colors, and active agents. Often these materials are charged to a mixing vessel or vat. The vat can allow for mixing, heating, cooling, and/or vacuum to be applied. In some instances, the liquid ingredient such as water and/or glycerin are added first to help dissolve and disperse other ingredients as they are added under mixing and/or agitation. In some instances, certain ingredients need to be separately dissolved and added as a solution or dispersion for stability or dispersibility purposes and then the material is mixed until a paste is formed. The amount of mixing will depend often upon the form of the toothpaste and the ingredients used. For example, if a gel is to be formed, the amount of mixing required may be less or more than certain traditional paste forms. If the system is primarily aqueous and non-compatible materials are intended to be used or delivered, it may be necessary to form an emulsion or microemulsion and the degree of mixing used would be consistent with that objective. The resulting toothpaste formulation can then be loaded into a container such as a tube or a pump. High shear mixing techniques wherein the material in the vat are mixed under vacuum are also well-known. In general the preparation of toothpastes and the compositions that can be used (aside from the active ingredients disclosed herein) can include, without limitation, those disclosed in U.S. Pat. Nos. 3,980,767; 3,996,863; 4,024,239 (Example 1); U.S. Pat. Nos. 4,328,205; 4,358,437; 4,839,156 (Examples 1 and 2); 6,946,010 (Example 2); 8,221,724 (Col.14 ln.16 through Col.31 ln.10); and 8,940,278 (Col.7 ln.1 through Col.10 ln.3); all of which are incorporated herein by reference.

Types of Toothpastes

Toothpastes of the invention are generally formulated specifically to address a particular aspect of skin health or well-being and/or appearance. These include, without limitation, formulations specifically designed to address: skin aging, signs of aging, skin irregularities, skin elasticity, skin vitality, collagen generation, hydration, the appearance of fine lines and wrinkles, skin whitening, liver spots, skin softness, sagging, drooping skin, dull skin tone, lines, wrinkles, crows feet, loss of volume, plumpness, loss of elasticity and firmness, laugh lines, puffy eyes, droopy eyes, scaly, rough skin, patchy skin, open pores, dry, cracked skin, discolored patches of skin, loss of pigment, skin radiance, luminosity, brightening; peeling skin, age spots, sunburn, sunspots, decollete wrinkles, crepey skin, acne, psoriasis, rosacea and rash. The active agents contained in the formulations and methods of the invention can address one or more of these conditions or their symptoms and/or appearance.

Some exemplary combinations of active agents that can be used in toothpaste formulations of the invention to support specific aspects of the health, well-being, and/or appearance of skin include, without limitation:

Formulations to support at least one of elasticity, firming, hydration, texture, nutrition, radiance, immuno-stimulatory properties, and/or anti-inflammatory properties ("BASIC AM"—if with ascorbic acid "BASIC AM+C," "BASIC with C" or "BASIC PLUS C") include one or more of: Aloe barbadensis, bilberry, coenzyme Q10, Vitamin E, glucosamine, honey such as Manuka honey, spirulina/IMMULINA, hyaluronic acid, Vitamin C, SOLIDENTI; *Centella asiatica* extract, *Polygonum cuspidatum* root extract, *Scutellaria baicalensis* root extract, *Camellia sinensis* leaf extract, *Glycyrrhiza glabra*(licorice) root extract, *Chamomilla recutita*(matricaria) flower extract, *Chamomilla recutita*. Flavors: wildmint, newmint, herbal blends, new concept blends, citrus blends, fruit blends, spice blends, floral blends and seasonal blends, i.e. holiday peppermint. All common flavors, such as spearmint, peppermint, wintergreen, cinnamon, bourbon, rye, clove, caraway, coriander, eucalyptus, nutmeg, menthol and thyme. Including, and not limited to, all FDA approved flavors.

One particular formulation includes: Sorbitol, Aqua, Glycerin, Xylitol, Calcium Carbonate, Hydrated Silica, Magnesium Aluminum Silicate, honey such as Manuka Honey, *Spirulina platensis* Extract, Nano-Hydroxyapatite, *Aloe barbadensis* Leaf Extract, Tocopheryl Acetate, Glucosamine, Ubiquinone, L-Ascorbic Acid, Sodium Hyaluronate, *Vaccinium myrtillus* Fruit/Leaf Extract, Propandial, *Centella asiatica* Extract, *Polygonum cuspidatum* Root Extract, *Scutellaria baicalensis* Root Extract, *Camellia sinensis* Leaf Extract, *Glycyrrhiza glabra* (Licorice) Root Extract, *Chamomilla recutita* (Matricaria) Flower Extract, *Chamomilla recutita* (Matricaria) Flower Extract, *Salvia officinalis* (Sage) Extract, Xanthan Gum, Natural Mint Aroma, Potassium Chloride.

Formulations for use in the evening (including, without limitation, "PM," "BASIC PM," and if with ascorbic acid "PM+C," "BASIC PM+C," "BASIC PM (elasticity)" and "BASIC PM (repair)" and various permutations of these) to support at least one of skin aging; signs of aging; skin irregularities; skin elasticity; collagen generation; hydration; skin nutrition; appearance of fine lines and wrinkles; skin discoloration; elasticity; skin whitening; liver or age spots; skin softness; skin suppleness; skin firmness; skin sagging; skin drooping; dull skin tone; skin radiance; lines; wrinkles; crows feet; loss of volume; plumpness; luminosity; vitality; laugh lines; puffy skin around the eyes; discolored skin around the eyes; droopy eyes; scaly skin; rough skin; chapped skin; patchy skin; open pores in skin; cracked skin; dry skin; peeling skin; sunburned skin; sunspots; decollete wrinkles; crepey skin; acne; psoriasis; rosacea; rash; cell renewal; restore; replenishment; collagen production; immuno-stimulatory properties, and/or anti-inflammatory properties include one or more of: Vitamin A, aloe barbadensis, chamomile flower, coenzyme Q10, Vitamin E, glucosamine, hyaluronic acid, honey such as Manuka honey, passionflower, spirulina/IMMULINA, zinc and SOLIDENTI; *Centella asiatica* extract, *Polygonum cuspidatum* root extract, *Scutellaria baicalensis* root extract, *Camellia sinensis* leaf extract, *Glycyrrhiza glabra* (licorice) root extract, *Chamomilla recutita* (matricaria) flower extract, *Chamomilla recutita*. These formulations may also include one or more active agents promoting restfulness including, without limitation: melatonin, skullcap, poria, albizza flower, jujube, polygonum, Valerian, Lavender, Hop, Chamomile, St Johns Wort, Rosemary, Valerian, Hops, Blue Vervain, Passionflower, Wild Lettuce, Hawthorn, lemon balm, goji and green tea extract. Flavors: wildmint, newmint, followed by others i.e. custom mint blends, herbal blends, new concept blends, citrus mint blends, fruit blends, spice blends and seasonal blends. All common flavors, such as spearmint, peppermint, wintergreen, cinnamon, bourbon, rye, clove, caraway, coriander, eucalyptus, nutmeg, menthol and thyme. Including, and not limited to, all FDA approved flavors.

"BOOST" formulations to support at least one of clarity, vitality, pick me up with antioxidant coffee extracts/refresh, restore, rejuvenate, immuno-stimulatory properties, and/or anti-inflammatory properties include one or more of: Aloe barbadensis, bilberry, coenzyme Q10, Vitamin C, coffee extracts, Vitamin E, glucosamine, honey such as Manuka honey, spirulina/IMMULINA, hyaluronic acid and SOLIDENTI; *Centella asiatica* extract, *Polygonum cuspidatum* root extract, *Scutellaria baicalensis* root extract, *Camellia sinensis* leaf extract, *Glycyrrhiza glabra* (licorice) root extract, *Chamomilla recutita* (matricaria) flower extract, *Chamomilla recutita*. These formulations may also contain one or more of: astragalus, rhodiola, reishi, caffeine, coffee extract and other agents. Flavors: coffeemint, wildmint, custom mint blends, herbal blends, new concept blends, citrus mint blends, fruit blends, floral blends, spice blends and seasonal blends. All common flavors, such as spearmint, peppermint, wintergreen, cinnamon, bourbon, rye, clove, caraway, coriander, eucalyptus, nutmeg, menthol and thyme. Including, and not limited to, all FDA approved flavors.

Formulations to support whitening ("WHITENING") and at least one of elasticity, firming, nourishment, hydration, whitening, immuno-stimulatory properties, anti-inflammatory properties include one or more of: Activated charcoal, aloe barbadensis, clay/bentonite, coenzyme Q10, Vitamin E, honey such as Manuka honey, spirulina/IMMULINA, glucosamine, hyaluronic acid and SOLIDENTI; *Centella asiatica* extract, *Polygonum cuspidatum* root extract, *Scutellaria baicalensis* root extract, *Camellia sinensis* leaf extract, *Glycyrrhiza glabra* (licorice) root extract, *Chamomilla recutita* (matricaria) flower extract, *Chamomilla recutita*. These formulations may also contain one or more of: charcoal/bamboo powder and grapefruit seed extract. Flavors: wildmint, citrusmint, custom mint blends, herbal blends, new concept blends, citrus mint blends, fruit blends, floral blends, spice blends and seasonal blends. All common flavors, such as spearmint, peppermint, wintergreen, cinnamon, bourbon, rye, clove, caraway, coriander, eucalyptus, nutmeg, menthol and thyme. Including, and not limited to, all FDA approved flavors.

Formulations providing anti-wrinkle properties ("ANTI-WRINKLE") and one or more of reduction in the appearance of fine lines and wrinkles, immuno-stimulatory properties, and/or anti-inflammatory properties include one or more of: Vitamin A, aloe barbadensis, Vitamin C/ascorbic acid, coenzyme Q10, green tea, hyaluronic acid, honey such as Manuka honey, rose hip, spirulina/IMMULINA and SOL- IDENTI; *Centella asiatica* extract, *Polygonum cuspidatum* root extract, *Scutellaria baicalensis* root extract, *Camellia sinensis* leaf extract, *Glycyrrhiza glabra* (licorice) root extract, *Chamomilla recutita* (matricaria) flower extract, *Chamomilla recutita*. These formulations may also include: pearl powder, polypodium leucotomos, pomegranate extracts, collagen, cycloastragenol, nicotinamide riboside, nicotinamide mononucleotide, turmeric, protein, Vitamin D, Vitamin K, ALA, grape seed extract, collagen peptide, crocin, astragalus, lutein, resveratrol, ceramides, ferulic acid, sunflower shoot and propolis. Flavors: wildmint, newmint, custom mint blends, herbal blends, new concept blends, citrus blends, fruit blends, floral blends, spice blends and seasonal blends. All common flavors, such as spearmint, peppermint, wintergreen, cinnamon, bourbon, rye, clove, caraway, coriander, eucalyptus, nutmeg, menthol and thyme. Including, and not limited to, all FDA approved flavors.

"STRESS/BLISS" formulations to support at least one of skin protection, skin repair and skin conditions caused by the negative effects of stress on the skin or other causes, immuno-stimulatory properties, and/or anti-inflammatory properties may include one or more of: aloe barbadensis, ashwanganda, Vitamin E, honey such as Manuka Honey, spirulina/IMMULINA, reishi mushroom, rhodiola rosacea, ashwaganda, passionflower, sunflower shoot, turmeric and SOLIDENTI; *Centella asiatica* extract, *Polygonum cuspidatum* root extract, *Scutellaria baicalensis* root extract, *Camellia sinensis* leaf extract, *Glycyrrhiza glabra* (licorice) root extract, *Chamomilla recutita* (matricaria) flower extract, chamomilla recutita. These formulations may also include a cannabinoid. Flavors: wildmint, newmint, custom mint blends, herbal blends, new concept blends, citrus blends, fruit blends, floral blends, spice blends and seasonal blends. All common flavors, such as spearmint, peppermint, wintergreen, cinnamon, bourbon, rye, clove, caraway, coriander, eucalyptus, nutmeg, menthol and thyme. Including, and not limited to, all FDA approved flavors.

"SUN PROTECTION" formulations supporting skin protection and repairing and addressing the negative effects of sun, immuno-stimulatory properties, and/or anti-inflammatory properties may include one or more of: aloe barbadensis, Vitamin C/ascorbic acid, coenzyme Q10, Vitamin E, green tea, passionflower, rose hip, spirulina/IMMULINA, turmeric, zinc and SOLIDENTI; *Centella asiatica* extract, *Polygonum cuspidatum* root extract, *Scutellaria baicalensis* root extract, *Camellia sinensis* leaf extract, *Glycyrrhiza glabra* (licorice) root extract, *Chamomilla recutita* (matricaria) flower extract, *Chamomilla recutita*. These formulations may contain pomegranate, lutein, polypodium, grapefruit seed extract, or cinnamic acid derivatives. Flavors: citrusmint, wildmint, followed by others i.e. custom mint blends, herbal blends, new concept blends, citrus mint blends, fruit blends, spice blends, custom mint blends, herbal blends, new concept blends, citrus mint blends, fruit blends, floral blends, spice blends and seasonal blends. All common flavors, such as spearmint, peppermint, wintergreen, cinnamon, bourbon, rye, clove, caraway, coriander, eucalyptus, nutmeg, menthol and thyme. Including, and not limited to, all FDA approved flavors.

"ACNE/PSORIASIS" formulations which support various aspects of skin health including, for example, assisting in treating acne/psoriasis, immuno-stimulatory properties, and/or anti-inflammatory properties may include one or more of: Vitamin A, aloe barbadensis, astaxanthin, Vitamin D, Vitamin E, polypodium leucotomos, spirulina/IMMULINA, tea tree oil, gotu kola, flaxseed, grapefruit seed extract, pearl powder and SOLIDENTI; *Centella asiatica* extract, *Polygonum cuspidatum* root extract, *Scutellaria baicalensis* root extract, *Camellia sinensis* leaf extract, *Glycyrrhiza glabra* (licorice) root extract, *Chamomilla recutita* (matricaria) flower extract, *Chamomilla recutita*. These formulations may also include a cannabinoid. Flavors: wildmint, custom mint blends, herbal blends, new concept blends, citrus mint blends, fruit blends, spice blends, herbal blends, new concept blends, citrus mint blends, fruit blends, floral blends, spice blends and seasonal blends. All common flavors, such as spearmint, peppermint, wintergreen, cinnamon, bourbon, rye, clove, caraway, coriander, eucalyptus, nutmeg, menthol and thyme. Including, and not limited to, all FDA approved flavors.

Formulations of the invention may also be designed to address the needs and nutritional requirements of certain specific groups of people, such as those who prefer a vegan lifestyle. Designing formulations for groups such as these is all about supplementing their skin needs in view of their diet. A basic vegan formulation ("VEGAN" or "VEGAN+C") that supports one or more of elasticity, firming, moisturizing for vegan diets, immuno-stimulatory properties, and/or anti-inflammatory properties may include one or more of: aloe barbadensis, coenzyme Q10, Vitamin E, Vitamin D, honey such as Manuka honey, spirulina/IMMULINA, SOLIDENTI; *Centella asiatica* extract, *Polygonum cuspidatum* root extract, *Scutellaria baicalensis* root extract, *Camellia sinensis* leaf extract, *Glycyrrhiza glabra* (licorice) root extract, *Chamomilla recutita* (matricaria) flower extract, *Chamomilla recutita*, hyaluronic acid, Vitamin C, iron, Vitamin K, Vitamin B12, Vitamin B complex, magnesium. Flavors: wildmint, newmint, custom mint blends, herbal blends, new concept blends, citrus mint blends, fruit blends, spice blends, herbal blends, new concept blends, citrus mint blends, fruit blends, floral blends, spice blends and seasonal blends. All common flavors, such as spearmint, peppermint, wintergreen, cinnamon, bourbon, rye, clove, caraway, coriander, eucalyptus, nutmeg, menthol and thyme. Including, and not limited to, all FDA approved flavors.

A "VEGAN PM" formulation that supports one or more of elasticity, firming, moisturizing for vegan diets, immuno-stimulatory properties, and/or anti-inflammatory properties may include one or more of: aloe barbadensis, coenzyme Q10, Vitamin E, Vitamin D, honey such as Manuka honey, spirulina/IMMULINA, hyaluronic acid, Vitamin C, iron, Vitamin K, Vitamin B12, Vitamin B complex, magnesium, chamomile, passionflower, astragalus, and zinc. These formulations may also contain one or more of melatonin, skullcap, poria, albizza flower, jujube, polygonum, valerian, lavender, hop, chamomile, St Johns wort, rosemary, hops, blue vervain, passionflower, wild lettuce, hawthorn, lemon balm, goji, green tea extract and other agents. Flavors: wildmint, newmint, herbalmint, custom mint blends, herbal blends, new concept blends, citrus mint blends, fruit blends, spice blends, herbal blends, new concept blends, citrus mint blends, fruit blends, floral blends, spice blends and seasonal blends. All common flavors, such as spearmint, peppermint, wintergreen, cinnamon, bourbon, rye, clove, caraway, coriander, eucalyptus, nutmeg, menthol and thyme. Including, and not limited to, all FDA approved flavors.

Another group whose skin health needs may be underappreciated and served are menopausal and perimenopausal people, particularly women. As their bodies and their chemistries transition during this period, the health, wellness, and nutritional needs of their skin may change and would benefit from formulation modifications. Formulations to help address the effects of menopause on the skin ("MENOPAUSE") can include one or more of: aloe barbadensis, Vitamin C, coenzyme Q10, evening primrose oil, licorice root, ginseng, hyaluronic acid, red clover, rose hip, skullcap, spirulina/IMMULNA and SOLIDENTI; *Centella asiatica* extract, *Polygonum cuspidatum* root extract, *Scutellaria baicalensis* root extract, *Camellia sinensis* leaf extract, *Glycyrrhiza glabra* (licorice) root extract, *Chamomilla recutita* (matricaria) flower extract, *Chamomilla recutita*. Flavors: wildmint, newmint, custom mint blends, herbal blends, new concept blends, citrus mint blends, fruit blends, spice blends, herbal blends, new concept blends, citrus mint blends, fruit blends, floral blends, spice blends and seasonal blends. All common flavors, such as spearmint, peppermint, wintergreen, cinnamon, bourbon, rye, clove, caraway, coriander, eucalyptus, nutmeg, menthol and thyme. Including, and not limited to all FDA approved flavors.

Formulations to support hair/nails ("HAIR/NAILS"), immuno-stimulatory properties, and/or anti-inflammatory properties can include one or more of: Aloe barbadensis, Vitamin B, biotin, Vitamin C/ascorbic acid, coenzyme Q10, Vitamin E, hyaluronic acid, honey such as Manuka honey, spirulina/IMMULINA and SOLIDENTI; *Centella asiatica* extract, *Polygonum cuspidatum* root extract, *Scutellaria baicalensis* root extract, *Camellia sinensis* leaf extract, *Glycyrrhiza glabra* (licorice) root extract, *Chamomilla recutita* (matricaria) flower extract, *Chamomilla recutita*. These formulations may also contain polygonum and other agents. Flavors: wildmint, newmint, custom mint blends, herbal blends, new concept blends, citrus mint blends, fruit blends, spice blends, herbal blends, new concept blends, citrus mint blends, fruit blends, floral blends, spice blends and seasonal blends. All common flavors, such as spearmint, peppermint, wintergreen, cinnamon, bourbon, rye, clove, caraway, coriander, eucalyptus, nutmeg, menthol and thyme. Including, and not limited to, all FDA approved flavors.

Any of the formulations described herein can be produced with fluoride. For example, one can provide BASIC AM/fluoride formulations to support one or more of elasticity, firming, nourishment, hydration, radiance, glow can include one or more of: Aloe barbadensis, bilberry, coenzyme Q10, Vitamin E, glucosamine, honey such as Manuka Honey, spirulina/IMMULINA and SOLIDENTI; *Centella asiatica* extract, *Polygonum cuspidatum* root extract, *Scutellaria baicalensis* root extract, *Camellia sinensis* leaf extract, *Glycyrrhiza glabra* (licorice) root extract, *Chamomilla recutita* (matricaria) flower extract, *Chamomilla recutita*. These formulations may also contain: hyaluronic acid, Vitamin C, and/or other agents. These may include various forms of fluoride. Flavors: wildmint, newmint, followed by others i.e. custom mint blends, herbal blends, new concept blends, citrus blends, fruit blends, floral blends, spice blends and seasonal blends, i.e. Holiday peppermint, including, and not limited to, all FDA approved flavors.

"DETOX/CELLULITE" formulations that support immuno-stimulatory properties, anti-inflammatory properties may include one or more of: aloe barbadensis, Vitamin E, flaxseed, gotu kola, horse chestnut, hyaluronic acid, licorice root, honey such as Manuka Honey, spirulina/IMMULINA, tea tree oil. Flavors: citrusmint, wildmint, followed by others i.e. custom mint blends, herbal blends, new concept blends, citrus mint blends, fruit blends, spice blends i.e. custom mint blends, herbal blends, new concept blends, citrus mint blends, fruit blends, floral blends, spice blends, custom mint blends, herbal blends, new concept blends, citrus mint blends, fruit blends, spice blends, herbal blends, new concept blends, citrus mint blends, fruit blends, floral blends, spice blends and seasonal blends. All common flavors, such as spearmint, peppermint, wintergreen, cinnamon, bourbon, rye, clove, caraway, coriander, eucalyptus, nutmeg, menthol and thyme. Including, and not limited to, all FDA approved flavors.

Formulations for men which address male skin concerns ("MEN") including one or more of irritation, sun damage, acne, immuno-stimulatory properties, anti-inflammatory properties may include one or more of: Vitamin A, aloe barbadensis, astaxanthin, Vitamin C/ascorbic acid, coenzyme Q10, Vitamin E, polypodium leucotomos, spirulina/IMMULINA, green tea, zinc. These formulations may also contain rose hip, turmeric, passionflower, pomegranate and other agents. Flavors: wildmint, newmint, spice blend, followed by others i.e. custom mint blends, herbal blends, new concept blends, citrus blends, fruit blends, spice blends and seasonal blends, i.e. holiday peppermint. All common flavors, such as spearmint, peppermint, wintergreen, cinnamon, bourbon, rye, clove, caraway, coriander, eucalyptus, nutmeg, menthol and thyme. Including, and not limited to, all FDA approved flavors.

Probiotic

Not surprisingly, digestive problems can impact multiple systems and organ in the body and the skin is one of them. Thus another type of toothpaste formulation in accordance with the present invention can address digestive, microbiome, prebiotic and/or probiotic issues. These can be provides alone, or as with all of the forgoing formulations, in combination with actives agents intended to more directly support some specific aspect of skin health, well-being and/or appearance. Such formulations may include, without limitation, one or more of: Aloe barbadensis, bilberry CoQ10, tocopherol, glucosamine, honey, and spirulina. They may also include prebiotic and probiotic strains such as, without limitation, *Lactobacillus plantarum, Lactobacillus rhamnosus* (GG or HN001), *Lactobacillus plantarum, Bifidobacterium infantus, Bacillus subtilis* (DE 111); *Lactobacillus acidophilus; Bacillus coagulans* (SNZ 1969); *Lactobacillus paracasei* (Lpc-37); *Bifidobacterium lactis* (HN 019), (Bi-07) or (Bi-04); and *Lactobacillus salivarius* (Ls-33) Other active agents that can be used include, again without limitation: hyaluronic acid (HA) and ascorbic acid.

In addition to formulating toothpaste formulations to address specific conditions, symptoms, and the like, another aspect of the invention is a toothpaste designed and formulated for "use at a particular time of day." This and other similar phrases, indicate a formulation such as, without limitation, one designed to be used in the morning before breakfast, morning after breakfast, lunchtime, just before or just after an evening meal, at or after a coffee/tea break, at a time of low energy to provide invigoration, following social drinking or smoking, and the like. Some or all of these could be a toothpaste in accordance with the present invention that supports or sustains the health, well-being, and/or appearance of skin or other health-related benefit. A toothpaste designed only for use at night, such as just prior to going to bed, is also an embodiment of this aspect of the invention. These night-time formulations can, but need not, include active agents that support calming and restfulness and/or support or sustain the health, well-being, and/or appearance of skin. Some active ingredients may be better absorbed by the body when in a fasted or fed state. Therefore, one or more of the toothpastes of the invention can be specifically designed based on food intake or the timing in which foods are or are not ingested. For example, in the morning generally after one has ingested food, or evening generally when one is in a fasted state, while others provided for following meals.

As noted one possible time-related formulation is specific toothpastes for use at night. Night time formulations can be designed based on the anticipated activity of the active agents to be used during the sleep cycle on the health, well-being, and/or appearance of skin, based on the coadministration of agents which can relax the user or improve a user's ability to sleep or rest, or a combination of both. Active agents that may be included to promote restfulness include, without limitation: chamomile flower, passionflower, lavender, melatonin, L-tryptophan, skullcap, poria, albizza flower, jujube, polygonum, valerian, lavender, hop, chamomile, st. johns wort, rosemary, valerian, blue vervain, passionflower, wild lettuce, hawthorn, lemon balm, goji and green tea extract. Indeed, one particular PM toothpaste formulation that can promote restfulness and anti-aging benefits to the skin includes one or more of: chamomile flower, passionflower, melatonin, skullcap, poria, albizza flower, jujube, polygonum, valerian, lavender, hop, chamomile, St. Johns wort, rosemary, valerian, hops, blue vervain, passionflower, wild lettuce, hawthorn, lemon balm and goji, and green tea extract, each in an amount of at least about 0.01 mg per U.S. fluid ounce (about 29.6 milliliters), more preferably at least about 0.1 mg per U.S. fluid ounce of toothpaste.

It is also possible to formulate different toothpastes in accordance with the invention to be used in a coordinated fashion. A coordinated fashion can mean that two or more toothpaste formulations provide various aspects of treatment for a particular skin condition or need. For example, two toothpastes may complement each other in providing different active agents separately, both of which are intended to address various aspects of aging such as skin elasticity, skin repair, and/or skin brightening. Complementary may also mean that they are coordinated in terms of time. As already noted, it is possible that one formulation be designed to be used in the morning and a second one in the evening. This too is a form of coordination. Coordination can include the use of two toothpastes, one immediately before the other. It can involve the use of a toothpaste of the invention and a second fluoride-containing toothpaste.

Just as the idea of using a toothpaste to deliver active agents sustaining health and well-being of skin is unique, so too is the idea of using two different toothpastes with two different goals or benefits, at least one of which involved skin care, in a daily regimen.

These discussions of coordination generally reference the use of two distinct toothpastes. It will be appreciated that any number of toothpastes can be used in the methods of the invention and provided in the kits of the invention such as 1, 2, 3, 4, 5 toothpastes, etc.

Coordination can also involve coordinating skin care with oral health. The toothpastes of the invention may be designed and formulated to promote health within the oral cavity and to be swallowed. On the other hand, fluoride is known to support oral health but toothpastes containing fluoride should not be swallowed. A first toothpaste of the invention can be administered in the morning by being vigorously brushed throughout the oral cavity, preferably for at least two minutes as recommended (the normal brushing process) and then swallowed, and a second, fluoridated toothpaste used thereafter, using the normal brushing process, prior to retiring for sleep. The amount of fluoride will degrade in its form, but is commonly known in the industry after about 1 mg or more. The order of administration can also be reversed. This is a further example of coordination in accordance with the invention. Alternatively, both toothpastes of the invention can include ingredients for supporting or sustaining specific aspects of skin health, well-being, and/or appearance, targeted for specific times of day. The same or different aspects of skin health, well-being, and/or appearance can be addressed by these two toothpastes of the invention. Thus coordination can mean, for example, that both toothpastes address skin elasticity. Alternatively, the two toothpastes can be coordinated to address beautifying a user's skin by addressing two or more different potentially problematic issues such as, for example, coordinating the use of a morning formulation supporting elasticity with an evening formulation supporting skin repair (wrinkles), two issues which often go hand in hand and treating just one may be suboptimal. Each of these coordinated toothpaste formulations may offer other benefits as well. For example, they both might help with radiance and hydration. But the evening formulation may also assist in restfulness—something that, as noted elsewhere, impacts sleep which has a significant impact on skin health and beauty.

Coordination can occur on other levels as well. For example, toothpaste formulations of the present invention may also be formulated and used in coordination to work best with, or to even address, various skin types. Many formulations may be useful no matter which of the six skin types (normal, oily, compound, dry, sensitive and acne prone) a user might have. Others may be useful in trying to mitigate their impact on a particular skin type and/or on actually helping to address the condition. Again, just for example, both can be formulated for users with oily skin—either by including ingredients to help with oiliness or to not use ingredients which might make skin more oily, or both.

For example, the BASIC AM and PM formulas can be coordinated to provide the skin beautifying regimen focused primarily on elasticity, repair and/or restfulness in all skin types. But one or both of the formulation s can be modified to include active agents that are known to support skin health and which deliver benefits which address the specific needs of a particular skin type, such as Dry, Oily, Combination, Sensitive, and Acne Prone. For example, BASIC AM can be formulated to include additional clarifying extracts such as tea tree oil, or lemon or grapefruit, which are beneficial for oily skin. The BASIC AM formula can be formulated for Sensitive Skin to include soothing extracts such as lavender, coltsfoot or cucumber; active agents such zinc, astaxanthin, selenium, magnesium or polypdium leucotomos can be incorporated for Acne Prone skin; and active agents such as fenugreek, flaxseed, bladderwrack, lingonberry, etc. for Dry Skin; grapeseed oil or other omega-6 fatty acid containing extracts for combination skin, and so on.

In fact, the invention offers additional advantages in cases of heightened sensitivity skin-types, or problematic skin, such as acne, or sensitive skin, where topical products, instruments and devices may create irritations, or clog pores.

The following lists identify additional active agents that can be particularly beneficial for dry, oily, acne prone, and sensitive skin types.

Dry Skin
acacia extract
aloe extract
althea root extract
arnica extract
borage extract
calendula extract (marigold)
chamomile extract
clove extract
clover blossom extract
comfrey extract
dandelion extract dulse extract
elderberry extract
fennel extract
ginseng root extract
hibiscus extract
Irish moss extract
ivy extract
kelp extract
linden flower extract
melilot extract (hayflower)
oatmeal extract
orange flower extract
orange peel extract
parsley extract
peach extract
peppermint extract
primrose extract
quince seed extract
rose hips extract
sambucus elder extract
slippery elm bark extract
southernwood extract
spearmint extract
violet extract
white willow bark extract
yarrow extract
Oily Skin
buchu extract
chamomile extract
cornflower extract
cucumber extract
dandelion extract
dulse extract
fennel extract
gentian root extract
grapefruit extract
heather extract
Irish moss extract
kelp extract
lavender extract
lemongrass extract
lemon peel extract
linden flower extract
nettle extract
papaya extract
peach extract
rose bud extract
rose hips extract
sage extract
sambucus (elder) extract
sandalwood extract
spearmint extract
white lily extract
witch hazel extract
Combination Skin
grapeseed oil
omega 6 fatty acids
Acne Prone Skin
arnica extract
blackberry extract
burdock root extract
calendula extract (marigold)
clove extract
eucalyptus extract
goldenseal extract
hops extract
juniper berry extract
lavender extract
lemongrass extract
lemon peel extract
myrrh extract
papaya extract
thyme extract
tomato extract
valerian root extract
walnut extract (black)
white birch extract
white willow bark extract
Sensitive Skin
aloe extract
bergamot extract
buckthorn extract
calendula extract (marigold)
cranberry extract
jasmine extract
lavender extract
meadow sweet extract (mayflower)
oatmeal extract
passion fruit extract
peppermint extract
sage extract
sambucus elder extract
walnut extract (black)
yucca extract Still another form of coordination involves using only toothpastes of the invention designed to be swallowed and to support the health, well-being, and/or appearance on day one and on day two using either a mixture of such toothpastes with at least one brushing of at least one fluoride containing toothpaste that is not to be swallowed or even using only fluoride containing toothpastes that are not to be swallowed on day two. The cycle can then be repeated. This is another coordinated use of the toothpastes of the present invention.

The toothpastes of the present invention can also be formulated to be complimentary to and to be used in a coordinated fashion with other aspects of a skin care regimen in addressing, for example, skin elasticity. Some active materials may be better administered topically than administered systemically. Coordinating the design of a toothpaste and a topical skin care product to optimize that delivery is one aspect of the invention. Alternatively, certain active agents may work best when administered orally but are not compatible with a toothpaste formulation for one reason or another (too large a volume, objectionable odor or taste, unstable around other active agents, destabilizes other active agents, and the like). Toothpaste formulations, oral rinses, and tablets or capsules for coordinated delivery of some active agents orally through toothpaste and others using a tablet or capsule are also contemplated. Kits that include both a toothpaste and one or more skin care products designed to be applied topically or given as a pill or capsule are therefore contemplated. And methods of their coordinated use are contemplated as well.

Various complementary and coordinated uses of toothpastes in accordance with the invention include, without limitation, those shown in TABLE 2. It should be noted that unless otherwise indicated, all such formulations are designed for normal skin. That said, most of such formulations would be effective in other skin types or could be adjusted to be even better suited to a particular skin type:

TABLE 2

| | |
|---|---|
| BASIC/AM | |
| PM Elasticity | |
| PM Repair | |
| BASIC/AM with Vitamin C | |
| Whitening formulation | |
| Anti-Wrinkle formulation | |
| Stress/Bliss formulation | |
| Sunscreen/Sun formulation | |
| Acne/Psoriasis formulation | |
| Vegan formulation | |
| Vegan PM formulation | |
| Menopause formulation | |
| Hair/Nails formulation | |
| Detox/Cellulite | |
| Deep moisturizing formulation | |
| Radiance/Luminosity formulation | |
| Skin whitening formulation | |
| AM/Fluoride formulation | |
| PM/Fluoride formulation | |
| BASIC AM—sensitive teeth | |
| PM—sensitive teeth | |
| Men's formulation | |
| Probiotic formulation | |
| Pregnancy formulation | |
| Postpartum and PMS formulations | |
| Anti-oxidant SuperFood formulation | |
| Skintype Formula—Dry | |
| Skintype Formula—Sensitive | |
| Skintype Formula—Oily | |
| Skintype Formula—Combination | |
| SuperFood Formula | |
| Adaptagen Formula | |
| BASIC/AM | PM |
| BASIC/AM | PM Repair |
| BASIC/AM (for oily skin) | PM |
| BASIC/AM | PM (for oily skin) |
| BASIC/AM (for oily skin) | PM (for oily skin) |
| BASIC/AM (for dry skin) | PM (for dry skin) |
| BASIC/AM (for sensitive skin) | PM (for sensitive skin) |
| BASIC/AM (for combination skin) | PM (for combination skin) |
| BASIC/AM (for acne prone skin) | PM (for acne prone skin) |
| BASIC/AM (for normal skin) | PM (for normal skin) |
| BASIC/AM (for oily skin) | PM (for combination skin) |
| BASIC/AM | Detox/Cellulite—(Body) formulation |
| BASIC/AM with C | PM Elasticity |
| BASIC/AM with C | PM Repair |
| BASIC /AM with C and Citrus flavor | PM Repair |
| BASIC/AM with C and Citrus | Whitening formulation |
| BASIC/AM | Anti-Wrinkle formulation |
| BASIC/AM with C | Sun Protection formulation |
| BASIC/AM with C | Topical Sunscreen |
| Vegan AM | Vegan PM |
| Menopause | PM |
| AM Fluoride toothpaste—not to be swallowed | PM Fluoride toothpaste—not to be swallowed |
| AM toothpaste formulated to deliver vitamins and minerals | PM |
| BASIC/AM | Oral Supplement |
| BASIC/AM | Lip Product |
| Holiday Blissed Stress Formula | PM |

TABLE 2-continued

| | | |
|---|---|---|
| BASIC/AM—Morning | BOOST—Noon | PM—Evening |
| BASIC/AM with C Morning | BOOST—Noon | PM—Evening |
| VEGAN—AM | BOOST—Noon | PM—Evening |
| BASIC/AM with C Morning | BOOST—Noon | PM—Evening |
| BASIC/AM | PM | Topical Skincare |
| AM toothpaste formulated to deliver vitamins and minerals | Fluoride toothpaste | PM |
| BASIC/AM | PM | Anti-wrinkle mouthwash |
| Holiday Boxed Gift Sets: Christmas, Valentines Day, Easter, Mother's Day, Father's Day, Thanksgiving: Basic AM and | Holiday Boxed Gift Sets: Basic AM and PM And Subscription Gift Certificate PM | BASIC AM with Co-Branded Sonic Toothbrush or other Co-branded products. |

One method in accordance with the present invention involves at least once daily applying a toothpaste in accordance with the present invention by brushing the toothpaste onto a person's teeth, gums, tongues, etc. for cleansing purposes, preferably for at least two minutes as dentists often recommend and then swallowing the toothpaste and/or allowing its components to be absorbed within the oral cavity. This can be repeated two, three or more times a day. Methods of the invention also include, in some embodiments, brushing at least once a day using a toothpaste formulation of the invention without rinsing with water or expelling the toothpaste.

Another method in accordance with the present invention involves a method of the coordinated use of different toothpastes of the present invention at coordinated times. It involves the administration of a toothpaste in accordance with the present invention by brushing and swallowing or by absorption as noted above and, at some other point in the day, using a fluoride containing toothpaste which is not swallowed. In one embodiment, the toothpaste of the invention is used in the morning and the fluoride toothpaste is used in the evening. In another embodiment, the fluoride toothpaste is used in the morning and the toothpaste of the invention is used in the evening. It is understood, however, that one can use either or both of these toothpastes more than once a day.

In another aspect of the invention, a method is provided which involves using two different toothpastes each designed to be swallowed and/or absorbed in the oral cavity and each addressing a different aspect of skin health, well-being and/or appearance. These may be used as previously described by being brushed on the teeth and gums, and then swallowed and/or absorbed from the oral cavity, one in the morning and one in the evening, both in the morning, both in the evening, and the like. This, too, is an aspect of coordination.

Another method in accordance with the present invention is a method of treating skin to sustain its health, well-being and/or appearance which includes the use of a swallowable/absorbable toothpaste in accordance with the present invention supplemented by ingesting one or more oral supplement, which may be taken at a time proximate the use of the toothpaste or at some other time during the day, or with a cream, ointment, lotion, milk, scrub, paste, serum, cleanser, syrup, salve, or the like meant to be applied to the skin proximate the use of the toothpaste of the present invention or thereafter.

Kits

"Kits" in accordance with the present invention include either: 1) a toothpaste in accordance with the present invention that supports or sustains the health, well-being, and/or appearance of skin or other health-related benefit; or 2) at least two different coordinating toothpaste formulations such as those just described. In one embodiment, at least one of the toothpastes of the kit is not to be expelled. In one embodiment, at least one of the toothpastes in each kit is designed to be swallowed. In another embodiment, at least one of the toothpastes within the kit is not fluoridated, or a "whitening" toothpaste, or both.

In some embodiments, the kit will include at least two toothpastes with at least one toothpaste designed to be swallowed/absorbed and/or includes at least one active agent which supports the health, well-being or appearance of a user's skin, wherein the first toothpaste and the second toothpastes are different formulations. In other embodiments of this aspect, the kits can include two or more differently formulated toothpastes in which one or more formulation is intended to be swallowed and they are intended to be used at different times in a day. In still another embodiment of this aspect, both (or more) of the toothpastes are intended to be swallowed/absorbed and they may address the same or different aspects of the health, well-being, and/or appearance of the user's skin. The components of the kits may be coordinated not only in terms of specific aspect of the beautification of skin by addressing certain aspects such as elasticity, radiance, wrinkles and repair, hydration and the like, but also may be coordinated in terms of skin type as well. And in yet another aspect, in addition to a second toothpaste (or more), the kits include topically applied creams, lotions, gels, ointments, scrubs, cleansers, washes, serums, solutions, milks, emulsions, and/or pastes (some or all of which can include an active agent) and/or orally administered tablets, capsules, powders, drinks, rinses, lozenges, chews, gums, and the like containing an active agent.

Kits can include: brushes, floss, applicators, instructions, holders, caddies, and the like. These may be coordinated in style, color, appearance, and/or size to foster an association with one of the toothpastes or creams (etc.) in the kit.

In certain embodiments, kits include first and second toothpaste formulations differ in at least one of: the indicia used on their respective packaging, the color of their respective packaging, the accessories provided with each toothpaste, the design and artwork used on their respective packaging, the type of vehicle used for each respective formulation, the color of each respective formulation, the aroma of each formulation, and the flavor of each respective formulation.

And in still another embodiment, a kit may be provided including both a fluoride containing toothpaste to be expelled and a toothpaste in accordance with the present invention which is to be swallowed. Moreover, a kit could be provided in which a toothpaste in accordance with the present invention is used with popular commercial brands such as Crest, Colgate, and Sensodyne to provide the fluoridated toothpaste. This too would help identify which paste is which. The method of their application is in each case the same except where a paste is to be swallowed or washed out of the mouth.

Another form of cobranding which may be used in accordance with the present invention is the use of, for example, flavors, colors and/or packaging in association with other consumer brands. STARBUCKS offers unique, seasonal flavors leading up to holidays such as pumpkin spiced and gingerbread latte. Toothpastes of the invention could be flavored and/or colored to match the latte product and the labeling could be adjusted accordingly. DUNKIN brands offer holiday coffee blends. ALTOIDS Peppermint, LIFESAVER Wintergreen, DENTYNE Ice Winter Chill gum are bold mint flavors for gums and mints. Toothpastes like Boost formulations, which are often going to be used during the day, are particularly good candidates as the consumer can use the toothpaste and the associated product without their flavors clashing. The co-branding possibilities can go well beyond coffee and mints and can include an array of leading consumer food and beverage/packaged goods brands, or the like. Another form of cobranding which may be used in accordance with the present invention is the use of popular, branded, monthly subscription shave clubs and related products such as Billies, Happy Legs, Harrys, Birchbox, Dollar, Morgans and Bevel.

For a non-limiting example, a toothpaste in accordance with the present invention that is supporting or sustaining the health, well-being, and/or appearance of skin and which is to be swallowed and/or absorbed could be designed to be used in the morning before or after breakfast (such as the BASIC AM toothpaste formulation). It could be packaged so as to help identify it as a toothpaste to be used at that time of day and could be colored, flavored, and given an aroma to further support that association such as: orange juice flavored. It can also be mint flavored. The coordination of this morning formulation with one or more other toothpastes and the packaging thereof is a kit in accordance with the invention. This toothpaste could be supplied with a second toothpaste having a different formulation and intended to be used at a different time of day, a brush, a dispenser of floss, a topical product, an applicator, a second oral product, and/or an accessory such as a case or caddy. Any and all of these combinations are kits as well. The second toothpaste could be a fluoride toothpaste not intended to be swallowed. It could be a vitamin containing toothpaste intended to be swallowed, or a toothpaste designed to support skin elasticity and hydration. It could also be any of the exemplary coordinated formulations listed in TABLE 2.

Series of Kits

A kit in accordance with the present invention can comprise a series of kits with the same or different constituents. Kits could be designed to provide sufficient product to last a month or other periodicity. Each new month, another kit could be provided supplying the same toothpastes wherein the packaging, the flavor, the color and/or the aroma could be changed. Kits of this type could also alter the nature of the toothpastes with each new month or every couple of months. In the winter due to dryness, skin elasticity and hydration may be of particular importance. Accordingly, toothpaste kits for cold weather could include toothpastes to be ingested in the morning, in the evening, or both which focus on skin hydration and skin elasticity. In spring or autumn, however, skin nutrition may become the focus. In that case, the AM toothpastes of the kits for those months are could focus on elasticity while the evening toothpastes focused on nutrition. In summer the toothpaste kit could include the formula for sun protection or skin repair. In another embodiment, active agents could be included that are known to mitigate allergic responses, beneficial for those who suffer seasonal-related allergies. In the late spring and early summer, elasticity may be less of an issue and hydration and boosting the skin's natural defenses to sun damage may become the priority. Yet, for some users or in some locations, sun damage may be an important year round benefit with formulations adjusted accordingly. These are but examples. And each monthly collection of morning and evening toothpaste is a kit, as is the overall collection of kits for, in this example, monthly seasonal needs.

A kit could also be provided in four seasonal units that build an association with particular seasons. The fall kit unit, for example, could include tubes of toothpaste intended to be used in the PM that are pumpkin latte flavored which is to be swallowed and addresses some aspect of the health, well-being and/or appearance of skin and tubes of toothpaste intended to be used in the AM which contain fluoride and are thus not to be swallowed, and may be flavored with other autumnal-associated and/or spiced tastes. Due to the popularity of the Christmas season, and the popularity of fun flavors, other tubes of toothpaste could be provided to be used in December only including a morning toothpaste flavored of wintermint, candy cane, gingerbread, or peppermint which is not to be swallowed and provides fluoride as did the seasonally flavored toothpaste supplied for October and November. This seasonal kit could also include an evening peppermint or winter spice toothpaste to be swallowed which addresses the same aspect of health, well-being and/or appearance of skin as was addressed in the PM pumpkin latte flavored toothpaste formulation mentioned above.

This fall or winter kit could also include two smaller additional tubes of toothpaste just to be used on specific holidays One example could be colored red and green, silver and gold colors that have an association with Christmas and/or travel sizes that can be used as stocking stuffers, gifts, or holiday travel.

Brushes as Part of Kits

As noted previously, brushes could be supplied as part of the kits coordinating with the theme and function of the toothpastes in the kit. Using the month of December in the kit above again as an example, the brush provided for the PM toothpaste could be more giftable and have a big brush head to allow ingestion of a sizable dose of the seasonal toothpaste. The toothbrush to be used for the AM formulation could also be a giftable design with the smaller round-head head with bristles limiting the amount of fluoride toothpaste to be used.

But, whether used or supplied as part of a kit or not, brushes can be used to assist in metering toothpaste used and/or dosing toothpastes of the present invention. One way of helping to control dosing is by including, within a kit, a toothbrush that is appropriately sized and configured for one or more of the toothpastes. Dentists suggest a relatively small "dollop" of fluoride toothpastes be used, often explained as the size of a large pea or bean. A small round headed toothbrush could be provided to be used with a fluoride toothpaste to help ensure that not too much is used and/or similarly for a formula containing a high or potent concentration of an active. On the other hand, a toothpaste of the invention may address a specific aspect of the health, well-being, and/or appearance of skin or other health-related benefit by including an active agent to be swallowed that requires a high dose. Not only can that impact the concentration and/or amount of that active agent formulated in the toothpaste, but by producing a relatively large, long, rectangular headed brush and in treating the user to apply sufficient toothpaste to cover the entire brushing surface, or a full head, one can further regulate the amount of toothpaste, and therefore active agent, ingested.

This has other benefits as well. One can throw out the corresponding brush when the package of toothpaste is used up ensuring that the brush does not become too old and/or to retard the build up of, for example, microbes. A new toothbrush would be used with each new package of toothpaste. And this need not adversely impact the environment. The brushes could be produced from sustainable, biodegradable materials such as wood, pulp, and biodegradable polymers, or can be produced from recycled plastics. The brushes may also be coordinated in color, indicia, artwork, and/or design so as to assist the user in knowing which toothpaste goes with which brush.

In another embodiment, one or more brushes could be provided where the bristles are colored to help meter the dose. For example, a rectangular head could provide orange bristles from its tip extending for 60% of the length of the brush head and blue bristles over the remaining 40%. An orange "morning" toothpaste can be applied to the brush so that it substantially only covers the orange 60% of the brush. In the evening, a PM paste could be applied substantially only to the 40% of the brush head bristles that are blue. The orange 60% could be centered along the brush head and the AM toothpaste is once again applied to the orange bristles. At night, however, the blue PM toothpaste is applied alone the entire length of the bristles on the brush head. Color or shape coordinating of the bristles of the head of the brush with toothpastes of the kit are therefore also an aspect of the invention.

The packaging of each tube (or other type of dispenser) can be changed in color and content to not only reflect the particular toothpaste but also the month, season, holiday or theme. Aromas can also be varied.

To provide a better appreciation of the full scope of coordinated uses and kits in accordance with the present invention, consider a kit with a morning formulation, one to be used after one arises and before consuming breakfast. This formulation could be a Vitamin C formulation, orange citrus flavored to address one of the more annoying problems for orange juice drinkers, namely, the interaction of a mint flavored paste with orange juice. The toothpaste could be lightly orange colored and orange scented. The toothpaste is designed to be swallowed and addresses skin elasticity. The kit may also come with an orange toothbrush made of biodegradable or recyclable materials so it is clear which toothbrush is to be used with the morning orange toothpaste. Because of the number and volume of ingredients useful for the health, well-being, and/or appearance of the skin contained in such an AM formulation, the toothbrush has a traditional rectangular head with multiple rows of bristles to accommodate a relatively large dollop of toothpaste.

The kit may also include a toothpaste to be used after lunch. This toothpaste is, just for example, a co-branding paste comprised of a traditional flavor. A coordinating colored toothpaste, preferably made from recyclable or biodegradable materials is also provided colored to coordinate with the toothpaste and having a different shaped head such as a smaller, round head. It can also bear the toothpaste brand name. Because this co-branded toothpaste is a fluoridated toothpaste, the amount to be applied should be around the size of a large pea and the formulation is not to be swallowed. In an alternative embodiment, the fluoridated toothpaste could be included in a package evoking a particular time of day, such as noon, or lunchtime. The toothbrush could be coordinated. This toothpaste would be positioned for use after eating lunch and provide a minty feel, flavor, and aroma to help cleanse the user's breath following the lunch meal.

A third toothpaste could be provided, one which may be swallowed or expelled and need not have fluoride nor an active agent useful in supporting the health, well-being, and/or appearance of skin. This formulation could be an antioxidant formula with a taste and aroma of espresso, cappuccino, or coffee. It could provide caffeine and an afternoon lift and boost. It could be provided with a brown, biodegradable or recyclable toothbrush whose head, size, and composition can be adjusted depending on the composition of the toothpaste. Many people experience a lull in their energy at about 3:00 PM to 4:00 PM in a normal day's schedule. Often they will reach for a caffeinated beverage such as coffee and/or perhaps a snack to elevate their energy so they can complete the workday. Providing an "invigorating" toothpaste with a flavor to match that of the coffee or other ingestible they likely consume provides an association encouraging them to brush, which can address the acidity introduced by the coffee and/or cleanse the mouth from any snack that has been consumed while, at the same time, sustaining the residual taste of the coffee. The brushing process and the toothpaste will help awaken and revitalize the user, provide additional antioxidants, and, if it contains caffeine, it can help support restoration of energy and skin vitality.

A fourth toothpaste can be provided to be used following the evening meal and proximate to sleeping or going to bed. Phrases such as "to be used proximate to sleeping" and similar terms mean that the toothpaste formulation is designed to be used in the interval prior to going to sleep. It will be appreciated that for most people this is in the night or evening, often after an evening meal, or prior to sleeping. Some people have different schedules and may work at night or during a shift which does not fit neatly into the daytime/nighttime division of time. Others can be traveling to a different time zone and experiencing jet lag. In any event, all of us need sleep and the toothpaste formulations in question may be designed to be used around the time that the user intends to go to sleep. These formulations may include active agents that work best when the user is sleeping for an extended period, active agents that promote calm, restfulness or sleep, or both.

The kit can be sold as just tubes of toothpaste, tubes of toothpaste with the coordinating brushes, mouth rinses, and/or with other accessories such as, for example, a holder or caddy. Other containers such as pumps, dispensers, jars, and the like may be used. Indeed, a plurality of caddies could be provided, one for home use for the morning and evening brushing, and one for the office for the lunch time and afternoon brushing. The kit could be preassembled with two, three, four or even more different combinations of toothpaste, brushes, floss, topicals, applicators, and/or tablets or capsules. But what if a user does not drink orange juice in the morning and does not like coffee? In one embodiment, they could contact the company either by telephone, facsimile or e-mail, by logging onto a website, or at a display or kiosk in a store, and replace one flavor with another having flavor preferential to the user. The brush and packaging could stay the same, however, to remind the user that this is the AM toothpaste, and that it is intended to be swallowed. For example, a user who does not like coffee might prefer tea and select as the invigorating toothpaste one having a flavor/aroma and/extracts of anti-oxidant Earl Grey, or antioxidant Green Tea.

Perhaps the user believes that more fluoride should be applied to their teeth during the day. They could then swap any number of the toothpastes for fluoridated toothpaste of the otherwise identical packaging and format. The brush could be different reflecting the smaller dose to be provided and, of course, the packaging would reflect that that toothpaste is not to be swallowed.

Kits in accordance with the present invention can also be sold as a subscription over a period of time. The user may choose monthly delivery of single, or multiple tubes, with or without other accessories, coordinating brushes, floss, or rinses, etc. over a subscription period spanning from 2, 3, 6 to 12 months or longer. During the course of the subscription period, the user may choose one formulation for a period of time, and/or alter or vary the formulations included in the next delivery to address individual skin care issues or other individual monthly preferences. For example, the user may choose a Kit 3-month subscription starting with, amongst other things, the BASIC AM formula for a period of 2 months and choose the Anti-Wrinkle formula for month 3. A user may choose a kit in a 6 month subscription that provides a broad range skincare benefits such as, without limitation, Month 1 BASIC AM, Month 2 Anti-Wrinkle, Month 3 Cellulite and Body, Month 4 Radiance and Glow, Month 5 Acne Formula, and so on. The kit could also include, again as an example, a PM formulation, indeed, the same PM formulation for each of the 6 months. Kits in accordance with the invention provided as part of a subscription (or indeed otherwise) can adapt or be adapted to the changing skin requirements of the user over time such as monthly, seasonally, and the like. Kits in accordance with the invention in a monthly subscription can target seasonal skin requirements and interests, such as dryness with a Moisture formula during the winter season. A monthly kit subscription could also be assembled that addresses beauty and oral wellness benefits, such as interchanging with the Basic AM with the Whitening formula, or a formula containing Fluoride, and so on. Or, varying formulas to address skin issues, oral wellness and inflammation, micro biome and the like. Note that monthly subscriptions and kits have been described. However, different periods of time can be employed as well to accommodate the needs of the user such as, without limitation: weekly; bi-weekly; bi-monthly; quarterly; and semi-annually.

Kits in accordance with the present invention, in addition to toothpastes, topical formulations and/or orally ingested tablets, capsules, and the like, can include other elements and accessories. Rinses could be provided such as mouthwash, teeth whitening rinses, and the like. Indeed, fluoride containing rinse can be used either in conjunction with a kit including a fluoride containing toothpaste or a kit which includes no a fluoride containing toothpaste. Dental floss can be provided. There can be provided an applicator for topical applications or brushes for use in the oral cavity. As is true with other aspects of the invention, rinses, and accessories can be colored, shaped, configured, and/or flavored as appropriate in a coordinating, contrasting or identical way. There can also be provided sonic toothbrushes, toothbrush heads, and toothbrushes or lights providing specific wavelengths of light to assist in teeth whitening.

As described herein, kits can, and often do, respond to input from the user. As noted above, the user can alter the content of future kits to respond to their changing needs. Kits could also include pH test strips, meters, or other indicators, which would allow the user to determine their skin's pH and order toothpaste formulations or rinses or other pH balancing products tailored to help adjust the pH of the user's skin to obtain a particular pH or restore a proper pH balance. A user could test their pH and take steps to adjust the pH as needed. A separate pH balancing formulation (a toothpaste, wash, rinse, or otherwise) can be provided as well.

It is also possible for kits to include customized formulations responding to a user's specific requests or input. Existing toothpaste formulations could be adapted to provide particularly needed additional skin benefit responsive to a particular user's needs. These augmented formulations could then be supplied directly, individually, and/or as part of a kit.

The color of a toothpaste in a kit in accordance with the invention could be yellow and a rinse which is to be used around the same time as brushing with that yellow toothpaste can be yellow colored as well, A second toothpaste provided with that kit could be red. The use of the yellow color in the rinse helps associate the rinse with the first toothpaste and remind the user that they should be used together (one after the other, at about the same time). Similarly, two different toothbrushes, of two different colors, could be used and supplied as part of the kit; one colored indicating that it be used with the first toothpaste and the other colored so that it is used with the second toothpaste. Again, and as noted earlier, while most of the discussion has been in terms of the single paste or two pastes, any number of pastes, any number of rinses, any number of brushes, two toothpastes and a topical cream, three toothpastes and a serum to be used under the eyes, a cleanser to be used on the face, and a gel to be applied elsewhere, along with an applicator for each, could be provided. The topical formulations could be colored to remind the user that they should be used in conjunction with a particular toothpaste. They could be provided with an aroma that complements the flavor used for one paste or the other. And of course their packaging could be complementary and informative as to when the topical product should be used. Tablets and capsules can be colored accordingly.

The kits of the present invention may be formulated and packaged in in a tube or other dispenser, in a coordinating fashion. This can involve the shape of the container, its color, artwork and/or indicia. This will help the user distinguish one toothpaste useful at one time from another and remind a user in real time which toothpaste they are using. The toothpaste may be labeled in a coordinated fashion. One could be flavored as a mint and the other as cinnamon or some other non-mint flavor. One could be in the form of a paste and the other a gel. If one of the pastes provided in a kit is not to be swallowed, it could include prominent reminders that it should not be swallowed. These are, of course, non-limiting examples.

The present invention includes a method of supporting the health, well-being and/or appearance of a user's skin through the coordinated application of two different toothpastes daily to the oral cavity of the user, including the steps of:

a) applying to the oral cavity of the user proximate to the user waking a first toothpaste formulation supporting skin elasticity containing at least one active agent supporting skin elasticity;
b) brushing the oral cavity with the first toothpaste formulation;
c) swallowing at least a portion of the first toothpaste formulation;
d) applying to the oral cavity of the user proximate to the user going to sleep a second toothpaste formulation supporting skin repair, restfulness or elasticity containing at least one active agent supporting skin repair and wherein the second toothpaste formulation is different than the first toothpaste formulation;
e) brushing the oral cavity with the second toothpaste formulation; and
f) swallowing at least a portion of the second toothpaste formulation;

and wherein the first and second toothpaste formulations are each administered in an amount sufficient to provide at least one of the following active agents: Spirulina 10 μg-500 mg; Aloe 10 μg-500 mg; CoQ10 10 μg-500 mg; Bilberry 10 μg-500 mg; Glucosamine 10 μg-500 mg; Vitamin E 10 μg-500 mg; Vitamin C 10 μg-500 mg; or HA 10 μg-500 mg; and further comprising at least one excipient selected from the group consisting of: abrasives, carriers, sweeteners, flavorings, colorings, stabilizers, preservatives, viscosity enhancers, pH adjusters, buffers, sparkles, gelling agents, surfactants, effervescent agents, binders, thickeners, rheology modifying agents, remineralizing agents, humectants, desensitizing agents, sensitivity agents, whitening agents, mucosal adhesives, bad breath agents, gingivitis agents, astringents, and oxidizing agents. In other aspects, this method can be practiced where only one of the coordinated toothpaste formulations is swallowed.

In some embodiments of the above method the first toothpaste formulation includes an active agent supporting skin elasticity selected from the group consisting of: Aloe barbadensis, bilberry, coenzyme Q10, Vitamin E, glucosamine, honey, spirulina, hyaluronic acid, Vitamin C, green tea extract, SOLIDENTI, *Centella asiatica* extract, *Polygonum cuspidatum* root extract, *Scutellaria baicalensis* root extract, *Camellia sinensis* leaf extract, *Glycyrrhiza glabra*(licorice) root extract, *Chamomilla recutita*(matricaria) flower extract, *Chamomilla recutita*, and mixtures thereof. The second toothpaste formulation also includes an active agent supporting skin elasticity selected from the group consisting of: Aloe barbadensis, bilberry, coenzyme Q10, Vitamin E, glucosamine, honey, spirulina, hyaluronic acid, Vitamin C, green tea extract, SOLIDENTI, *Centella asiatica* extract, *Polygonum cuspidatum* root extract, *Scutellaria baicalensis* root extract, *Camellia sinensis* leaf extract, *Glycyrrhiza glabra*(licorice) root extract, *Chamomilla recutita*(matricaria) flower extract, *Chamomilla recutita*, and mixtures thereof. Alternatively, the second toothpaste formulation includes an active agent supporting skin repair selected from the group consisting of: Vitamin A, aloe barbadensis, chamomile flower, coenzyme Q10, Vitamin E, glucosamine, hyaluronic acid, honey, passionflower, spirulina, zinc, pearl powder, polypodium leucotomos, pomegranate extracts, collagen, cycloastragenol, nicotinamide riboside, nicotinamide mononucleotide, turmeric, protein, Vitamin D, Vitamin K, ALA, grape seed extract, collagen peptide, crocin, astragalus, lutein, resveratrol, ceramides, ferulic acid, sunflower shoot, propolis, green tea extract and goji, and mixtures thereof. In either case, the second toothpaste formulation may additionally include an active agent supporting restfulness including: melatonin, skullcap; rosemary; chamomile; poria; albizza flower; jujube; polygonum; valerian; lavender; hops; St John's wort; blue vervain; passionflower; wild lettuce; green tea extract, hawthorn, lemon balm and, goji, and mixtures thereof. The total of these restfulness supporting active agents is often up to a total up to about 6 wt % (6% wt/wt used interchangeably). But in some embodiments the total of the active agents supporting restfulness used in the second toothpaste formulation is up to about 3 wt %.

The above method can include first and/or second toothpaste formulations that are formulated to treat a particular skin type selected from the group consisting of: dry skin; oily skin; combination skin; sensitive skin; acned skin or normal skin.

The method of claim 1 wherein steps a)-f) are repeated daily and indeed daily for at least 2 weeks and in another embodiment, at least 4 weeks.

A kit for supporting the health, well-being and/or appearance of a user's skin through the coordinated application to the oral cavity of a plurality of different toothpaste formulations is also contemplated and includes:

a first container containing an amount of a first toothpaste formulation sufficient for a plurality of applications to a user, the first toothpaste formulation formulated to be administered to the user proximate to the user's waking and containing from about 0.1 to about 20 weight % of at least one active agent supporting skin elasticity and selected from the group consisting of aloe barbadensis, bilberry, coenzyme Q10, Vitamin E, glucosamine, honey, spirulina, hyaluronic acid, Vitamin C, SOLIDENTI, *Centella asiatica* extract, *Polygonum cuspidatum* root extract, *Scutellaria baicalensis* root extract, *Camellia sinensis* leaf extract, *Glycyrrhiza glabra*(licorice) root extract, *Chamomilla recutita*(matricaria) flower extract, *Chamomilla recutita;* and a second container containing an amount of a second toothpaste formulation sufficient for a plurality of applications to a user, the second toothpaste formulation formulated to be administered to the user proximate to the user's going to sleep and containing from about 0.1 to about 20 weight % of at least one active agent supporting restfulness, elasticity or skin repair and selected from the group consisting of: Vitamin C, aloe barbadensis, chamomile flower, coenzyme Q10, Vitamin E, spirulina, SOLIDENTI, glucosamine, hyaluronic acid, passionflower, spirulina, zinc, pearl powder, polypodium leucotomos, pomegranate extracts, collagen, cycloastragenol, nicotinamide riboside, nicotinamide mononucleotide, turmeric, protein, Vitamin D, Vitamin K, ALA, grape seed extract, collagen peptide, crocin, astragalus, lutein, resveratrol, ceramides, ferulic acid, sunflower shoot and propolis, melatonin, skullcap, poria, albizza flower, jujube, polygonum, valerian, lavender, hop, chamomile, St Johns wort, rosemary, valerian, blue vervain, passionflower, wild lettuce, hawthorn, lemon balm, goji and green tea extract; and at least one excipient selected from the group consisting of: abrasives, carriers, flavorings, colorings, stabilizers, preservatives, viscosity enhancers, pH adjusters, buffers, sparkles, gelling agents, effervescent agents, thickeners, humectants, desensitizing agents, sensitivity agents, whitening agents, mucosal adhesives, bad breath agents, gingivitis agents, astringents, and oxidizing agents.

In these kits, preferably, the first toothpaste formulation contains from about 1.0 to about 10 weight % of at least one active agent supporting skin elasticity and/or the second toothpaste formulation contains from about 1.0 to about 10 weight % of at least one active agent supporting skin repair, restfulness and/or elasticity. The first and/or the second toothpaste formulations can be coordinated to treat the same skin type selected from the group consisting of: dry skin; oily skin; combination skin; sensitive skin; acned skin or normal skin.

The kit may also include a first toothbrush which coordinates with the first toothpaste formulation and a second toothbrush which coordinates with the second toothpaste formulation and in particular the first and second toothbrushes coordinate with the corresponding toothpaste formulations in head size, head shape, body shape, color, or indicia.

In another aspect, the invention contemplates a method of supporting an aspect of the health, well-being and/or appearance of a user's skin through the application of a toothpaste to the oral cavity of the user, including the steps of:

a) applying to the oral cavity of the user a first toothpaste formulation including a first active agent supporting an aspect of skin health, well-being and/or appearance of a user's skin;

b) brushing the oral cavity with the first toothpaste formulation; and c) swallowing at least a portion of the first toothpaste formulation;

wherein the first toothpaste formulation is administered daily for in an amount sufficient to provide at least one of the following active agents: Spirulina 10 μg-500 mg; Aloe 10 μg-500 mg; CoQ10 10 μg-500 mg; Bilberry 10 μg-500 mg; Glucosamine 10 μg-500 mg; Vitamin E 10 μg-500 mg; SOLIDENTI; Vitamin C 10 μg-500 mg; or HA 10 μg-500 mg; and further comprising at least one excipient selected from the group consisting of: abrasives, carriers, flavorings, colorings, stabilizers, preservatives, viscosity enhancers, pH adjusters, buffers, sparkles, gelling agents, effervescent agents, thickeners, humectants, desensitizing agents, sensitivity agents, whitening agents, mucosal adhesives, bad breath agents, gingivitis agents, astringents, and oxidizing agents; and wherein the aspect of skin addressed by the first toothpaste formulation is selected from: skin aging; signs of aging; skin irregularities; skin elasticity; collagen generation; hydration; skin nutrition; appearance of fine lines and wrinkles; skin discoloration; skin whitening; liver or age spots; skin softness; skin suppleness; skin firmness; skin sagging; skin drooping; dull skin tone; skin radiance; lines; wrinkles; crows feet; loss of volume; plumpness; luminosity; vitality; laugh lines; puffy skin around the eyes; discolored skin around the eyes; droopy eyes; scaly skin; rough skin; chapped skin; patchy skin; open pores in skin; cracked skin; dry skin; peeling skin; sunburned skin; sunspots; decollete wrinkles; crepey skin; acne; psoriasis; rosacea; and/or rash. In one aspect, the toothpaste is applied daily and in particular, daily for at least 4 weeks.

The method described immediately above can particularly include treating an aspect of the health, well-being and/or appearance of a user's skin including signs of skin aging; the appearance of fine lines and wrinkles; skin repair, skin hydration; skin softness; and skin elasticity.

The method can also include the steps of:

d) applying to the oral cavity of the user a second toothpaste formulation including a second active agent supporting an aspect of skin health, well-being and/or appearance of a user's skin and wherein the second toothpaste formulation is different than the first toothpaste formulation;

e) brushing the oral cavity with the second toothpaste formulation; and f) swallowing at least a portion of the second toothpaste formulation;

and wherein the first and second toothpaste formulations are each administered in an amount sufficient to provide at least one of the following active agents: Spirulina 10 μg-500 mg; Aloe 10 μg-500 mg; CoQ1010 μg-500 mg; Bilberry 10 μg-500 mg; Glucosamine 10 μg-500 mg; SOLIDENTI Vitamin E 10 μg-500 mg; Vitamin C 10 μg-500 mg; or HA 10 μg-500 mg; and each further comprises at least one excipient selected from the group consisting of: abrasives, carriers, flavorings, colorings, stabilizers, preservatives, viscosity enhancers, pH adjusters, buffers, sparkles, gelling agents, effervescent agents, thickeners, humectants, desensitizing agents, sensitivity agents, whitening agents, mucosal adhesives, bad breath agents, gingivitis agents, astringents, and oxidizing agents; and wherein the aspect of skin addressed by the first and the second toothpaste formulations may be the same or different and are selected from: skin aging; signs of aging; skin irregularities; skin elasticity; collagen generation; hydration; skin nutrition; appearance of fine lines and wrinkles; skin discoloration; skin whitening; liver or age spots; skin softness; skin suppleness; skin firmness; skin sagging; skin drooping; dull skin tone; skin radiance; lines; wrinkles; crows feet; loss of volume; plumpness; luminosity; vitality; laugh lines; puffy skin around the eyes; discolored skin around the eyes; droopy eyes; scaly skin; rough skin; chapped skin; patchy skin; open pores in skin; cracked skin; dry skin; peeling skin; sunburned skin; sunspots; decollete wrinkles; crepey skin; acne; psoriasis; rosacea; and/or rash.

In the method the aspect of the health, well-being and/or appearance of a user's skin is different for the first and the second toothpastes and both are selected from: signs of skin aging; the appearance of fine lines and wrinkles; skin repair, skin hydration; skin softness; and skin elasticity.

In some aspects of the method the first toothpaste is administered in the morning and the second toothpaste is administered at night.

In other aspects of the invention, there is provided a toothpaste supporting an aspect of the health, well-being and/or appearance of a user's skin through its application to the oral cavity of the user, including a first container containing an amount of a first toothpaste formulation sufficient for a plurality of applications to a user, the first toothpaste formulation containing from about 0.1 to about 20 weight % of at least one active agent supporting skin elasticity and selected from the group consisting of aloe barbadensis, bilberry, coenzyme Q10, Vitamin E, SOLIDENTI, spirulina, glucosamine and at least one excipient which is an a abrasive, carrier, flavoring, coloring, stabilizer, preservative, viscosity enhancer, pH adjuster, buffer, sparkle, gelling agent, effervescent agent, thickener, humectant, desensitizing agent, sensitivity agent, whitening agent, mucosal adhesive, bad breath agent, gingivitis agent, astringent, and an oxidizing agent.

In some embodiments, the first and or second toothpaste formulations contains from about 1.0 to about 10 weight % of at least one active agent. And in certain embodiments, the toothpastes contain active agents that are selected to address signs of skin aging; the appearance of fine lines and wrinkles; skin repair, skin hydration; skin softness; or skin elasticity.

There is also a kit provided herein for supporting the health, well-being and/or appearance of a user's skin through the coordinated application to the oral cavity of a plurality of different toothpaste formulations comprising:

a first container containing an amount of a first toothpaste formulation sufficient for a plurality of applications to a user, the first toothpaste formulation formulated to support the health, well-being and/or appearance of a user's skin and containing from about 0.1 to about 20 weight % of at least one active agent selected from the group including: SOLIDENTI, spirulina, aloe barbadensis, bilberry, coenzyme Q10, Vitamin E, Vitamin C, glucosamine, and hyaluronic acid; and a second container containing an amount of a second toothpaste formulation sufficient for a plurality of applications to a user, the second toothpaste formulation formulated to support the health, well-being and/or appearance of a user's skin containing from about 0.1 to about 20 weight % of at least one active agent selected from the group consisting of: SOLIDENTI, spirulina, Vitamin C, aloe barbadensis, chamomile flower, coenzyme Q10, Vitamin E, Vitamin C, glucosamine, and hyaluronic acid; and at least one excipient selected from the group consisting of: abrasives, carriers, flavorings, colorings, stabilizers, preservatives, viscosity enhancers, pH adjusters, buffers, sparkles, gelling agents, effervescent agents, thickeners, humectants, desensitizing agents, sensitivity agents, whitening agents, mucosal adhesives, bad breath agents, gingivitis agents, astringents, and oxidizing agents.

The aspect of skin health addressed by the first and the second toothpaste formulations may be the same or different and are selected from: skin aging; signs of aging; skin irregularities; skin elasticity; collagen generation; hydration; skin nutrition; appearance of fine lines and wrinkles; skin discoloration; elasticity; skin whitening; liver or age spots; skin softness; skin suppleness; skin firmness; skin sagging; skin drooping; dull skin tone; skin radiance; lines; wrinkles; crows feet; loss of volume; plumpness; luminosity; vitality; laugh lines; puffy skin around the eyes; discolored skin around the eyes; droopy eyes; scaly skin; rough skin; chapped skin; patchy skin; open pores in skin; cracked skin; dry skin; peeling skin; sunburned skin; sunspots; decollete wrinkles; crepey skin; acne; psoriasis; rosacea; and/or rash. In particular embodiments, the contents of the kit are coordinated to address different aspects of the health, well-being and/or appearance of a user's skin and are selected from: signs of skin aging; the appearance of fine lines and wrinkles; skin repair, skin hydration; skin softness; and skin elasticity.

The kit may also include a first toothpaste intended to be administered in the morning and the second toothpaste intended to be administered at night.

Exemplary Kits with Coordinated Toothpastes

1. AM BASIC and PM-Daily Regimen—AM/PM Treatment
   a. WildMint/WildMint
   b. Wildmint/NewMint
2. AM BASIC and PM (repair or elasticity)—Daily Regimen
   a. CitrisMint/NewMint
   b. CitrisMint/HerbalMint
3. AM BASIC and CELLULITE-BODY—Face and Body Regimen
   a. WildMint/WildMint
   b. WildMint/NewMint
4. AM BASIC, C, BASIC PM (elasticity) and WHITENING—Daily Regimen and Whitening
5. AM BASIC, PM REPAIR and WHITENING—Daily Regimen and Whitening
6. BASIC AM, BOOST and PM—Morning, Noon and Night Regimen
7. WHITENING and SUN—White and Bright
8. AM BASIC C and WRINKLE—Daily Regimen and Special Care
9. AM BASIC and MEN'S—M/F—Couple Duo—for Him and Her
10. VEGAN AM and PM—Vegan Daily Regimen
11. MENOPAUSE and PM—Daily Regimen Aging Skin 50+
12. AM BOOST and PM—Enhanced Daily Regimen
13. AM, PM, Topical Skincare
14. PROBIOTIC and PM
15. RADIANCE AND WHITENING
16. BASIC AM and Anti-Oxidant Mouth Rinse/Foam
17. ACNE/PSORIASIS and PM
18. AM BASIC and PM—Daily Regimen—AM/PM Treatment (coordinated for dry skin)
19. AM BASIC and PM—Daily Regimen—AM/PM Treatment (coordinated for oily skin)

20. AM BASIC and PM—Daily Regimen—AM/PM Treatment (coordinated for combination skin)
21. AM BASIC and PM—Daily Regimen—AM/PM Treatment (coordinated for sensitive skin)
22. AM/BASIC and PM Daily Regimen for Sensitive Teeth Seasonal Kits with Coordinated Toothpastes WINTER—ADDRESS THE SKIN ISSUES OF THE DRY COLD SEASON. AND STRESS OF THE HOLIDAY SEASON, such as:

BASIC AM and PM; Daily Regimen Holiday Peppermint flavor and WildMint flavor

BLISSED (STRESS FORMULA) and PM; HerbalMint and NewMint flavor

PROBIOTIC and PM

PROBIOTIC and DETOX

BASIC AM and DETOX

AM BASIC and PM—Daily Regimen Holiday Peppermint flavor and WildMint flavor—(coordinated for dry skin)

SUMMER—MAXIMUM PROTETION—ADDRESSES THE SKIN ISSUES OF THE SUMMER SEASON; SUNSCREEN, EXPOSURE TO THE ELEMENTS such as:

AM BASIC C and SUNSCREEN FORMULA; CitrusMint/CitrusMint flavors

AM BASIC C and SUNSCREEN FORMULA and TOPICAL or Oral Sunscreen;

CitrusMint/CitrusMint flavors

WHITENING AND SUN—White and Bright; CitrusMint/CitrusMint flavors

HOLIDAY BOXED GIFT SETS FOR Christmas, Valentines Day, Easter, Mother's Day, Fathers Day, Thanksgiving, etc. such as:

BASIC AM AND PM—DAILY REGIMEN (coordinated for a specific skin type including: normal, oily, dry, combination, sensitive and acne prone)

BASIC AM and PM with Subscription Gift Certificate or Gift Toothbrush or Razor III. CO BRANDED and/or COMPLIMENTARY BP PRODUCT BASIC AM C with Topical Sunscreen Moisturizer BASIC AM C with Oral Sunscreen such as HelioCare Capsule (Ferndale Pharmaceuticals)

BASIC AM with ORAL NR Nicotinamide Riboside—TRU NIAGIN (which is unstable in oral and topical formulas) manufactured by CHROMADEX (same as IMMULINA).

BASIC AM with branded sonic toothbrush

BASIC AM with Natural Lip Beauty Product (Lipstick, Gloss)

The following examples are of toothpaste formulations in accordance with the present invention that could be produced.

Example 1

A formulation that can be used in the morning before or after a morning meal can include the following:

| | |
|---|---|
| Water | 24.65% wt/wt |
| Sorbitol | 21.10% wt/wt |
| Glycerin | 15% wt/wt |
| Xylitol | 10% wt/wt |
| nanoXIM CarePaste (nano-hydroxyapatite water based paste additive from Fluidinova SA "nano-HAP") | 8% wt/wt |

-continued

| | |
|---|---|
| Calcium Carbonate (heavy powder 98.5%) | 7% wt/wt |
| Zeodent 165 (Dental silica thickener additive from Evonik) | 8% wt/wt |
| Veegum Pure (Magnesium Aluminum Silicate NF from Vanderbilt Minerals LLC) | 3% wt/wt |
| Manuka Honey | 1% wt/wt |
| Xanthan Gum | 0.5% wt/wt |
| Mint Blend | <1% wt/wt |
| *IMMULINA (spirulina extract from Chromadex) | 0.5% wt/wt |
| Vitamin E | 0.25% wt/wt |
| Aloe | 0.2% wt/wt |
| Bilberry extract | 0.1% wt/wt |
| d-glyclosamine | 0.1% wt/wt |

*

The toothpaste can be produced from the above formulation using the following general process: Mix the water and Veegum. This mixture can be heated for 30-60 minutes to improve solubility/dispersibility. To this the sorbitol is added. Separately blend Glycerin and xantham and add to the prior mixture. Mix in Xylitol and Nano Hydroxyapatite (nano-HAP) with stirring. Afterwards, all remaining ingredients except as noted should be added one by one until each is dissolved or dispersed. When adding the Zeodent, it should be added in divided amounts such as thirds. As mixing continues the formulation turns from a dough and slowly turns into paste. The HA is separately dissolved into water and added at the end because it is heat sensitive. Cool to room temp. Slow mix in the HA in water and then the Mint/FLAVOR is added. The examples that follow (Examples 2-28) may include different ingredients but all can be produced in generally the same way as described in this Example.

Example 2

Another formulation that can be used in the morning before or after a morning meal can include the following:

| INGREDIENT | Range % (w/w) | Exemplary formulation % (w/w) |
|---|---|---|
| VEEGUM Pure | 1-5% | 3.00% |
| Water | q.s. | 9.80% |
| Sorbitol | 25-35% | 31.45% |
| Glycerin | 5-20% | 15.00% |
| Xanthan Gum | 0.1-1.5% | 0.70% |
| Xylitol | 2-20% | 10.00% |
| Nano-Hydroxyapatite (HAP) | 0.01-10% | 8.00% |
| Glucosamine | 0-3% | 0.10% |
| SOLIDENTI | 0-10% | 1.00% |
| CoQ10 | 0-3% | 0.10% |
| Vitamin C | 0-2% | 0.10% |
| Hyaluronic acid ("HA") | 0-3% | 0.10% |
| IMMULINA | 0-4% | 0.50% |
| Honey | 0-5% | 1.00% |
| Aloe | 0-2% | 0.20% |
| Bilberry | 0-2% | 0.10% |
| Vitamin E | 0-2% | 0.25% |
| Calcium Carbonate | 5-30% | 10.00% |
| Zeodent 167 | 4-12% | 8.00% |
| Mint Blend | 0-2% | 0.60% |

Note that in all of these examples, ingredients such as VEEGUM, sorbitol, glycerin, xanthan gum, xylitol, calcium carbonate, Zeodent 167 and this flavor are used to exemplify the components of a dentifrice which may be swallowed and these ingredients can be eliminated or substituted for other ingredients know to perform the same function in similar amounts Example 3

A formulation that can help provide stress reduction and/or relaxation can include the following:

| INGREDIENT | % (w/w) |
|---|---|
| VEEGUM Pure | 3.00% |
| Water | 6.60% |
| Sorbitol | 31.45% |
| Glycerin | 15.00% |
| Xanthan Gum | 0.70% |
| Xylitol | 10.00% |
| Nano-HAP | 8.00% |
| Glucosamine | 0.10% |
| SOLIDENTI | 1.00% |
| CoQ10 | 0.10% |
| Vitamin C | 3.00% |
| HA | 0.10% |
| IMMULINA | 0.50% |
| Manuka Honey | 1.00% |
| Aloe | 0.20% |
| Bilberry | 0.10% |
| Vitamin E | 0.25% |
| Calcium Carbonate | 10.00% |
| Zeodent 167 | 8.00% |
| Ashwaganda | 0.10% |
| Green Tea | 0.10% |
| Passionflower | 0.10% |
| Flavor | 0.60% |

Example 4

A formulation that can provide a clarity, energy and a pick-me-up includes the following:

| INGREDIENT | % (w/w) |
|---|---|
| VEEGUM Pure | 3.00% |
| Water | 8.60% |
| Sorbitol | 31.45% |
| Glycerin | 15.00% |
| Xanthan Gum | 0.70% |
| Xylitol | 10.00% |
| Nano-HAP | 8.00% |
| Glucosamine | 0.10% |
| SOLIDENTI | 1.00% |
| CoQ10 | 0.10% |
| Vitamin C | 1.0% |
| HA | 0.10% |
| IMMULINA | 0.50% |
| Propolis | 1.00% |
| Aloe | 0.20% |
| Bilberry | 0.10% |
| Vitamin E | 0.25% |
| Calcium Carbonate | 10.00% |
| Zeodent 167 | 8.00% |
| Caffeine | 0.10% |
| Astragalus | 0.10% |
| Coffee Extract | 0.10% |
| Flavor | 0.60% |

Example 5

A formulation that can assist in detoxification (and can be particularly useful in normal to oil skin) includes the following:

| INGREDIENT | % (w/w) |
|---|---|
| VEEGUM Pure | 3.00% |
| Water | 6.60% |
| Sorbitol | 31.45% |
| Glycerin | 15.00% |
| Xanthan Gum | 0.70% |
| Xylitol | 10.00% |
| Nano-HAP | 8.00% |
| Glucosamine | 0.10% |
| SOLIDENTI | 1.00% |
| CoQ10 | 0.10% |
| Vitamin C | 3.00% |
| HA | 0.10% |
| IMMULINA | 0.50% |
| Honey | 1.00% |
| Aloe | 0.20% |
| Horse Chestnut | 0.10% |
| Vitamin E | 0.25% |
| Calcium Carbonate | 10.00% |
| Zeodent 167 | 8.00% |
| Gotu Kola | 0.10% |
| Flaxseed | 0.10% |
| Tea Tree | 0.10% |
| Flavor | 0.60% |

Example 6

A formulation that can be used in the evening before bed includes the following:

| INGREDIENT | % (w/w) |
|---|---|
| VEEGUM Pure | 3.00% |
| Water | 9.50% |
| Sorbitol | 31.45% |
| Glycerin | 15.00% |
| Xanthan Gum | 0.70% |
| Xylitol | 10.00% |
| Nano-HAP | 8.00% |
| Glucosamine | 0.10% |
| SOLIDENTI | 1.00% |
| CoQ10 | 0.10% |
| Vitamin C | 0.10% |
| HA | 0.10% |
| IMMULINA | 0.50% |
| Honey | 1.00% |
| Aloe | 0.20% |
| Bilberry | 0.10% |
| Vitamin E | 0.25% |
| Calcium Carbonate | 10.00% |
| Zeodent 167 | 8.00% |
| Chamomile | 0.10% |
| Skullcap | 0.10% |
| Passionflower | 0.10% |
| Mint Blend | 0.60% |

Example 7

A tooth whitening formulation can include the following:

| INGREDIENT | % (w/w) |
|---|---|
| VEEGUM Pure | 3.00% |
| Water | 9.60% |
| Sorbitol | 31.45% |
| Glycerin | 15.00% |
| Xanthan Gum | 0.70% |
| Xylitol | 10.00% |
| Nano-HAP | 8.00% |
| Glucosamine | 0.10% |
| SOLIDENTI | 1.00% |
| CoQ10 | 0.10% |

-continued

| INGREDIENT | % (w/w) |
|---|---|
| Vitamin C | 0.10% |
| HA | 0.10% |
| IMMULINA | 0.50% |
| Honey | 1.00% |
| Aloe | 0.20% |
| Bilberry | 0.10% |
| Vitamin E | 0.25% |
| Calcium Carbonate | 10.00% |
| Zeodent 167 | 8.00% |
| Charcoal/Bamboo Powder | 0.10% |
| Grapefruit Seed Extract | 0.10% |
| Mint Blend | 0.60% |

Example 8

An acne/psoriasis formulation can include the following:

| INGREDIENT | % (w/w) |
|---|---|
| VEEGUM Pure | 3.00% |
| Water | 9.50% |
| Sorbitol | 31.45% |
| Glycerin | 15.00% |
| Xanthan Gum | 0.70% |
| Xylitol | 10.00% |
| Nano-HAP | 8.00% |
| Glucosamine | 0.10% |
| SOLIDENTI | 1.00% |
| CoQ10 | 0.10% |
| Vitamin C | 0.10% |
| HA | 0.10% |
| IMMULINA | 0.50% |
| Honey | 1.00% |
| Aloe | 0.20% |
| Bilberry | 0.10% |
| Vitamin E | 0.25% |
| Calcium Carbonate | 10.00% |
| Zeodent 167 | 8.00% |
| Astaxanthin | 0.10% |
| Grapefruit Seed Extract | 0.10% |
| Polypodium Leucotomos | 0.10% |
| Flavor | 0.60% |

Example 9

A CBD containing formulation can include the following:

| INGREDIENT | % (w/w) |
|---|---|
| VEEGUM Pure | 3.00% |
| Water | 9.60% |
| Sorbitol | 31.45% |
| Glycerin | 15.00% |
| Xanthan Gum | 0.70% |
| Xylitol | 10.00% |
| Nano-HAP | 8.00% |
| Glucosamine | 0.10% |
| SOLIDENTI | 1.00% |
| CoQ10 | 0.10% |
| Vitamin C | 0.10% |
| HA | 0.10% |
| IMMULINA | 0.50% |
| Honey | 1.00% |
| Aloe | 0.20% |
| Bilberry | 0.10% |
| Vitamin E | 0.25% |
| Calcium Carbonate | 10.00% |
| Zeodent 167 | 8.00% |
| CBD CRYSTALS | 0.05% |

-continued

| INGREDIENT | % (w/w) |
|---|---|
| Grapefruit Seed Extract | 0.10% |
| FLAVOR | 0.60% |

Example 10

A formulation that can be used for reducing toxicity, and can be particularly useful for oily skin, can include the following:

| INGREDIENT | % (w/w) |
|---|---|
| VEEGUM Pure | 3.00% |
| Water | 8.60% |
| Sorbitol | 31.45% |
| Glycerin | 15.00% |
| Xanthan Gum | 0.70% |
| Xylitol | 10.00% |
| Nano-HAP | 8.00% |
| Astragalus | 0.10% |
| SOLIDENTI | 1.00% |
| CoQ10 | 0.10% |
| Vitamin C | 1.00% |
| HA | 0.10% |
| IMMULINA | 0.50% |
| Manuka Honey | 1.00% |
| Aloe | 0.20% |
| Horse Chestnut | 0.10% |
| Vitamin E | 0.25% |
| Calcium Carbonate | 10.00% |
| Zeodent 167 | 8.00% |
| Wheatgrass | 0.10% |
| Chlorella | 0.10% |
| Tea Tree | 0.10% |
| Flavor | 0.60% |

Example 11

A second formulation that can be used at any time of day but particularly in the morning, can include the following:

| INGREDIENT | % (w/w) |
|---|---|
| VEEGUM Pure | 3.00% |
| Water | balance |
| Sorbitol | 31.45% |
| Glycerin | 15.00% |
| Xanthan Gum | 0.70% |
| Xylitol | 10.00% |
| Nano-HAP | 8.00% |
| Glucosamine | 0.10% |
| SOLIDENTI | 1.00% |
| CoQ10 | 0.10% |
| HA | 0.10% |
| IMMULINA | 0.50% |
| Manuka Honey | 1.00% |
| Aloe | 0.20% |
| Bilberry | 0.10% |
| Vitamin E | 0.25% |
| Calcium Carbonate | 10.00% |
| Zeodent 167 | 8.00% |
| Mint Blend 1 | 0.60% |

Example 12

A formulation that can be used to help address wrinkles and crow's feet, and can be particularly useful for combination skin, can include the following:

| INGREDIENT | % (w/w) |
|---|---|
| VEEGUM Pure | 3.00% |
| Water | 8.60% |
| Sorbitol | 31.45% |
| Glycerin | 15.00% |
| Xanthan Gum | 0.70% |
| Xylitol | 10.00% |
| Nano-HAP | 8.00% |
| Glucosamine | 0.10% |
| SOLIDENTI | 1.00% |
| CoQ10 | 0.10% |
| Vitamin C | 1.00% |
| HA | 0.10% |
| IMMULINA | 0.50% |
| Manuka Honey | 1.00% |
| Aloe | 0.20% |
| Bilberry | 0.10% |
| Vitamin E | 0.25% |
| Calcium Carbonate | 10.00% |
| Zeodent 167 | 8.00% |
| Green Tea | 0.10% |
| Rose Hip | 0.10% |
| Grapefruit Seed Extract | 0.10% |
| Mint Blend | 0.60% |

Example 13

This formulation that is particularly good for Vegans can include the following:

| INGREDIENT | % (w/w) |
|---|---|
| VEEGUM Pure | 3.00% |
| Water | 9.00% |
| Sorbitol | 31.45% |
| Glycerin | 15.00% |
| Xanthan Gum | 0.70% |
| Xylitol | 10.00% |
| Nano-HAP | 8.00% |
| Glucosamine | 0.10% |
| SOLIDENTI | 1.00% |
| CoQ10 | 0.10% |
| Vitamin C | 0.10% |
| HA | 0.10% |
| IMMULINA | 0.50% |
| Vitamin B2 | 1.0% |
| Vitamin B complex | 0.5% |
| Aloe | 0.20% |
| Bilberry | 0.10% |
| Vitamin E | 0.25% |
| Calcium Carbonate | 10.00% |
| Zeodent 167 | 8.00% |
| Caffeine | 0.10% |
| Astragalus | 0.10% |
| Coffee Extract | 0.10% |
| Flavor | 0.60% |

Example 14

A probiotic formulation can include the following:

| INGREDIENT | % (w/w) |
|---|---|
| VEEGUM Pure | 3.00% |
| Water | 9.60% |
| Sorbitol | 31.45% |
| Glycerin | 15.00% |
| Xanthan Gum | 0.70% |
| Xylitol | 10.00% |
| Nano-HAP | 8.00% |
| Glucosamine | 0.10% |
| SOLIDENTI | 1.00% |
| CoQ10 | 0.10% |
| Vitamin C | 0.10% |
| HA | 0.10% |
| IMMULINA | 0.50% |
| Honey | 1.00% |
| Aloe | 0.20% |
| Bilberry | 0.10% |
| Vitamin E | 0.25% |
| Calcium Carbonate | 10.00% |
| Zeodent 167 | 8.00% |
| *Lactobacillus Rhamosus* | 0.10% |
| *Lactobacillus Plantarum* | 0.10% |
| *Bifidobacterium infantus* | 0.10% |
| Mint Blend | 0.60% |

Example 15

A formulation that can be used at any time of day, but particularly in the morning, can include the following:

| INGREDIENT | % (w/w) |
|---|---|
| VEEGUM Pure | 3.00% |
| Water | 9.80% |
| Sorbitol | 31.45% |
| Glycerin | 15.00% |
| Xanthan Gum | 0.70% |
| Xylitol | 10.00% |
| Nano-HAP | 8.00% |
| Collagen | 0.10% |
| SOLIDENTI | 1.00% |
| Selenium | 0.10% |
| Vitamin C | 0.10% |
| HA | 0.10% |
| IMMULINA | 0.50% |
| Honey | 1.00% |
| Aloe | 0.20% |
| Resveratrol | 0.10% |
| Vitamin E | 0.25% |
| Calcium Carbonate | 10.00% |
| Zeodent 167 | 8.00% |
| CardamonMint/NewMint | 0.60% |

Example 16

A formulation that can be used to help address wrinkles can include the following:

| INGREDIENT | % (w/w) |
|---|---|
| VEEGUM Pure | 3.00% |
| Water | 8.60% |
| Sorbitol | 31.45% |
| Glycerin | 15.00% |
| Xanthan Gum | 0.70% |
| Xylitol | 10.00% |
| Nano-HAP | 8.00% |
| Glucosamine | 0.10% |
| SOLIDENTI | 1.00% |
| Pomegranate | 0.10% |
| Vitamin C | 1.00% |
| HA | 0.10% |
| IMMULINA | 0.50% |
| Honey | 1.00% |
| Aloe | 0.20% |
| CoEnzymeQ10 | 0.10% |
| Vitamin E | 0.25% |
| Calcium Carbonate | 10.00% |
| Zeodent 167 | 8.00% |

-continued

| INGREDIENT | % (w/w) |
|---|---|
| Vitamin D | 0.10% |
| Vitamin A | 0.10% |
| Zinc | 0.10% |
| Mint Blend | 0.60% |

Example 17

A formulation that can be used to help support the health of the user's hair and/or nails can include the following:

| INGREDIENT | % (w/w) |
|---|---|
| VEEGUM Pure | 3.00% |
| Water | 9.50% |
| Sorbitol | 31.45% |
| Glycerin | 15.00% |
| Xanthan Gum | 0.70% |
| Xylitol | 10.00% |
| Nano-HAP | 8.00% |
| Collagen | 0.10% |
| SOLIDENTI | 1.00% |
| CoQ10 | 0.10% |
| Vitamin C | 0.10% |
| HA | 0.10% |
| IMMULINA | 0.50% |
| Honey | 1.00% |
| Aloe | 0.20% |
| Bilberry | 0.10% |
| Vitamin E | 0.25% |
| Calcium Carbonate | 10.00% |
| Zeodent 167 | 8.00% |
| Choline | 0.10% |
| Biotin | 0.10% |
| Polygonum | 0.10% |
| Flavor | 0.60% |

Example 18

A formulation that can be used to address the skin conditions associated with menopause, and can be particularly useful for dry skin, can include the following:

| INGREDIENT | % (w/w) |
|---|---|
| VEEGUM Pure | 3.00% |
| Water | 9.50% |
| Sorbitol | 31.45% |
| Glycerin | 15.00% |
| Xanthan Gum | 0.70% |
| Xylitol | 10.00% |
| Nano-HAP | 8.00% |
| Glucosamine | 0.10% |
| SOLIDENTI | 1.00% |
| CoQ10 | 0.10% |
| Vitamin C | 0.10% |
| HA | 0.10% |
| IMMULINA | 0.50% |
| Propolis | 1.00% |
| Aloe | 0.20% |
| Red Clover | 0.10% |
| Vitamin E | 0.25% |
| Calcium Carbonate | 10.00% |
| Zeodent 167 | 8.00% |
| Rose Hip | 0.10% |
| Licorice Root | 0.10% |
| Evening Primrose Oil | 0.10% |
| Flavor | 0.60% |

Example 19

Another formulation that can be used in the evening before bed, can include the following:

| INGREDIENT | % (w/w) |
|---|---|
| VEEGUM Pure | 3.00% |
| Water | 9.50% |
| Sorbitol | 31.45% |
| Glycerin | 15.00% |
| Xanthan Gum | 0.70% |
| Xylitol | 10.00% |
| Nano-HAP | 8.00% |
| Polygonum | 0.10% |
| SOLIDENTI | 1.00% |
| CoQ10 | 0.10% |
| Vitamin C | 0.10% |
| HA | 0.10% |
| IMMULINA | 0.50% |
| Honey | 1.00% |
| Aloe | 0.20% |
| Goji | 0.10% |
| Vitamin E | 0.25% |
| Calcium Carbonate | 10.00% |
| Zeodent 167 | 8.00% |
| Chamomile | 0.10% |
| Skullcap | 0.10% |
| Melatonin | 0.10% |
| Herbal Mint | 0.60% |

Example 20

A formulation that can help support skin's radiance/glow can include the following:

| INGREDIENT | % (w/w) |
|---|---|
| VEEGUM Pure | 3.00% |
| Water | 9.50% |
| Sorbitol | 31.45% |
| Glycerin | 15.00% |
| Xanthan Gum | 0.70% |
| Xylitol | 10.00% |
| Nano-HAP | 8.00% |
| Glucosamine | 0.10% |
| SOLIDENTI | 1.00% |
| CoQ10 | 0.10% |
| Vitamin C | 0.10% |
| HA | 0.10% |
| IMMULINA | 0.50% |
| Honey | 1.00% |
| Aloe | 0.20% |
| Bilberry | 0.10% |
| Vitamin E | 0.25% |
| Calcium Carbonate | 10.00% |
| Zeodent 167 | 8.00% |
| Vitamin A | 0.10% |
| Acai | 0.10% |
| Sunflower Shoot | 0.10% |
| Black Currant Seed | 0.10% |
| Mint Blend | 0.60% |

Example 21

A moisturizing formulation that can be used at any time of day but particularly in the morning, and can be particularly useful for dry skin, can include the following:

| INGREDIENT | % (w/w) |
|---|---|
| VEEGUM Pure | 3.00% |
| Water | 9.80% |
| Sorbitol | 31.45% |
| Glycerin | 15.00% |
| Xanthan Gum | 0.70% |
| Xylitol | 10.00% |
| Nano-HAP | 8.00% |
| Bladderwrack | 0.10% |
| SOLIDENTI | 1.00% |
| Lingonberry | 0.10% |
| Vitamin C | 0.10% |
| HA | 0.10% |
| IMMULINA | 0.50% |
| Honey | 1.00% |
| Aloe | 0.20% |
| Bilberry | 0.10% |
| Vitamin E | 0.25% |
| Calcium Carbonate | 10.00% |
| Zeodent 167 | 8.00% |
| Flavor | 0.60% |

Example 22

An additional formulation that can be used for skin lightening, can include the following:

| INGREDIENT | % (w/w) |
|---|---|
| VEEGUM Pure | 3.00% |
| Water | 9.80% |
| Sorbitol | 31.45% |
| Glycerin | 15.00% |
| Xanthan Gum | 0.70% |
| Xylitol | 10.00% |
| Nano-HAP | 8.00% |
| Glucosamine | 0.10% |
| SOLIDENTI | 1.00% |
| CoQ10 | 0.10% |
| Vitamin C | 0.10% |
| HA | 0.10% |
| IMMULINA | 0.50% |
| Manuka Honey | 1.00% |
| Aloe | 0.20% |
| Bilberry | 0.10% |
| Vitamin E | 0.25% |
| Calcium Carbonate | 10.00% |
| Zeodent 167 | 8.00% |
| Mint Blend 1 | 0.60% |

Example 23

A formulation that can be used to help reduce inflammation, and can be particularly useful for sensitive skin, can include the following:

| INGREDIENT | % (w/w) |
|---|---|
| VEEGUM Pure | 3.00% |
| Water | 9.70% |
| Sorbitol | 31.45% |
| Glycerin | 15.00% |
| Xanthan Gum | 0.70% |
| Xylitol | 10.00% |
| Nano-HAP | 8.00% |
| Chondroitin | 0.10% |
| ALA | 0.10% |
| SOLIDENTI | 1.00% |
| Turmeric | 0.10% |
| Vitamin C | 0.10% |
| HA | 0.10% |

-continued

| INGREDIENT | % (w/w) |
|---|---|
| IMMULINA | 0.50% |
| Propolis | 1.00% |
| Aloe | 0.20% |
| Omega Fish Oil | 0.10% |
| Vitamin E | 0.25% |
| Calcium Carbonate | 10.00% |
| Zeodent 167 | 8.00% |
| Flavor | 0.60% |

Example 24

An additional formulation that can be used to provide a mid-day pick me up, can include the following:

| INGREDIENT | % (w/w) |
|---|---|
| VEEGUM Pure | 3.00% |
| Water | 9.50% |
| Sorbitol | 31.45% |
| Glycerin | 15.00% |
| Xanthan Gum | 0.70% |
| Xylitol | 10.00% |
| Nano-HAP | 8.00% |
| Glucosamine | 0.10% |
| SOLIDENTI | 1.00% |
| CoQ10 | 0.10% |
| Vitamin C | 0.10% |
| HA | 0.10% |
| IMMULINA | 0.50% |
| Propolis | 1.00% |
| Aloe | 0.20% |
| Bilberry | 0.10% |
| Vitamin E | 0.25% |
| Calcium Carbonate | 10.00% |
| Zeodent 167 | 8.00% |
| Shisandra Berry | 0.10% |
| Eleuthero | 0.10% |
| Ashwaganda | 0.10% |
| Flavor | 0.60% |

Example 25

A formulation that can be used to provide protection and/or support repair of sun damage, can include the following:

| INGREDIENT | % (w/w) |
|---|---|
| VEEGUM Pure | 3.00% |
| Water | 6.70% |
| Sorbitol | 31.45% |
| Glycerin | 15.00% |
| Xanthan Gum | 0.70% |
| Xylitol | 10.00% |
| Nano-HAP | 8.00% |
| Lutein | 0.10% |
| SOLIDENTI | 1.00% |
| Vitamin D | 0.10% |
| Vitamin C | 3.00% |
| HA | 0.10% |
| IMMULINA | 0.50% |
| Manuka Honey | 1.00% |
| Aloe | 0.20% |
| Bilberry | 0.10% |
| Vitamin E | 0.25% |
| Calcium Carbonate | 10.00% |
| Zeodent 167 | 8.00% |
| Polypodium | 0.10% |

-continued

| INGREDIENT | % (w/w) |
|---|---|
| Grapefruit Seed Extract | 0.10% |
| Flavor | 0.60% |

Example 26

A foaming formulation that can be used in the morning before or after a morning meal can include the following:

| | |
|---|---|
| Water | 22.65% wt/wt |
| Surfactant (glycolipid) | 1-2% wt/wt |
| Sorbitol | 21.10% wt/wt |
| Glycerin | 15% wt/wt |
| Xylitol | 10% wt/wt |
| nanoXIM CarePaste (nano-hydroxyapatite water based paste additive from Fluidinova SA) | 8% wt/wt |
| Calcium Carbonate (heavy powder 98.5%) | 7% wt/wt |
| Zeodent 165 (Dental silica thickener additive from Evonik) | 8% wt/wt |
| Veegum Pure (Magnesium Aluminum Silicate NF from Vanderbilt Minerals LLC) | 3% wt/wt |
| Manuka Honey | 1% wt/wt |
| Xanthan Gum | 0.5% wt/wt |
| Mint Blend | <1% wt/wt |
| *IMMULINA (spirulina extract from Chromadex) | 0.5% wt/wt |
| Vitamin E | 0.25% wt/wt |
| Aloe | 0.2% wt/wt |
| Bilberry extract | 0.1% wt/wt |
| d-glyclosamine | 0.1% wt/wt |

Example 27

A formulation that can be used in the morning before or after a morning meal can include the following:

| | |
|---|---|
| Water | 24.407% wt/wt |
| Sodium Fluoride | 0.243% wt/wt |
| Sorbitol | 21.10% wt/wt |
| Glycerin | 15% wt/wt |
| Xylitol | 10% wt/wt |
| nanoXIM CarePaste (nano-hydroxyapatite water based paste additive from Fluidinova SA) | 8% wt/wt |
| Calcium Carbonate (heavy powder 98.5%) | 7% wt/wt |
| Zeodent 165 (Dental silica thickener additive from Evonik) | 8% wt/wt |
| Veegum Pure (Magnesium Aluminum Silicate NF from Vanderbilt Minerals LLC) | 3% wt/wt |
| Manuka Honey | 1% wt/wt |
| Xanthan Gum | 0.5% wt/wt |
| Mint Blend | <1% wt/wt |
| *IMMULINA (spirulina extract from Chromadex) | 0.5% wt/wt |
| Vitamin E | 0.25% wt/wt |
| Aloe | 0.2% wt/wt |
| Bilberry extract | 0.1% wt/wt |
| d-glyclosamine | 0.1% wt/wt |

Example 28

A formulation that can assist in dealing with the effects of stress can include the following:

| INGREDIENT | % (w/w) |
|---|---|
| VEEGUM Pure | 3.00% |
| Water | balance |
| Sorbitol | 31.45% |
| Glycerin | 15.00% |
| Xanthan Gum | 0.70% |
| Xylitol | 10.00% |
| Nano-HAP | 8.00% |
| Glucosamine | 0.10% |
| SOLIDENTI | 1.00% |
| CoQ10 | 0.10% |
| Vitamin C | 3.00% |
| HA | 0.10% |
| IMMULINA | 0.50% |
| Aloe | 0.20% |
| Bilberry | 0.10% |
| Vitamin E | 0.25% |
| Calcium Carbonate | 10.00% |
| Zeodent 167 | 8.00% |
| Ashwaganda | 0.10% |
| Green Tea | 0.10% |
| Passionflower | 0.10% |
| Flavor | 0.60% |

Example 29

A Basic PM formulation can include the following:

| INGREDIENT | % (w/w) |
|---|---|
| VEEGUM Pure | 3.00% |
| Water | 11.50% |
| Sorbitol | 31.45% |
| Glycerin | 15.00% |
| Xanthan Gum | 0.70% |
| Xylitol | 10.00% |
| Nano-HAP | 8.00% |
| Glucosamine | 0.10% |
| CoQ10 | 0.10% |
| Vitamin C | 0.10% |
| HA | 0.10% |
| Spirulina | 0.50% |
| Aloe | 0.20% |
| Bilberry | 0.10% |
| Vitamin E | 0.25% |
| Calcium Carbonate | 10.00% |
| Zeodent 167 | 8.00% |
| Chamomile | 0.10% |
| Skullcap | 0.10% |
| Passionflower | 0.10% |
| Mint Blend 1 | 0.60% |

Example 30

A PM formulation (repair) can include the following:

| INGREDIENT | Range of Ingredients % (w/w) | Exemplary formulation % (w/w) |
|---|---|---|
| VEEGUM Pure | 1-5% | 3.00% |
| Water | q.s. | 10.50% |
| Sorbitol | 25-35% | 31.45% |
| Glycerin | 5-20% | 15.00% |
| Xanthan Gum | 0.1-1.5 | 0.70% |
| Xylitol | 2-20% | 10.00% |

-continued

| INGREDIENT | Range of Ingredients % (w/w) | Exemplary formulation % (w/w) |
|---|---|---|
| Nano-HAP | 0.01-10% | 8.00% |
| Glucosamine | 0-3% | 0.10% |
| SOLIDENTI | 0-10% | 1.00% |
| CoQ10 | 0-3% | 0.10% |
| Vitamin C | 0-2% | 0.10% |
| HA | 0-3% | 0.10% |
| Spirulina | 0-4% | 0.50% |
| Honey | 0-4% | 0 |
| Aloe | 0-% | 0.20% |
| Bilberry | 0-3% | 0.10% |
| Vitamin E | 0-5% | 0.25% |
| Calcium Carbonate | 5-30% | 10.00% |
| Zeodent 167 | 4-12% | 8.00% |
| Collagen | 0-3% | 0.10% |
| Grapeseed extract | 0-3% | 0.10% |
| One or more restfulness enhancing agents such as melatonin, poria, albizza flower, jujube, polygonum, Valerian, Lavender, Hop, St Johns Wort, Valerian, Hops, Blue Vervain, Passionflower, Wild Lettuce, Hawthorn and, goji | Total of 0-3% | Passionflower extract 0.10% |
| Mint Blend 1 | 0-4% | 0.60% |

Example 31

A Basic AM formulation, particularly good for sensitive teeth, can include the following:

| INGREDIENT | % (w/w) |
|---|---|
| VEEGUM Pure | 3.00% |
| Water | 6.80% |
| Sorbitol | 31.45% |
| Glycerin | 15.00% |
| Xanthan Gum | 0.70% |
| Xylitol | 10.00% |
| Nano-HAP | 15.00% |
| Glucosamine | 0.10% |
| SOLIDENTI | 1.00% |
| CoQ10 | 0.10% |
| Vitamin C | 0.10% |
| HA | 0.10% |
| Spirulina | 0.50% |
| Aloe | 0.20% |
| Bilberry | 0.10% |
| Vitamin E | 0.25% |
| Calcium Carbonate | 10.00% |
| Zeodent 167 | 8.00% |
| Mint Blend 1 | 0.60% |

Example 32

A BASIC PM formulation can include the following:

| INGREDIENT | % (w/w) |
|---|---|
| VEEGUM Pure | 3.00% |
| Water | 10.50% |
| Sorbitol | 31.45% |
| Glycerin | 15.00% |
| Xanthan Gum | 0.70% |
| Xylitol | 10.00% |
| Nano-HAP | 8.00% |
| Glucosamine | 0.10% |
| CoQ10 | 0.10% |
| Vitamin C | 0.10% |
| HA | 0.10% |
| Spirulina | 0.50% |
| Propolis | 1.00% |
| Aloe | 0.20% |
| Bilberry | 0.10% |
| Vitamin E | 0.25% |
| Calcium Carbonate | 10.00% |
| Zeodent 167 | 8.00% |
| Chamomile | 0.10% |
| Skullcap | 0.10% |
| Passionflower | 0.10% |
| Mint Blend 1 | 0.60% |

Example 33

A BASIC AM formulation can include the following:

| INGREDIENT | % (w/w) |
|---|---|
| VEEGUM Pure | 3.00% |
| Water | 11.80% |
| Sorbitol | 31.45% |
| Glycerin | 15.00% |
| Xanthan Gum | 0.70% |
| Xylitol | 10.00% |
| Nano-HAP | 8.00% |
| Glucosamine | 0.10% |
| CoQ10 | 0.10% |
| Vitamin C | 0.10% |
| Spirulina | 0.50% |
| Aloe | 0.20% |
| Bilberry | 0.10% |
| Vitamin E | 0.25% |
| Calcium Carbonate | 10.00% |
| Zeodent 167 | 8.00% |
| Mint Blend 1 | 0.60% |

Example 34

A BASIC AM (elasticity) formulation can include the following:

| INGREDIENT | Exemplary formulation wt % (wt/wt) | Range wt % (wt/wt) |
|---|---|---|
| VEEGUM Pure | 3.00% | 1-5% |
| Water | 10.80% | q.s. |
| Sorbitol | 31.45% | 25-35% |
| Glycerin | 15.00% | 5-20% |
| Xanthan Gum | 0.70% | 0.1-1.5% |
| Xylitol | 10.00% | 2-20% |
| Nano-HAP | 8.00% | 0.01-10% |
| Glucosamine | 0.10% | 0-3% |
| Solidenti | 1.00% | 0-10% |
| CoQ10 | 0.10% | 0-3% |
| Vitamin C | 0.10% | 0-2% |
| HA | 0.10% | 0-3% |
| Immulina | 0.50% | 0-4% |
| Aloe | 0.20% | 0-2% |
| Bilberry | 0.10% | 0-2% |
| Vitamin E | 0.25% | 0-2% |
| Calcium Carbonate | 10.00% | 5-30% |
| Zeodent 167 | 8.00% | 4-12% |
| Mint Blend 1 | 0.60% | 0-2% |

Example 35

A PM REPAIR formulation can include the following:

| INGREDIENT | % (w/w) |
|---|---|
| VEEGUM Pure | 3.00% |
| Water | 9.55% |
| Sorbitol | 31.45% |
| Glycerin | 15.00% |
| Xanthan Gum | 0.70% |
| Xylitol | 10.00% |
| Nano-Hydroxyapatite | 8.00% |
| Glucosamine | 0.10% |
| Solidenti | 1.00% |
| CoQ10 | 0.10% |
| Vitamin C | 0.10% |
| HA | 0.10% |
| Immulina | 0.50% |
| Aloe | 0.20% |
| Bilberry | 0.10% |
| Vitamin E | 0.25% |
| Valerian | 0.15% |
| Green Tea Blend | 1.00% |
| Calcium Carbonate | 10.00% |
| Zeodent 167 | 8.00% |
| Mint Blend 1 | 0.60% |

Example 36

A BASIC PM (elasticity) formulation can include the following:

| INGREDIENT | % (w/w) |
|---|---|
| VEEGUM Pure | 3.00% |
| Water | 9.50% |
| Sorbitol | 31.45% |
| Glycerin | 15.00% |
| Xanthan Gum | 0.70% |
| Xylitol | 10.00% |
| Nano-Hydroxyapatite | 8.00% |
| Glucosamine | 0.10% |
| Solidenti | 2.00% |
| CoQ10 | 0.10% |
| Vitamin C | 0.10% |
| HA | 0.10% |
| Immulina | 0.50% |
| Aloe | 0.20% |
| Bilberry | 0.10% |
| Vitamin E | 0.25% |
| Valerian | 0.20% |
| Passionflower | 0.10% |
| Calcium Carbonate | 10.00% |
| Zeodent 167 | 8.00% |
| Mint Blend 1 | 0.60% |

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of supporting health, well-being and/or appearance of a user's skin through the coordinated application of two different toothpastes daily to the oral cavity of the user, comprising:

a) applying to the oral cavity of the user proximate to the user waking a first toothpaste formulation supporting skin elasticity containing at least three active agent supporting skin elasticity;

b) brushing the oral cavity with the first toothpaste formulation;

c) swallowing the first toothpaste formulation;

d) applying to the oral cavity of the user proximate to the user going to sleep a second toothpaste formulation supporting skin repair or elasticity containing at least three active agent supporting skin repair and/or elasticity wherein the second toothpaste formulation is different than the first toothpaste formulation;

e) brushing the oral cavity with the second toothpaste formulation; and f) swallowing the second toothpaste formulation;

and wherein the first and second toothpaste formulations are each administered in an amount sufficient to provide at least three of the first active agents supporting skin elasticity and/or skin repair including spirulina 10 μg-500 mg; aloe 10 μg-500 mg; coenzyme Q10 10 μg-500 mg; bilberry 10 μg-500 mg; glucosamine 10 μg-500 mg; Vitamin E 10 μg-500 mg; Vitamin C 10 μg-500 mg; or hyaluronic acid (HA) 10 μg-500 mg; and further comprising at least one excipient including an abrasive, a carrier, a sweetener, a flavoring, a coloring, a stabilizer, a preservative, a viscosity enhancer, a pH adjuster, a buffer, a sparkle, a gelling agent, a surfactant, an effervescent agent, a binder, a thickener, a rheology modifying agent, a remineralizing agent, a humectant, a desensitizing agent, a sensitivity agent, a whitening agent, a mucosal adhesive, a bad breath agent, a gingivitis agent, an astringent, or an oxidizing agent, wherein the second toothpaste formulation further comprises at least one active agent supporting restfulness selected including melatonin, poria, albizza flower, jujube, polygonum, valerian, lavender, St. Johns wort, valerian, hops, blue vervain, passionflower, wild lettuce, green tea extract, hawthorn, or, goji.

2. The method of claim 1, wherein the first toothpaste formulation further comprises at least one second active agent supporting skin elasticity including aloe barbadensis, bilberry, coenzyme Q10, Vitamin E, glucosamine, spirulina, hyaluronic acid, Vitamin C, a mixture of *Centella asiatica* extract, *Polygonum cuspidatum* root extract, *Scutellaria baicalensis* root extract, *Camellia sinensis* leaf extract, *Glycyrrhiza glabre* (licorice) root extract, *Chamomilla recutita* (matricaria) flower extract, *Rosmarinus officinalis* (rosemary) leaf extract, and *Salvia officinalis* (sage) extract, propanediol and water, *Centella asiatica* extract, *Polygonum cuspidatum* root extract, *Scutellaria baicalensis* root extract, *Camellia sinensis* leaf extract, *Glycyrrhiza glabra* (licorice) root extract, *Chamomilla recutita* (matricaria) flower extract, or *Chamomilla recutita*, wherein the second active agent supporting skin elasticity is different than the first active agents supporting skin elasticity and/or skin repair.

3. The method of claim 1, wherein the second toothpaste formulation further comprises at least one second active agent supporting skin elasticity including Aloe barbadensis, bilberry, coenzyme Q10, Vitamin E, glucosamine, spirulina, hyaluronic acid, Vitamin C, a mixture of *Centella asiatica* extract, *Polygonum cuspidatum* root extract, *Scutellaria baicalensis* root extract, *Camellia sinensis* leaf extract, *Glycyrrhiza glabre* (licorice) root extract, *Chamomilla recutita* (matricaria) flower extract, *Rosmarinus officinalis* (rosemary) leaf extract, and *Salvia officinalis* (sage) extract, propanediol and water, *Centella asiatica* extract, *Polygonum cuspidatum* root extract, *Scutellaria baicalensis* root extract, *Camellia sinensis* leaf extract, *Glycyrrhiza glabra* (licorice) root extract, *Chamomilla recutita*(matricaria) flower extract, or *Chamomilla recutita*, wherein the second active agent supporting skin elasticity is different than the first active agents supporting skin elasticity and/or skin repair.

4. The method of claim 1, wherein the second toothpaste formulation further comprises at least one second active agent supporting skin repair including Vitamin C, aloe barbadensis, chamomile flower, coenzyme Q10, Vitamin E, glucosamine, hyaluronic acid, honey, passionflower, spirulina, zinc, pearl powder, polypodium leucotomos, pomegranate extracts, collagen, cycloastragenol, nicotinamide riboside, nicotinamide mononucleotide, turmeric, protein, Vitamin D, Vitamin K, alpha linolenic acid, grape seed extract, collagen peptide, crocin, astragalus, lutein, resveratrol, ceramides, ferulic acid, sunflower shoot and propolis, and a mixture thereof, wherein the second active agent supporting skin repair is different than the first active agents supporting skin elasticity and/or skin repair.

5. The method of claim 2, wherein the second toothpaste formulation further comprises at least one second active agent supporting skin repair including Vitamin C, aloe barbadensis, chamomile flower, coenzyme Q10, Vitamin E, glucosamine, hyaluronic acid, honey, passionflower, spirulina, zinc, pearl powder, polypodium leucotomos, pomegranate extracts, collagen, cycloastragenol, nicotinamide riboside, nicotinamide mononucleotide, turmeric, protein, Vitamin D, Vitamin K, alpha linolenic acid, grape seed extract, collagen peptide, crocin, astragalus, lutein, resveratrol, ceramides, ferulic acid, sunflower shoot or propolis.

6. The method of claim 5, wherein the second toothpaste formulation further comprises at least one second active agent supporting restfulness selected from the group consisting of: melatonin, poria, albizza flower, jujube, polygonum, valerian, lavender, St. Johns wort, valerian, hops, blue vervain, passionflower, wild lettuce, green tea extract, hawthorn, or, goji.

7. The method of claim 1, wherein the first and the second toothpaste formulations are both formulated to treat a particular skin type selected from the group consisting of: dry skin; oily skin; combination skin; sensitive skin; acned skin and normal skin.

8. The method of claim 5, wherein the first and the second toothpaste formulations are both formulated to treat a particular skin type selected from the group consisting of: dry skin; oily skin; combination skin; sensitive skin; acned skin and normal skin.

9. The method of claim 1, wherein steps a)-f) are repeated daily.

10. The method of claim 9, wherein steps a)-f) are repeated daily for at least about 2 weeks.

11. The method of claim 10, wherein steps a)-f) are repeated daily for at least about 4 weeks.

12. The method of claim 1, wherein the first and second toothpaste formulations include:

a toothpaste base comprising 20-50 wt % of the humectant; 1-20% wt % of the abrasive including a carbonate, bicarbonate, phosphate, silica or silicate or alumina abrasive; 0.5-20 wt % of the binder; and 1-20% of the remineralizing agent; and wherein the amount of the at least three of the first active agents supporting skin elasticity and/or skin repair included is:

up to about 3 wt % of glucosamine;

up to about 10 wt % of a mixture of *Centella asiatica* extract, *Polygonum cuspidatum* root extract, *Scutellaria baicalensis* root extract, *Camellia sinensis* leaf extract, *Glycyrrhiza glabre* (licorice) root extract, *Chamomilla recutita* (matricaria) flower extract, *Rosmarinus officinalis* (rosemary) leaf extract, and *Salvia officinalis* (sage) extract, propanediol and water;

up to about 3 wt % coenzyme Q10;

up to about 5 wt % Vitamin C;

up to about 3 wt % of hyaluronic acid (HA);

up to about 4 wt % of spirulina;

up to about 2 wt % of aloe;

up to about 2 wt % of bilberry; or up to about 2 wt % of Vitamin E;

wherein the second formulation includes the at least one active agent supporting restfulness in an amount up to about 3 wt %;

with the balance being water.

13. The method of claim 12, wherein the first and second formulations include the toothpaste base with the binder selected from the group consisting of a gum, a cellulose, a clay, and a silicon dioxide, and mixtures thereof, the remineralizing agent, and wherein the at least three of the first active agents supporting skin elasticity and/or skin repair include a mixture of *Centella asiatica* extract, *Polygonum cuspidatum* root extract, *Scutellaria baicalensis* root extract, *Camellia sinensis* leaf extract, *Glycyrrhiza glabre* (licorice) root extract, *Chamomilla recutita* (matricaria) flower extract, *Rosmarinus officinalis* (rosemary) leaf extract, and *Salvia officinalis* (sage) extract, propanediol and water, or spirulina.

* * * * *